US010590114B2

(12) United States Patent
Estrada et al.

(10) Patent No.: US 10,590,114 B2
(45) Date of Patent: Mar. 17, 2020

(54) COMPOUNDS, COMPOSITIONS, AND METHODS

(71) Applicant: Denali Therapeutics Inc., South San Francisco, CA (US)

(72) Inventors: Anthony A. Estrada, San Mateo, CA (US); Jianwen A. Feng, San Mateo, CA (US); Joseph P. Lyssikatos, South San Francisco, CA (US); Zachary K. Sweeney, Redwood City, CA (US); Javier de Vicente Fidalgo, Foster City, CA (US)

(73) Assignee: Denali Therapautics Inc., South San Francisco, CA (US)

( * ) Notice: Subject to any disclaimer, the term of this patent is extended or adjusted under 35 U.S.C. 154(b) by 0 days.

(21) Appl. No.: 15/927,920

(22) Filed: Mar. 21, 2018

(65) Prior Publication Data
US 2018/0208582 A1    Jul. 26, 2018

Related U.S. Application Data

(62) Division of application No. 15/624,566, filed on Jun. 15, 2017, now abandoned.

(60) Provisional application No. 62/510,711, filed on May 24, 2017, provisional application No. 62/476,581, filed on Mar. 24, 2017, provisional application No. 62/417,151, filed on Nov. 3, 2016, provisional application No. 62/350,876, filed on Jun. 16, 2016.

(51) Int. Cl.
| *C07D 403/12* | (2006.01) |
| *C07D 401/14* | (2006.01) |
| *C07D 413/14* | (2006.01) |
| *C07D 417/14* | (2006.01) |
| *C07D 491/20* | (2006.01) |
| *C07D 498/04* | (2006.01) |
| *C07B 59/00* | (2006.01) |
| *C07D 403/14* | (2006.01) |
| *C07D 405/14* | (2006.01) |
| *C07D 409/14* | (2006.01) |
| *C07D 487/04* | (2006.01) |

(52) U.S. Cl.
CPC .......... *C07D 403/12* (2013.01); *C07B 59/002* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 487/04* (2013.01); *C07D 491/20* (2013.01); *C07D 498/04* (2013.01); *C07B 2200/05* (2013.01)

(58) Field of Classification Search
CPC ........................... C07D 403/12; C07D 405/14
See application file for complete search history.

(56) References Cited

U.S. PATENT DOCUMENTS

| 7,144,911 | B2 | 12/2006 | Flynn et al. |
| 8,815,882 | B2 | 8/2014 | Baker-Glenn et al. |
| 9,676,792 | B2 | 6/2017 | Gray et al. |
| 9,932,325 | B2 * | 4/2018 | Estrada ................ C07B 59/002 |
| 2009/0105266 | A1 | 4/2009 | Glatthar et al. |
| 2013/0079324 | A1 | 3/2013 | Cheng et al. |
| 2013/0267513 | A1 | 10/2013 | Chan et al. |
| 2015/0051238 | A1 | 2/2015 | Baker-Glenn et al. |
| 2017/0362206 | A1 | 12/2017 | Estrada et al. |
| 2018/0327391 | A1 | 11/2018 | Estrada et al. |

FOREIGN PATENT DOCUMENTS

| CN | 105461694 | 4/2016 |
| WO | WO-2000/039108 | 7/2000 |
| WO | WO-2003/076658 | 9/2003 |
| WO | WO-2004/060306 | 7/2004 |
| WO | WO-2005/086656 | 9/2005 |
| WO | WO-2006/014290 | 2/2006 |
| WO | WO-2007/009524 | 1/2007 |
| WO | WO-2007/117995 | 10/2007 |
| WO | WO-2007/149798 | 12/2007 |
| WO | WO-2008/118822 | 10/2008 |
| WO | WO-2008/128968 | 10/2008 |
| WO | WO-2008/137619 | 11/2008 |
| WO | WO-2008/147626 | 12/2008 |
| WO | WO-2009/032694 | 3/2009 |
| WO | WO-2009/127642 | 10/2009 |
| WO | WO-2010/101973 | 9/2010 |
| WO | WO-2010/111406 | 9/2010 |
| WO | WO-2011/060295 | 5/2011 |
| WO | WO-2011/151360 | 12/2011 |
| WO | WO-2012/058193 | 5/2012 |
| WO | WO-2012/062783 | 5/2012 |
| WO | WO-2012/075046 | 6/2012 |
| WO | WO-2012/174338 | 12/2012 |

(Continued)

OTHER PUBLICATIONS

Chan et al., "Discovery of a Highly Selective, Brain-Penetrant Aminopyrazole LRRK2 Inhibitor", ACS Medicinal Chemistry Letters, 2013, 4(1), 85-90.

Estrada et al., "Discovery of Highly Potent, Selective, and Brain-Penetrant Aminopyrazole Leucine-Rich Repeat Kinase 2 (LRRK2) Small Molecule Inhibitors", Journal of Medicinal Chemistry, 2014, 57(3), 921-936.

(Continued)

*Primary Examiner* — Golam M Shameem

(74) *Attorney, Agent, or Firm* — Sheppard Mullin Richter & Hampton LLP

(57) ABSTRACT

The present disclosure relates generally to LRRK2 inhibitors, or a pharmaceutically acceptable salt, deuterated analog, prodrug, tautomer, stereoisomer, or mixture of stereoisomers thereof, and methods of making and using thereof.

27 Claims, No Drawings

(56) References Cited

FOREIGN PATENT DOCUMENTS

| WO | WO-2013/014162 | 1/2013 |
|----|----------------|--------|
| WO | WO-2013/079493 | 6/2013 |
| WO | WO-2013/079494 | 6/2013 |
| WO | WO-2013/079495 | 6/2013 |
| WO | WO-2013/079496 | 6/2013 |
| WO | WO-2013/079505 | 6/2013 |
| WO | WO-2013/126283 | 8/2013 |
| WO | WO-2013/130976 | 9/2013 |
| WO | WO-2013/164321 | 11/2013 |
| WO | WO-2013/164323 | 11/2013 |
| WO | WO-2014/116772 | 7/2014 |
| WO | WO-2014/130241 | 8/2014 |
| WO | WO-2014/135245 | 9/2014 |
| WO | WO-2014/150981 | 9/2014 |
| WO | WO-2014/181137 | 11/2014 |
| WO | WO-2014/181287 | 11/2014 |
| WO | WO-2015/113452 | 8/2015 |
| WO | WO-2015/131005 | 9/2015 |
| WO | WO-2015/148867 | 10/2015 |
| WO | WO-2015/148869 | 10/2015 |
| WO | WO 2016/149311 | 9/2016 |
| WO | WO-2016/201370 | 12/2016 |
| WO | WO-2017/046675 | 3/2017 |
| WO | WO-2017/087282 | 5/2017 |
| WO | WO-2017/087905 | 5/2017 |
| WO | WO-2017/089390 | 6/2017 |
| WO | WO-2017/100703 | 6/2017 |
| WO | WO-2017/106771 | 6/2017 |
| WO | WO-2017/156493 | 9/2017 |
| WO | WO-2018/217946 | 11/2018 |

OTHER PUBLICATIONS

International Search Report and Written Opinion for International Application No. PCT/US2017/037782 dated Oct. 4, 2017, 20 pages.
Invitation to Pay Additional Fees and, Where Applicable, Protest Fee for PCT/US2017/037782 dated Jul. 31, 2017, 16 pages.

* cited by examiner

COMPOUNDS, COMPOSITIONS, AND METHODS

CROSS REFERENCE TO RELATED APPLICATIONS

This application is a divisional of U.S. application Ser. No. 15/624,566, filed Jun. 15, 2017, which claims the benefit under 35 U.S.C. § 119(e) to U.S. Provisional Application Nos. 62/350,876 filed Jun. 16, 2016, 62/417,151 filed Nov. 3, 2016, 62/476,581 filed Mar. 24, 2017, and 62/510,711 filed May 24, 2017, and all of which are incorporated by reference.

FIELD

The present disclosure relates generally to novel heteroaryl-substituted pyrimidines and their use as therapeutic agents, for example, as inhibitors of LRRK2.

BACKGROUND

Neurodegenerative diseases, such as Parkinson's disease, amyotrophic lateral sclerosis (ALS), Alzheimer's disease, Lewy body dementia, and Huntington's disease affect millions of people. Parkinson's disease is a chronic, progressive motor system disorder characterized by selective degeneration and cell death of dopaminergic neurons in the substantial nigra region of the brain. This leaves patients with impaired ability to direct and control their movements. The cause of the disease was generally considered to be sporadic and unknown, but significant advancements in understanding have been made in the last 15 years.

The genetic basis for the disease and associated pathogenic mechanisms have led exploration of the gene encoding leucine-rich repeat kinase 2 (LRRK2) protein and its association with hereditary Parkinson's disease (Paisan-Ruiz et al., Neuron, Vol. 44(4), 2004, 601-607). LRRK2 is a member of the ROCO protein family and shares five conserved domains with all other family members. Many mis-sense mutations to the LRRK2 gene have been linked with autosomal dominant Parkinson's disease in familial studies (Trinh and Farrar, Nature Reviews in Neurology, Vol. 9, 2013, 445-454; Paisan-Ruiz et al., J. Parkinson's Disease, Vol. 3, 2013, 85-103). The most common pathogenic mutation, G2019S, occurs in the highly conserved kinase domain of LRRK2 (See Gilks et al., Lancet, Vol 365, 2005, 415-416). In vitro studies indicate Parkinson's disease-associated mutation leads to increased LRRK2 activity and a decreased rate of GTP hydrolysis (Guo et al., Experimental Cell Research, Vol. 313(16), 2007, 3658-3670). This evidence suggests the kinase and GTPase activities of LRRK2 are important for pathogenesis and the LRRK2 kinase domain may regulate overall LRRK2 function (See Cookson, Nat. Rev. Neurosci., Vol. 11, 2010, 791-797).

While progress has been made in this field, there remains a need for improved inhibitors of the LRRK2 receptor which are useful for treatment of various neurodegenerative diseases, such as Parkinson's disease, Alzheimer's disease and amyotrophic lateral sclerosis.

DESCRIPTION

Provided herein are compounds that are useful as inhibitors of LRRK2. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by LRRK2. Moreover, the disclosure provides uses of the compounds or compositions thereof in the manufacture of a medicament for the treatment of a disease, disorder, or condition that is mediated, at least in part, by LRRK2.

In one embodiment, provided is a compound of formula I:

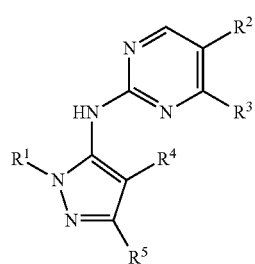

or a pharmaceutically acceptable salt, deuterated analog, prodrug, stereoisomer, or a mixture of stereoisomers thereof, wherein:

$R^1$ is optionally substituted cycloalkyl or, when $R^5$ is $-CR^{5a}R^6R^7$ where $R^{5a}$ is optionally substituted triazol-2-yl, $R^1$ is optionally substituted cycloalkyl or $C_{1-6}$ alkyl optionally substituted with halo;

$R^2$ is halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, $-C(O)R^{10}$, or $-C(O)N(R^{11})(R^{12})$;

$R^3$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or $-N(R^{11})(R^{12})$;

$R^4$ is hydrogen or halo;

$R^5$ is hydrogen, halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted heterocyclyl, optionally substituted heteroaryl, optionally substituted $C_{1-6}$ alkylthio, optionally substituted $C_{1-6}$ alkylsulfonyl, $-C(O)R^{10}$, or $-C(O)N(R^{11})(R^{12})$;

$R^6$ and $R^7$ are each independently H or optionally substituted $C_{1-6}$ alkyl;

each $R^{10}$ is independently optionally substituted $C_{1-6}$ alkyl or optionally substituted $C_{1-6}$ alkoxy; and $R^{11}$ and $R^{12}$ are each independently hydrogen, optionally substituted $C_{1-6}$ alkyl, optionally substituted cycloalkyl, or $R^{11}$ and $R^{12}$ together form an optionally substituted heterocyclyl group.

In one embodiment, provided is a compound of formula II:

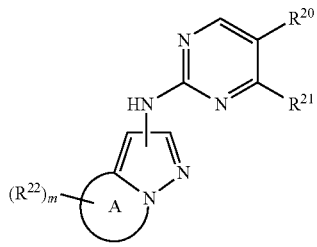

or a pharmaceutically acceptable salt, deuterated analog, prodrug, stereoisomer, or a mixture of stereoisomers thereof, wherein:

$R^{20}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{23}$;

$R^{21}$ is optionally substituted cycloalkyl, heteroaryl, $C_{1-6}$ alkoxy, —S—$C_{1-6}$ alkyl, or —N($R^{24}$)($R^{25}$);

m is 0, 1, 2, 3, or 4;

each $R^{22}$ is independently halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, or —C(O)$R^{26}$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted; or two $R^{22}$ together with the atom to which they are attached form a cycloalkyl or heterocyclyl, wherein each cycloalkyl and heterocyclyl is optionally substituted;

$R^{23}$ is $C_{1-6}$ alkyl, $C_{1-6}$ alkoxy, —N($R^{27}$)$_2$, or heterocyclyl, wherein each $C_{1-6}$ alkyl, $C_{1-6}$ alkoxy and heterocyclyl is optionally substituted;

$R^{24}$ and $R^{25}$ are each independently hydrogen or optionally substituted $C_{1-6}$ alkyl; or $R^{24}$ and $R^{25}$ together with the atom to which they are attached form an optionally substituted heterocyclyl;

$R^{26}$ is $C_{1-6}$ alkyl or heterocyclyl, wherein $C_{1-6}$ alkyl, $C_{1-6}$ haloalkyl, and heterocyclyl is independently optionally substituted with one or more substituents selected from halo, cyano, hydroxy, $C_{1-6}$ alkoxy, and $C_{1-6}$ alkylsulfonyl;

each $R^{27}$ is independently H or optionally substituted $C_{1-6}$ alkyl;

and A is a heterocyclyl or heteroaryl ring fused to the pyrazole.

In some embodiments, the compound is in Table 1A, 1B, 2A or 2B, or is a pharmaceutically acceptable salt, deuterated analog, prodrug, tautomer, stereoisomer, or a mixture of stereoisomers thereof.

In another embodiment, provided is a pharmaceutical composition comprising a compound as shown in Table 1A, 1B, 2A or 2B, or a pharmaceutically acceptable salt, deuterated analog, prodrug, tautomer, stereoisomer, or a mixture of stereoisomers thereof, and a pharmaceutically acceptable carrier, diluent, or excipient.

In another embodiment, provided is a method for treating a disease or condition mediated, at least in part, by LRRK2, the method comprising administering an effective amount of the pharmaceutical composition comprising a compound as shown in Table 1A or Table 1B, or a pharmaceutically acceptable salt, deuterated analog, prodrug, tautomer, stereoisomer, or a mixture of stereoisomers thereof, and a pharmaceutically acceptable carrier, diluent, or excipient, to a subject in need thereof.

In another embodiment, provided is a pharmaceutical composition comprising a compound as shown in Table 1A or Table 1B, or a pharmaceutically acceptable salt, deuterated analog, prodrug, tautomer, stereoisomer, or a mixture of stereoisomers thereof, and a pharmaceutically acceptable carrier, diluent, or excipient.

In another embodiment, provided is a method for treating a disease or condition mediated, at least in part, by LRRK2, the method comprising administering an effective amount of the pharmaceutical composition comprising a compound as shown in Table 1A or Table 1B, or a pharmaceutically acceptable salt, deuterated analog, prodrug, tautomer, stereoisomer, or a mixture of stereoisomers thereof, and a pharmaceutically acceptable carrier, diluent, or excipient, to a subject in need thereof. In another embodiment, provided is a method for treating a disease or condition mediated, at least in part, by LRRK2, the method comprising administering an effective amount of the pharmaceutical composition comprising a compound as shown in Table 1A, 1B, 2A or 2B, or a pharmaceutically acceptable salt, deuterated analog, prodrug, tautomer, stereoisomer, or a mixture of stereoisomers thereof, and a pharmaceutically acceptable carrier, diluent, or excipient, to a subject in need thereof.

The description herein sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy and 1,2-dimethylbutoxy.

"Alkoxyalkyl" refers to the group "alkyl-O-alkyl".

"Alkylthio" refers to the group "alkyl-S—".

"Alkylsulfinyl" refers to the group "alkyl-S(O)—".

"Alkylsulfonyl" refers to the group "alkyl-S(O)$_2$—".

"Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein, or R$^y$ and R$^z$ are taken together to form a cycloalkyl or heterocyclyl; each of which may be optionally substituted, as defined herein.

"Amidoalkyl" refers to an alkyl group as defined above, wherein one or more hydrogen atoms are replaced by an amido group.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aminoalkyl" refers to the group "-alkyl-NR$^y$R$^z$," wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —C(NR$^y$)(NR$^z_2$), wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused ring systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl, or heteroaryl; each of which may be optionally substituted, as defined herein.

"Cyanoalkyl" refers to refers to an alkyl group as defined above, wherein one or more hydrogen atoms are replaced by a cyano group.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e. the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5] undecanyl.

"Cycloalkoxy" refers to "—O-cycloalkyl."

"Cycloalkylalkyl" refers to the group "cycloalkyl-alkyl-."

"Cycloalkylalkoxy" refers to "—O-alkyl-cycloalkyl."

"Guanidino" refers to —NR$^y$C(=NR$^z$)(NR$^y$R$^z$), wherein each R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are ach independently hydrogen, alkyl, alkenyl, alkynyl, cycloalkyl, heterocyclyl, aryl, heteroalkyl, or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" refers to atoms occupying group VIIA of the periodic table, such as fluoro, chloro, bromo, or iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2, or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.), and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-."

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (=O) or N-oxide (—O$^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e. thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-".

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethylbenzene)sulfonyloxy, (4-tert-butyl-benzene)sulfonyloxy, benzenesulfonyloxy, (4-methoxy-benzene)sulfonyloxy, and the like.

"Oxime" refers to the group —$CR^y$(=NOH) wherein $R^y$ is hydrogen, alkyl, alkenyl, alkynyl, cycloalkyl, heterocyclyl, aryl, heteroalkyl, or heteroaryl; each of which may be optionally substituted, as defined herein.

"Sulfonyl" refers to the group —$S(O)_2R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —$S(O)R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" used herein means any of the above groups (e.g., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —$Si(R^y)_3$ wherein each $R^y$ is independently hydrogen, alkyl, alkenyl, alkynyl, heteroalkyl, cycloalkyl, aryl, heteroaryl, or heterocyclyl.

In one embodiment, "substituted" includes any of the above groups (e.g., alkyl, alkenyl, alkynyl, alkylene, alkoxy, haloalkyl, haloalkoxy, cycloalkyl, aryl, heterocyclyl, heteroaryl, and/or heteroalkyl) in which one or more hydrogen atoms are replaced with —$NR^gR^h$, —$NR^gC(=O)R^h$, —$NR^gC(=O)NR^gR^h$, —$NR^gC(=O)OR^h$, —$NR^gSO_2R^h$, —$OC(=O)NR^gR^h$, —$OR^g$, —$SR^g$, —$SOR^g$, —$SO_2R^g$, —$OSO_2R^g$, —$SO_2OR^g$, =$NSO_2R^g$, and —$SO_2NR^gR^h$. "Substituted" also means any of the above groups in which one or more hydrogen atoms are replaced with —$C(=O)R^g$, —$C(=O)OR^g$, —$C(=O)NR^gR^h$, —$CH_2SO_2R^g$, —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In addition, each of the foregoing substituents may also be optionally substituted with one or more of the above substituents.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxy, halo, alkoxy, acyl, oxo, amino, cycloalkyl, heterocyclyl, aryl and heteroaryl. In other embodiments, the one or more substituents may be further substituted with halo, alkyl, haloalkyl, hydroxy, alkoxy, cycloalkyl, heterocyclyl, aryl, or heteroaryl, each of which is substituted. In other embodiments, the substituents may be further substituted with halo, alkyl, haloalkyl, alkoxy, hydroxy, cycloalkyl, heterocyclyl, aryl, or heteroaryl, each of which is unsubstituted.

Any compound or structure given herein, is also intended to represent unlabeled forms as well as isotopically labeled forms of the compounds. Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), di(substituted alkyl) amines (i.e., N(substituted alkyl)$_3$), alkenyl amines (i.e., $NH_2$(alkenyl)), dialkenyl amines (i.e., HN(alkenyl)$_2$), dialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), di(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

2. Compounds

Provided herein are compounds that are useful as inhibitors of LRRK2.

In one embodiment, provided is a compound of formula I:

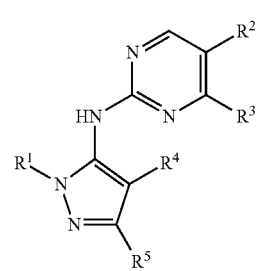

or a pharmaceutically acceptable salt, deuterated analog, prodrug, stereoisomer, or a mixture of stereoisomers thereof, wherein:

$R^1$ is optionally substituted cycloalkyl or, when $R^5$ is —$CR^{5a}R^6R^7$ where $R^{5a}$ is optionally substituted triazol-2-yl, $R^1$ is optionally substituted cycloalkyl or $C_{1-6}$ alkyl optionally substituted with halo;

$R^2$ is halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —$C(O)R^{10}$, or —$C(O)N(R^{11})(R^{12})$;

$R^3$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —$N(R^{11})(R^{12})$;

$R^4$ is hydrogen or halo;

$R^5$ is hydrogen, halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted heterocyclyl, optionally substituted heteroaryl, optionally substituted $C_{1-6}$ alkylthio, optionally substituted $C_{1-6}$ alkylsulfonyl, —$C(O)R^{10}$, or —$C(O)N(R^{11})(R^{12})$;

$R^6$ and $R^7$ are each independently H or optionally substituted $C_{1-6}$ alkyl;

each $R^{10}$ is independently optionally substituted $C_{1-6}$ alkyl or optionally substituted $C_{1-6}$ alkoxy; and $R^{11}$ and $R^{12}$ are each independently hydrogen, optionally substituted $C_{1-6}$ alkyl, optionally substituted cycloalkyl, or $R^{11}$ and $R^{12}$ together form an optionally substituted heterocyclyl group.

In one embodiment, provided is a compound of formula I represented by formula Ia:

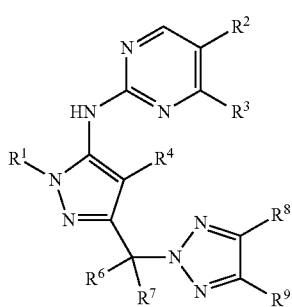

or a pharmaceutically acceptable salt, deuterated analog, prodrug, stereoisomer, or a mixture of stereoisomers thereof, wherein $R^2$, $R^3$ and $R^4$ are as defined herein, and:

$R^1$ is optionally substituted cycloalkyl or $C_{1-6}$ alkyl optionally substituted with halo;

$R^6$ and $R^7$ are each independently hydrogen or $C_{1-6}$ alkyl optionally substituted with halo; and $R^8$ and $R^9$ are each independently hydrogen, cyano, halo, optionally substituted $C_{1-6}$ alkyl, optionally substituted $C_{1-6}$ alkoxy, or optionally substituted heteroaryl.

In certain embodiments, $R^6$ and $R^7$ are methyl.

In certain embodiments, $R^8$ and $R^9$ are hydrogen.

In certain embodiments, at least one of $R^8$ and $R^9$ is hydrogen.

In certain embodiments, $R^1$ is optionally substituted cyclopropyl or optionally substituted cyclobutyl.

In certain embodiments, $R^1$ is cycloalkyl independently substituted with one or more halo, hydroxy, cyano, or heteroaryl.

In certain embodiments, $R^1$ is cyclopropyl, cyclobutyl, hydroxycylobut-3-yl, cyanocylobut-3-yl, triazol-2yl-cyclobut-3-yl, triazol-1-yl-cyclobut-3-yl, or fluorocyclobut-3-yl.

In certain embodiments, $R^1$ is $CD_3$, ethyl, or prop-2-yl.

In certain embodiments, $R^2$ is halo, cyano, $C_{1-6}$ alkyl optionally substituted with halo.

In certain embodiments, $R^2$ is bromo.

In certain embodiments, $R^2$ is —$CF_3$.

In certain embodiments, $R^3$ is optionally substituted cycloalkyl, optionally substituted $C_{1-6}$ alkoxy, or —N($R^{11}$)($R^{12}$).

In certain embodiments, $R^3$ is cyclopropyl, methoxy, 1,1-difluoroeth-2-ylamino, cyclopropylamino, —NH($CH_3$), or —NH($CH_2CH_3$).

In certain embodiments, $R^4$ is hydrogen.

In certain embodiments, $R^5$ is cyano, optionally substituted $C_{1-6}$ alkyl, optionally substituted cycloalkyl, optionally substituted heterocyclyl, optionally substituted heteroaryl, optionally substituted $C_{1-6}$ alkylsulfonyl, —C(O)$R^{10}$, or —C(O)N($R^{11}$)($R^{12}$).

In certain embodiments, $R^5$ is cyano, —C(O)$R^{10}$, —C(O)N($R^{11}$)($R^{12}$), $C_{1-6}$ alkylsulfonyl, acyl, heteroaryl optionally substituted with $C_{1-6}$ alkyl, cycloalkyl optionally substituted with one to three oxo or $C_{1-6}$ alkyl, heterocyclyl optionally substituted with one to three halo, $C_{1-6}$ alkyl, $C_{1-6}$ alkyl substituted with cyano, hydroxyl, alkylsulfonyl, heterocyclyl, hydroxy, alkoxy, or heteroaryl, or $C_{1-6}$ cycloalkyl substituted with cyano, aminocarbonyl, or alkoxycarbonyl.

In certain embodiments, $R^5$ is cyano, —C(O)$R^{10}$, —C(O)N($R^{11}$)($R^{12}$), $C_{1-6}$ alkylsulfonyl, acyl, heteroaryl optionally substituted with $C_{1-6}$ alkyl, heterocyclyl optionally substituted with $C_{1-6}$ alkyl, $C_{1-6}$ alkyl substituted with cyano, hydroxyl, alkylsulfonyl, heterocyclyl, hydroxy, alkoxy, or heteroaryl, or $C_{1-6}$ cycloalkyl substituted with cyano, aminocarbonyl, or alkoxycarbonyl.

In certain embodiments, $R^5$ is 2-(triazol-2-yl)propan-2-yl, 2-pyrimidin-2-ylpropan-2-yl, N,N-dimethylamido, 2-methylpropan-2-yl, methylsulfonyl, cyano, 2-hydroxypropan-2-yl, methylcarbonyl, 5-methylpyrrolidin-2-one-5-yl, 1-(triazol-2-yl)ethyl, 2-methylsulfonylpropan-2-yl, 5-methyl-1,3-oxazol-4-yl)pyrazol-3-yl, 3-methyloxetan-3-yl, 1-cyano-cycloprop-2-yl, pyrrolidin-2-one-5-yl, 1,1-dioxo-1,2-thiazolidin-2-yl, 7-methyl-5,6-dihydropyrrolo[1,2-a]imidazol-7-yl, 1-ethoxycarbonyl-cycloprop-2-yl, 1-aminocarbonyl-cycloprop-2-yl, 7-methyl-5,6-dihydropyrrolo[1,2-b][1,2,4]triazol-7-yl, 2-methoxypropan-2-yl, 2-cyanopropan-2-yl, 3-methyloxolan-2-one-3-yl, oxabicyclo[3.1.0]hexan-2-one-3-yl, 1-methyl-pyrrolidin-2-one-yl, cyclopropyl, 1-ethyl-4,4-difluoropiperid-3-yl, 4,4-difluoropiperid-3-yl, or 2-methyl-1-oxo-cyclopent-2-yl. In certain embodiments, $R^5$ is 2-(triazol-2-yl)propan-2-yl, 2-pyrimidin-2-ylpropan-2-yl, N,N-dimethylamido, 2-methylpropan-2-yl, methylsulfonyl, cyano, 2-hydroxypropan-2-yl, methylcarbonyl, 5-methylpyrrolidin-2-one-5-yl, 1-(triazol-2-yl)ethyl, 2-methylsulfonylpropan-2-yl, 5-methyl-1,3-oxazol-4-yl)pyrazol-3-yl, 3-methyloxetan-3-yl, 1-cyano-cycloprop-2-yl, pyrrolidin-2-one-5-yl, 1,1-dioxo-1,2-thiazolidin-2-yl, 7-methyl-5,6-dihydropyrrolo[1,2-a]imidazol-7-yl, 1-ethoxycarbonyl-cycloprop-2-yl, 1-aminocarbonyl-cycloprop-2-yl, 7-methyl-5,6-dihydropyrrolo[1,2-b][1,2,4]triazol-7-yl, 2-methoxypropan-2-yl, 2-cyanopropan-2-yl, 3-methyloxolan-2-one-3-yl, oxabicyclo[3.1.0]hexan-2-one-3-yl, or 1-methyl-pyrrolidin-2-one-yl.

In certain embodiments, $R^1$ is cycloalkyl independently substituted with one or more hydroxy, cyano, or heteroaryl; $R^2$ is halo or $C_{1-6}$ fluoroalkyl; $R^3$ is —N($R^{11}$)($R^{12}$) or $C_{1-6}$ alkoxy; and $R^4$ is hydrogen.

In certain embodiments, certain compounds provided herein are surprisingly brain penetrant. In certain embodiments, the compounds further have an MDR1-MDCK efflux ratio of less than or equal to about five. In certain embodiments, these compounds are of formula Ia or Ib.

In one embodiment, provided is a compound of formula I represented by formula Ib:

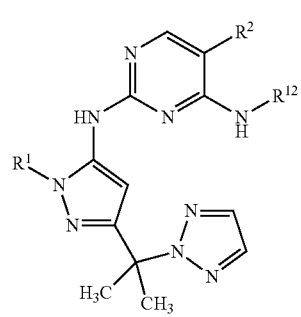

or a pharmaceutically acceptable salt, deuterated analog, prodrug, stereoisomer, or a mixture of stereoisomers thereof, wherein:

$R^1$ is optionally substituted cycloalkyl or $C_{1-6}$ alkyl optionally substituted with halo;

$R^2$ is halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —C(O)$R^{10}$, or —C(O)N($R^{11}$)($R^{12}$);

$R^{10}$ is optionally substituted $C_{1-6}$ alkyl or optionally substituted $C_{1-6}$ alkoxy; and each $R^{11}$ and $R^{12}$ are independently hydrogen, optionally substituted $C_{1-6}$ alkyl, optionally substituted cycloalkyl, or $R^{11}$ and $R^{12}$ together form an optionally substituted heterocyclyl group.

In certain embodiments, $R^1$ is optionally substituted cyclopropyl.

In certain embodiments, $R^1$ is cyclopropyl.

In certain embodiments, $R^1$ is methyl optionally substituted with halo.

In certain embodiments, $R^1$ is —CD$_3$.

In certain embodiments, $R^1$ is —CF$_3$.

In certain embodiments, $R^2$ is halo, cyano, or $C_{1-6}$ alkyl optionally substituted with halo.

In certain embodiments, $R^2$ is bromo.

In certain embodiments, $R^2$ is —CF$_3$.

In certain embodiments, $R^{12}$ is optionally substituted $C_{1-6}$ alkyl.

In certain embodiments, $R^{12}$ is ethyl.

In certain embodiments, $R^1$ is optionally substituted cyclopropyl or methyl optionally substituted with halo; $R^2$ is halo, cyano, or $C_{1-6}$ alkyl optionally substituted with halo; and $R^{12}$ is optionally substituted $C_{1-6}$ alkyl.

In one embodiment, provided is a compound of formula II:

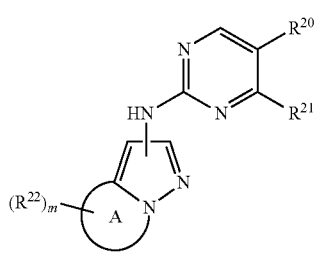

II or a pharmaceutically acceptable salt, deuterated analog, prodrug, stereoisomer, or a mixture of stereoisomers thereof, wherein:

$R^{20}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{23}$;

$R^{21}$ is optionally substituted cycloalkyl, heteroaryl, $C_{1-6}$ alkoxy, —S—$C_{1-6}$ alkyl, or —N($R^{24}$)($R^{25}$);

m is 0, 1, 2, 3, or 4;

each $R^{22}$ is independently halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, or —C(O)$R^{26}$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted; or two $R^{22}$ together with the atom to which they are attached form a cycloalkyl or heterocyclyl, wherein each cycloalkyl and heterocyclyl is optionally substituted;

$R^{23}$ is $C_{1-6}$ alkyl, $C_{1-6}$ alkoxy, —N($R^{27}$)$_2$, or heterocyclyl, wherein each $C_{1-6}$ alkyl, $C_{1-6}$ alkoxy and heterocyclyl is optionally substituted;

$R^{24}$ and $R^{25}$ are each independently H or optionally substituted $C_{1-6}$ alkyl; or $R^{24}$ and $R^{25}$ together with the atom to which they are attached form an optionally substituted heterocyclyl;

$R^{26}$ is $C_{1-6}$ alkyl or heterocyclyl, wherein $C_{1-6}$ alkyl, $C_{1-6}$ haloalkyl, and heterocyclyl is independently optionally substituted with one or more substituents selected from halo, cyano, hydroxy, $C_{1-6}$ alkoxy, and $C_{1-6}$ alkylsulfonyl;

each $R^{27}$ is independently H or optionally substituted $C_{1-6}$ alkyl; and

A is a heterocyclyl or heteroaryl ring fused to the pyrazole.

In one embodiment, ring A contains additional heteroatoms. In one embodiment, ring A contains only the bridgehead nitrogen shared with the pyrazole ring.

In one embodiment, provided is a compound of formula IIA:

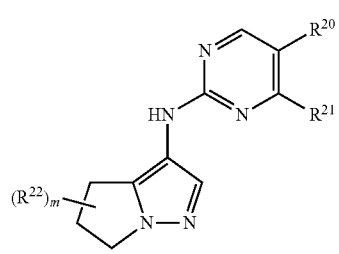

IIA or a pharmaceutically acceptable salt, deuterated analog, prodrug, stereoisomer, or a mixture of stereoisomers thereof, wherein $R^{20}$, $R^{21}$, $R^{22}$ and m are as defined herein.

In one embodiment, provided is a compound of formula IIB:

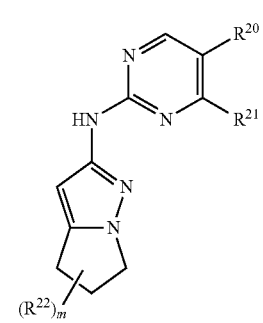

IIB or a pharmaceutically acceptable salt, deuterated analog, prodrug, stereoisomer, or a mixture of stereoisomers thereof, wherein $R^{20}$, $R^{21}$, $R^{22}$ and m are as defined herein.

In one embodiment, provided is a compound of formula IIA-a:

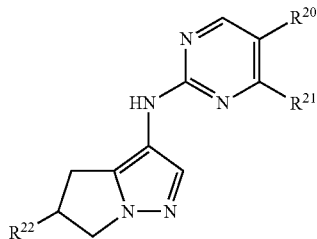

or a pharmaceutically acceptable salt, deuterated analog, prodrug, stereoisomer, or a mixture of stereoisomers thereof, wherein $R^{20}$, $R^{21}$, $R^{22}$ and m are as defined herein.

In one embodiment, provided is a compound of formula IIA-b:

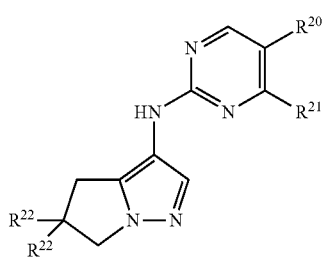

or a pharmaceutically acceptable salt, deuterated analog, prodrug, stereoisomer, or a mixture of stereoisomers thereof, wherein $R^{20}$, $R^{21}$, $R^{22}$ and m are as defined herein.

In certain embodiments, $R^{20}$ is halo, cyano, $C_{1-6}$ alkyl, or $C_{1-6}$ haloalkyl. In certain embodiments, $R^{20}$ is $C_{1-6}$ haloalkyl. In certain embodiments, $R^{20}$ is $C_{1-6}$ haloalkyl.

In certain embodiments, $R^{21}$ is optionally substituted cycloalkyl or —N($R^{24}$)($R^{25}$). In certain embodiments, $R^{21}$ is optionally substituted cycloalkyl, $C_{1-6}$ alkoxy or —N($R^{24}$)($R^{25}$).

In certain embodiments, $R^{22}$ is independently halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, or —C(O)$R^{26}$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted.

In certain embodiments, $R^{22}$ is independently halo, cyano, $C_{1-6}$ alkyl, or heteroaryl.

In certain embodiments, two $R^{22}$ together with the atom to which they are attached form a cycloalkyl or heterocyclyl, wherein each cycloalkyl and heterocyclyl is optionally substituted. In certain embodiments, two $R^{22}$ together with the atom to which they are attached form a heterocyclyl.

In one embodiment, provided is a compound of formula III:

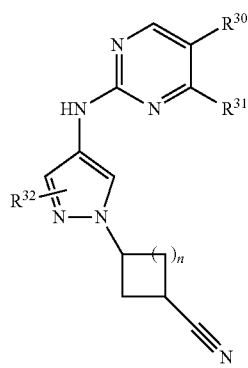

or a pharmaceutically acceptable salt, deuterated analog, prodrug, stereoisomer, or a mixture of stereoisomers thereof, wherein:

n is 0 or 1;

$R^{30}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{33}$;

$R^{31}$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{35}$)($R^{36}$);

$R^{32}$ is hydrogen, halo, cyano, optionally substituted $C_{1-6}$ alkyl, optionally substituted $C_{1-6}$ alkenyl, optionally substituted $C_{1-6}$ alkynyl, optionally substituted $C_{1-6}$ haloalkyl, optionally substituted $C_{1-6}$ alkoxy, optionally substituted $C_{1-6}$ haloalkoxy, optionally substituted cycloalkyl, optionally substituted heterocyclyl, optionally substituted heteroaryl, optionally substituted $C_{1-6}$ alkylthio, optionally substituted $C_{1-6}$ alkylsulfonyl, —C(O)$R^{34}$, or —C(O)N($R^{35}$)($R^{36}$);

$R^{33}$ is $C_{1-6}$ alkyl, $C_{1-6}$ alkoxy, —N($R^{35}$)($R^{36}$), or heterocyclyl, wherein each $C_{1-6}$ alkyl, $C_{1-6}$ alkoxy, and heterocyclyl is optionally substituted;

$R^{34}$ is optionally substituted $C_{1-6}$ alkyl or optionally substituted $C_{1-6}$ alkoxy; and $R^{35}$ and $R^{36}$ are each independently hydrogen, optionally substituted $C_{1-6}$ alkyl, optionally substituted cycloalkyl, or $R^{35}$ and $R^{36}$ together form an optionally substituted heterocyclyl group.

In one embodiment, provided is a compound of formula IIIA:

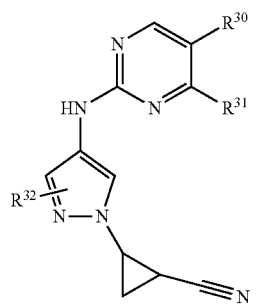

or a pharmaceutically acceptable salt, deuterated analog, prodrug, stereoisomer, or a mixture of stereoisomers thereof, wherein:

$R^{30}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{33}$;

$R^{31}$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{35}$)($R^{36}$);

$R^{32}$ is hydrogen, halo, cyano, optionally substituted $C_{1-6}$ alkyl, optionally substituted $C_{1-6}$ alkenyl, optionally substituted $C_{1-6}$ alkynyl, optionally substituted $C_{1-6}$ haloalkyl, optionally substituted $C_{1-6}$ alkoxy, optionally substituted $C_{1-6}$ haloalkoxy, optionally substituted cycloalkyl, optionally substituted heterocyclyl, optionally substituted heteroaryl, optionally substituted $C_{1-6}$ alkylthio, optionally substituted $C_{1-6}$ alkylsulfonyl, —C(O)$R^{34}$, or —C(O)N($R^{35}$)($R^{36}$);

$R^{33}$ is $C_{1-6}$ alkyl, $C_{1-6}$ alkoxy, —N($R^{35}$)($R^{36}$), or heterocyclyl, wherein each $C_{1-6}$ alkyl, $C_{1-6}$ alkoxy, and heterocyclyl is optionally substituted;

$R^{34}$ is optionally substituted $C_{1-6}$ alkyl or optionally substituted $C_{1-6}$ alkoxy; $R^{35}$ and $R^{36}$ are each independently hydrogen, optionally substituted $C_{1-6}$ alkyl, optionally substituted cycloalkyl, or $R^{35}$ and $R^{36}$ together form an optionally substituted heterocyclyl group.

In one embodiment, provided is a compound of formula IIIB:

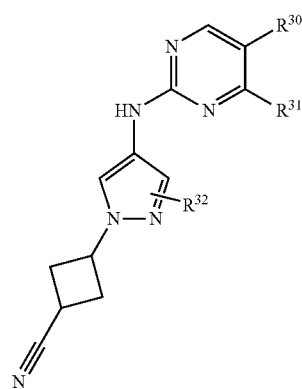

IIIB or a pharmaceutically acceptable salt, deuterated analog, prodrug, stereoisomer, or a mixture of stereoisomers thereof, wherein:

$R^{30}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{33}$;

$R^{31}$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{35}$)($R^{36}$);

$R^{32}$ is hydrogen, halo, cyano, optionally substituted $C_{1-6}$ alkyl, optionally substituted $C_{1-6}$ alkenyl, optionally substituted $C_{1-6}$ alkynyl, optionally substituted $C_{1-6}$ haloalkyl, optionally substituted $C_{1-6}$ alkoxy, optionally substituted $C_{1-6}$ haloalkoxy, optionally substituted cycloalkyl, optionally substituted heterocyclyl, optionally substituted heteroaryl, optionally substituted $C_{1-6}$ alkylthio, optionally substituted $C_{1-6}$ alkylsulfonyl, —C(O)$R^{34}$, or —C(O)N($R^{35}$)($R^{36}$);

$R^{33}$ is $C_{1-6}$ alkyl, $C_{1-6}$ alkoxy, —N($R^{35}$)($R^{36}$), or heterocyclyl, wherein each $C_{1-6}$ alkyl, $C_{1-6}$ alkoxy and heterocyclyl is optionally substituted;

$R^{34}$ is optionally substituted $C_{1-6}$ alkyl or optionally substituted $C_{1-6}$ alkoxy; and $R^{35}$ and $R^{36}$ are each independently hydrogen, optionally substituted $C_{1-6}$ alkyl, optionally substituted cycloalkyl, or $R^{35}$ and $R^{36}$ together form an optionally substituted heterocyclyl group.

In certain embodiments, $R^{30}$ is halo, cyano, $C_{1-6}$ alkyl, or $C_{1-6}$ haloalkyl. In certain embodiments, $R^{30}$ is $C_{1-6}$ haloalkyl.

In certain embodiments, $R^{31}$ is optionally substituted cycloalkyl, $C_{1-6}$ alkoxy or —N($R^{35}$)($R^{36}$). In certain embodiments, $R^{31}$ is optionally substituted cycloalkyl or —N($R^{35}$)($R^{36}$). In certain embodiments, $R^{31}$ is cycloalkyl or —N($R^{35}$)($R^{36}$). In certain embodiments, $R^{31}$ is —N($R^{35}$)($R^{36}$).

In certain embodiments, $R^{32}$ is hydrogen, halo, cyano, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, heterocyclyl, heteroaryl, $C_{1-6}$ alkylthio, $C_{1-6}$ alkylsulfonyl, —C(O)$R^{34}$, or —C(O)N($R^{35}$)($R^{36}$). In certain embodiments, $R^{32}$ is hydrogen, halo, cyano, optionally substituted $C_{1-6}$ alkyl, optionally substituted $C_{1-6}$ haloalkyl, optionally substituted $C_{1-6}$ alkoxy, or optionally substituted $C_{1-6}$ haloalkoxy. In certain embodiments, $R^{32}$ is hydrogen. In certain embodiments, $R^{32}$ is halo. In certain embodiments, $R^{32}$ is methyl.

In one embodiment, provided is a compound of formula IVA:

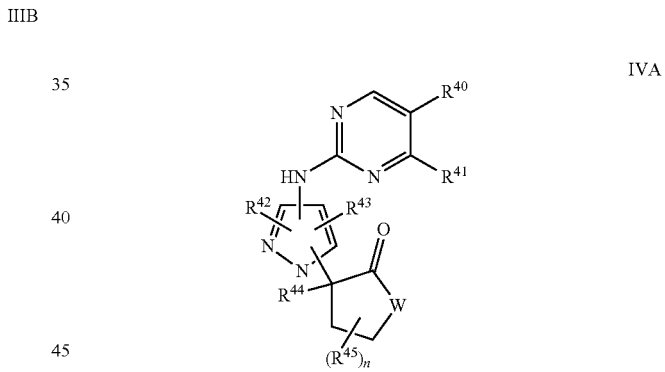

IVA or a pharmaceutically acceptable salt, deuterated analog, prodrug, stereoisomer, or a mixture of stereoisomers thereof, wherein:

W is O, C($R^{46}$)($R^{47}$) or N($R^{46}$);

$R^{40}$ is halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —C(O)$R^{48}$, or —C(O)N($R^{49}$)($R^{50}$);

$R^{41}$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{49}$)($R^{50}$);

$R^{42}$ is optionally substituted cycloalkyl or $C_{1-6}$ alkyl optionally substituted with halo;

$R^{43}$ is hydrogen or halo;

$R^{44}$ is H or $C_{1-3}$ alkyl optionally substituted with halo;

each $R^{45}$ independently is halo, oxo, or optionally substituted $C_{1-3}$ alkyl; n is 1, 2, 3, or 4;

$R^{46}$ and $R^{47}$ are independently H, halo, optionally substituted $C_{1-3}$ alkyl, optionally substituted cycloalkyl, or optionally substituted heterocyclyl;

$R^{48}$ is optionally substituted $C_{1-6}$ alkyl or optionally substituted $C_{1-6}$ alkoxy; and $R^{49}$ and $R^{50}$ are each independently hydrogen, optionally substituted $C_{1-6}$ alkyl, optionally substituted cycloalkyl, or $R^{49}$ and $R^{50}$ together form an optionally substituted heterocyclyl group.

In one embodiment, provided is a compound of formula IVA-a:

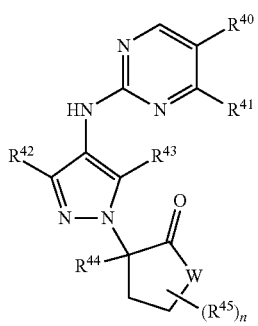

IVA-a or a pharmaceutically acceptable salt, deuterated analog, prodrug, stereoisomer, or a mixture of stereoisomers thereof, wherein W, $R^{43}$, $R^{44}$, $R^{45}$, and n are as defined herein, and:

$R^{40}$ is halo or $C_{1-6}$ haloalkyl;

$R^{41}$ is —$N(R^{49})(R^{50})$;

$R^{42}$ is optionally substituted cyclopropyl;

$R^{49}$ is hydrogen; and $R^{50}$ is optionally substituted $C_{1-6}$ alkyl.

In one embodiment, the compound is not 3-(4-((4-cyclopropyl-5-(trifluoromethyl)pyrimidin-2-yl)amino)-3-methyl-1H-pyrazol-1-yl)pyrrolidin-2-one, 3-(4-((4-cyclopropyl-5-(trifluoromethyl)pyrimidin-2-yl)amino)-5-methyl-1H-pyrazol-1-yl)-3-methylpyrrolidin-2-one, 3-(4-((4-cyclopropyl-5-(trifluoromethyl)pyrimidin-2-yl)amino)-5-methyl-1H-pyrazol-1-yl)pyrrolidin-2-one, or 3-(4-((4-cyclopropyl-5-(trifluoromethyl)pyrimidin-2-yl)amino)-3-methyl-1H-pyrazol-1-yl)-3-methylpyrrolidin-2-one, or a stereoisomer thereof.

In one embodiment, provided is a compound of formula IVA-b:

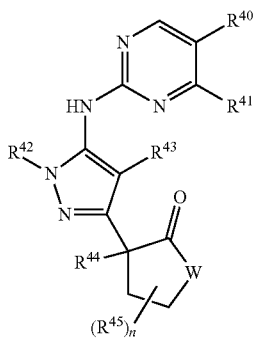

IVA-b or a pharmaceutically acceptable salt, deuterated analog, prodrug, stereoisomer, or a mixture of stereoisomers thereof, wherein W, $R^{43}$, $R^{44}$, $R^{45}$, and n are as defined herein, and:

$R^{40}$ is halo or $C_{1-6}$ haloalkyl;

$R^{41}$ is —$N(R^{49})(R^{50})$;

$R^{42}$ is optionally substituted cyclopropyl;

$R^{49}$ is hydrogen; and $R^{50}$ is optionally substituted $C_{1-6}$ alkyl.

In one embodiment, provided is a compound of formula IVB:

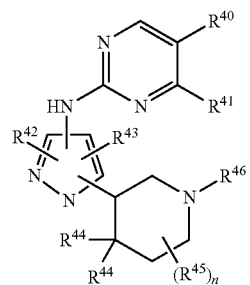

IVB or a pharmaceutically acceptable salt, deuterated analog, prodrug, stereoisomer, or a mixture of stereoisomers thereof, wherein:

$R^{40}$ is halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —$C(O)R^{48}$, or —$C(O)N(R^{49})(R^{50})$;

$R^{41}$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —$N(R^{49})(R^{50})$;

$R^{42}$ is optionally substituted cycloalkyl or $C_{1-6}$ alkyl optionally substituted with halo;

$R^{43}$ is hydrogen or halo;

each $R^{44}$ is independently H or $C_{1-3}$ alkyl optionally substituted with halo;

each $R^{45}$ independently is halo, oxo, or optionally substituted $C_{1-3}$ alkyl;

n is 1, 2, 3, or 4;

$R^{46}$ is H, halo, optionally substituted $C_{1-3}$ alkyl, optionally substituted cycloalkyl, or optionally substituted heterocyclyl;

$R^{48}$ is optionally substituted $C_{1-6}$ alkyl or optionally substituted $C_{1-6}$ alkoxy; and $R^{49}$ and $R^{50}$ are each independently hydrogen, optionally substituted $C_{1-6}$ alkyl, optionally substituted cycloalkyl, or $R^{49}$ and $R^{50}$ together form an optionally substituted heterocyclyl group.

In one embodiment, provided is a compound of formula IVB-a:

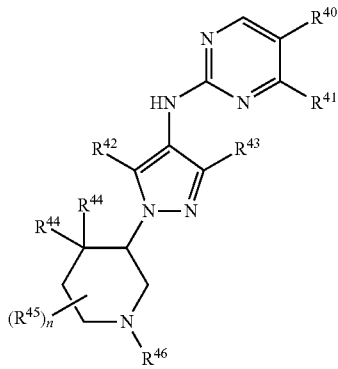

IVB-a or a pharmaceutically acceptable salt, deuterated analog, prodrug, stereoisomer, or a mixture of stereoisomers thereof, wherein $R^{43}$, $R^{44}$, $R^{45}$, $R^{46}$, and n are as defined herein, and:

$R^{40}$ is halo or $C_{1-6}$ haloalkyl;

$R^{41}$ is —N($R^{49}$)($R^{50}$);

$R^{42}$ is optionally substituted cyclopropyl;

$R^{49}$ is hydrogen; and $R^{50}$ is optionally substituted $C_{1-6}$ alkyl.

In one embodiment, the compound is not 5-(4-(4-(ethylamino)-5-(trifluoromethyl)pyrimidin-2-ylamino)-5-methyl-1H-pyrazol-1-yl)-1-methylpiperidin-2-one, 5-(4-(4-(ethylamino)-5-(trifluoromethyl)pyrimidin-2-ylamino)-3-methyl-1H-pyrazol-1-yl)-1-methylpiperidin-2-one, 5-(3-methyl-4-(4-(methylamino)-5-(trifluoromethyl)pyrimidin-2-ylamino)-1H-pyrazol-1-yl(piperidin-2-one, 5-(5-methyl-4-(4-(methylamino)-5-(trifluoromethyl)pyrimidin-2-ylamino)-1H-pyrazol-1-yl)piperidin-2-one, N4-ethyl-N$_2$-[5-methyl-1-((S)-1-oxetan-3-yl-piperidin-3-yl)-1H-pyrazol-4-yl]-5-trifluoromethyl-pyrimidine-2,4-diamine, N4-ethyl-N$_2$-[3-methyl-1-((S)-1-oxetan-3-yl-piperidin-3-yl)-1H-pyrazol-4-yl]-5-trifluoromethyl-pyrimidine-2,4-diamine, N4-ethyl-N$_2$-[5-methyl-1-((S)-1-methyl-piperidin-3-yl)-1H-pyrazol-4-yl]-5-trifluoromethyl-pyrimidine-2,4-diamine, or N4-ethyl-N$_2$-[3-methyl-1-((S)-1-methyl-piperidin-3-yl)-1H-pyrazol-4-yl]-5-trifluoromethyl-pyrimidine-2,4-diamine, or a stereoisomer thereof.

In one embodiment, the compound is not 5-(4-((4-cyclopropyl-5-(trifluoromethyl)pyrimidin-2-yl)amino)-3-methyl-1H-pyrazol-1-yl)-1-ethylpiperidin-2-one, 5-(4-((4-cyclopropyl-5-(trifluoromethyl)pyrimidin-2-yl)amino)-3-methyl-1H-pyrazol-1-yl)-1-ethylpiperidin-2-one, 5-(4-((4-cyclopropyl-5-(trifluoromethyl)pyrimidin-2-yl)amino)-3-methyl-1H-pyrazol-1-yl)-1-methylpiperidin-2-one, 5-(4-((4-cyclopropyl-5-(trifluoromethyl)pyrimidin-2-yl)amino)-5-methyl-1H-pyrazol-1-yl)-1-ethylpiperidin-2-one, N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine, or 5-(4-((4-cyclopropyl-5-(trifluoromethyl)pyrimidin-2-yl)amino)-5-methyl-1H-pyrazol-1-yl)-1-ethylpiperidin-2-one, 5-(4-((4-cyclopropyl-5-(trifluoromethyl)pyrimidin-2-yl)amino)-5-methyl-1H-pyrazol-1-yl)-1-methylpiperidin-2-one, or a stereoisomer thereof.

In one embodiment, provided is a compound of formula IVB-b:

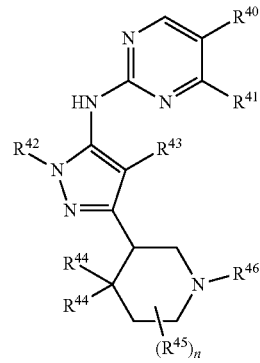

IVB-b or a pharmaceutically acceptable salt, deuterated analog, prodrug, stereoisomer, or a mixture of stereoisomers thereof, wherein $R^{43}$, $R^{44}$, $R^{45}$, $R^{46}$, and n are as defined herein, and:

$R^{40}$ is halo or $C_{1-6}$ haloalkyl;

$R^{41}$ is —N($R^{49}$)($R^{50}$);

$R^{42}$ is optionally substituted cyclopropyl;

$R^{49}$ is hydrogen; and $R^{50}$ is optionally substituted $C_{1-6}$ alkyl.

In one embodiment, provided is a compound of formula V:

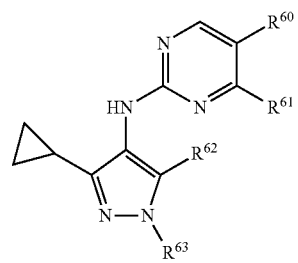

V or a pharmaceutically acceptable salt, deuterated analog, prodrug, stereoisomer, or a mixture of stereoisomers thereof, wherein:

$R^{60}$ is halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —C(O)$R^{64}$, or —C(O)N($R^{65}$)($R^{66}$);

$R^{61}$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{65}$)($R^{66}$);

$R^{62}$ is hydrogen or halo;

$R^{63}$ is hydrogen, halo, cyano, optionally substituted $C_{1-6}$ alkyl, optionally substituted $C_{1-6}$ alkenyl, optionally substituted $C_{1-6}$ alkynyl, optionally substituted cycloalkyl, optionally substituted heterocyclyl, optionally substituted heteroaryl, optionally substituted $C_{1-6}$ alkylthio, optionally substituted $C_{1-6}$ alkylsulfonyl, —C(O)$R^{64}$, or —C(O)N($R^{65}$)($R^{66}$);

each $R^{64}$ is independently optionally substituted $C_{1-6}$ alkyl or optionally substituted $C_{1-6}$ alkoxy; and $R^{65}$ and $R^{66}$ are each independently hydrogen, optionally substituted $C_{1-6}$ alkyl, optionally substituted cycloalkyl, or $R^{65}$ and $R^{66}$ together form an optionally substituted heterocyclyl group.

In one embodiment, the compound is not N₂-(3-cyclopropyl-1-methyl-1H-pyrazol-4-yl)-N4-methyl-5-(trifluoromethyl)pyrimidine-2,4-diamine, N₂-(5-cyclopropyl-1-methyl-1H-pyrazol-4-yl)-N4-methyl-5-(trifluoromethyl)pyrimidine-2,4-diamine, 1-(3-cyclopropyl-4-(4-(methylamino)-5-(trifluoromethyl)pyrimidin-2-ylamino)-1H-pyrazol-1-yl)-2-methylpropan-2-ol, 1-(3-cyclopropyl-4-(4-(ethylamino)-5-(trifluoromethyl)pyrimidin-2-ylamino)-1H-pyrazol-1-yl)-2-methylpropan-2-ol, 2-(3-cyclopropyl-4-(4-(methylamino)-5-(trifluoromethyl)pyrimidin-2-ylamino)-1H-pyrazol-1-yl)-2-methylpropanenitrile, or 2-[4-(5-chloro-4-methoxy-pyrimidin-2-ylamino)-3-cyclopropyl-pyrazol-1-yl]-2-methyl-propionitrile, or a stereoisomer thereof.

In one embodiment, provided is a compound as shown in Table 1A or a pharmaceutically acceptable salt, deuterated analog, prodrug, stereoisomer, or a mixture of stereoisomers thereof.

TABLE 1A

| No. | Structure |
|---|---|
| 1 | 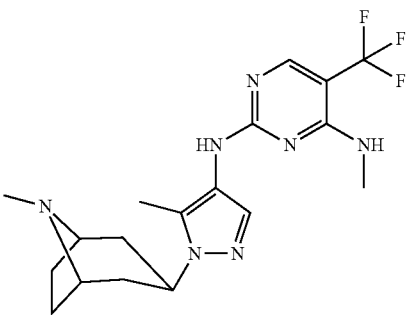 [SMILES: CNc1nc(Nc2cnn(C3CC4CCC(C3)N4C)c2C)ncc1C(F)(F)F] |
| 2 | 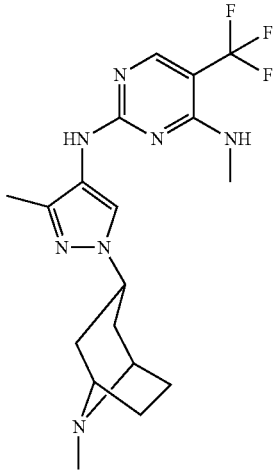 [SMILES: CNc1nc(Nc2cn(C3CC4CCC(C3)N4C)nc2C)ncc1C(F)(F)F] |

TABLE 1A-continued

| No. | Structure |
|---|---|
| 3 | 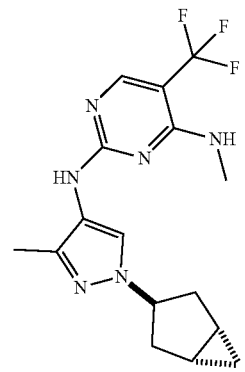 |
| 4 | 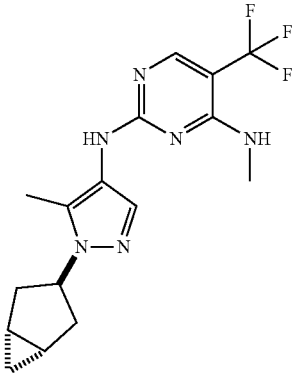 |
| 5 | 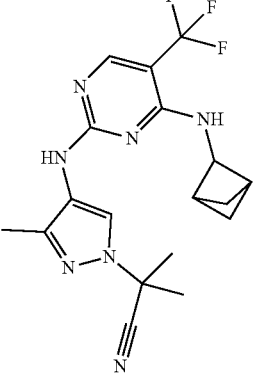 |
| 6 | 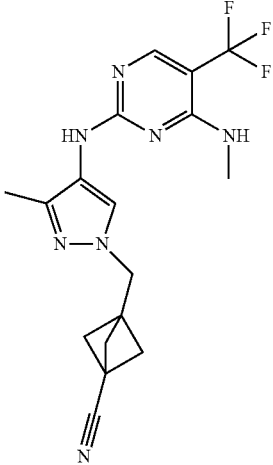 [SMILES: CNc1nc(Nc2cn(CC34CC(C#N)(C3)C4)nc2C)ncc1C(F)(F)F] |

TABLE 1A-continued

| No. | Structure |
|---|---|
| 7 | 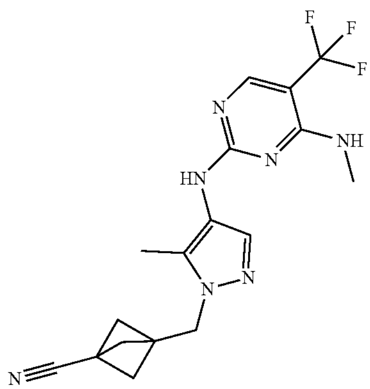 [SMILES: CNc1nc(Nc2cnn(CC34CC(C#N)(C3)C4)c2C)ncc1C(F)(F)F] |
| 8 | 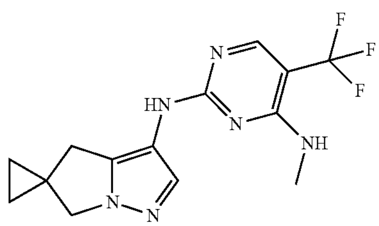 [SMILES: CNc1nc(Nc2cnn3c2CC2(CC2)C3)ncc1C(F)(F)F] |
| 9 | 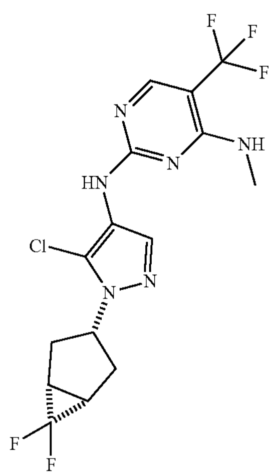 |
| 10 | 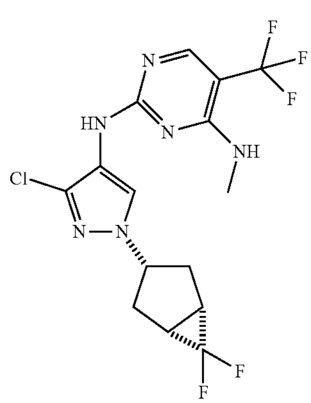 |
| 11 | |
| 12 | |
| 13 | |
| 14 | |

TABLE 1A-continued

| No. | Structure |
|---|---|
| 15 | 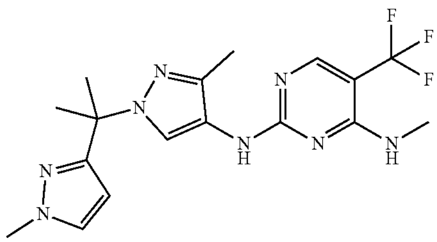 |
| 16 | 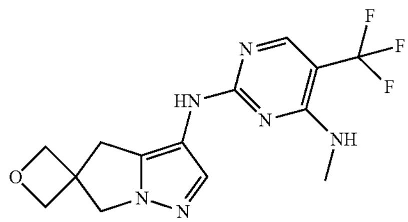 [SMILES: CNc1nc(Nc2cnn3c2CC2(COC2)C3)ncc1C(F)(F)F] |
| 17 | 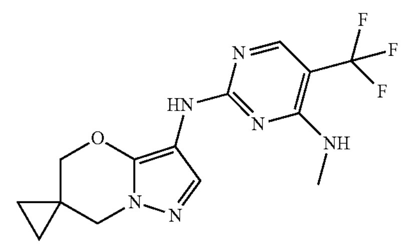 [SMILES: CNc1nc(Nc2cnn3c2OCC2(CC2)C3)ncc1C(F)(F)F] |
| 18 | 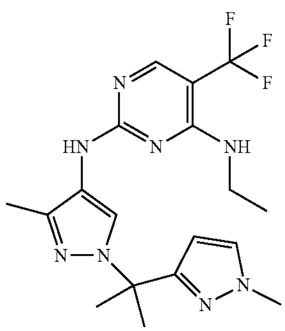 |
| 19 | 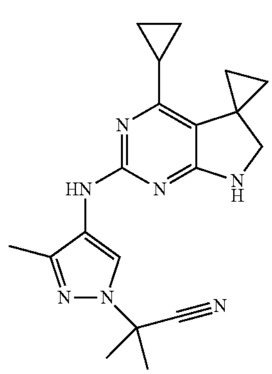 [SMILES: Cc1nn(C(C)(C)C#N)cc1Nc1nc2c(c(C3CC3)n1)C1(CC1)CN2] |
| 20 | |
| 21 | |
| 22 | |
| 23 | (First eluting isomer) |

TABLE 1A-continued

| No. | Structure |
|-----|-----------|
| 24 | (Second eluting isomer) |
| 25 | 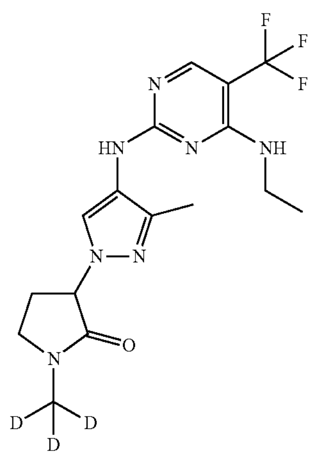 [SMILES: [2H]C([2H])([2H])N1CCC(n2cc(Nc3ncc(C(F)(F)F)c(NCC)n3)c(C)n2)C1=O] |
| 26 | 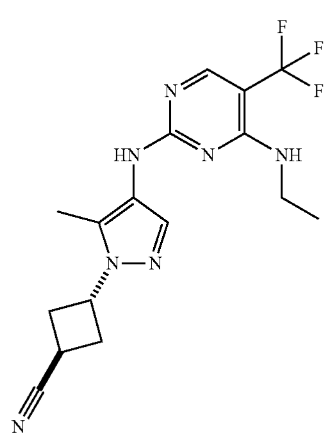 |
| 27 | |
| 28 | (First eluting isomer) |
| 29 | (Second eluting isomer) |

TABLE 1A-continued

| No. | Structure |
|---|---|
| 30 | (First eluting isomer) |
| 31 | (Second eluting isomer) |
| 32 | 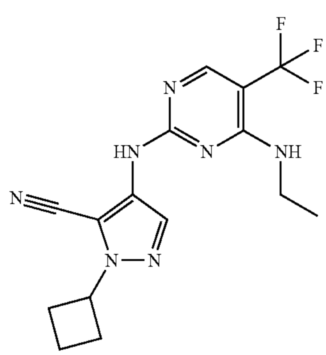 [SMILES: CCNc1nc(Nc2cnn(C3CCC3)c2C#N)ncc1C(F)(F)F] |
| 33 | 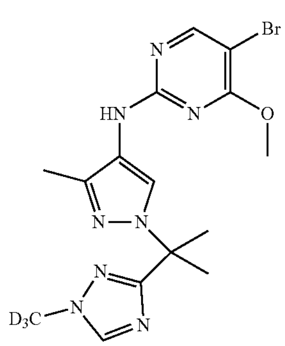 [SMILES: [2H]C([2H])([2H])n1cnc(C(C)(C)n2cc(Nc3ncc(Br)c(OC)n3)c(C)n2)n1] |
| 35 | 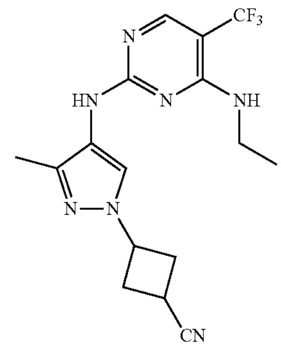 [SMILES: CCNc1nc(Nc2cn(C3CC(C#N)C3)nc2C)ncc1C(F)(F)F] |
| 35A | 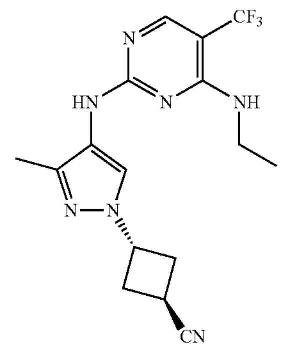 [SMILES: CCNc1nc(Nc2cn([C@H]3C[C@H](C#N)C3)nc2C)ncc1C(F)(F)F] |
| 35B | 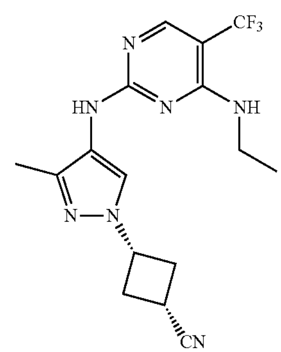 [SMILES: CCNc1nc(Nc2cn([C@H]3C[C@@H](C#N)C3)nc2C)ncc1C(F)(F)F] |
| 36 | 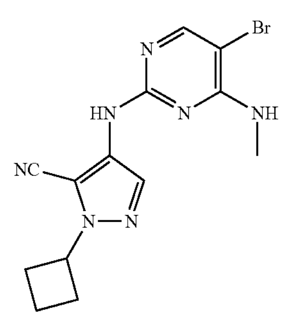 [SMILES: CNc1nc(Nc2cnn(C3CCC3)c2C#N)ncc1Br] |

TABLE 1A-continued

| No. | Structure |
|---|---|
| 37 | 5-bromo-4-methoxy-pyrimidin-2-yl aminopyrazole with cyano and N-cyclobutyl |
| 38 | 5-CF3-4-(cyclopropylamino)pyrimidin-2-yl aminopyrazole with 3-methyl and N-(2-cyanopropan-2-yl) |
| 39 | 5-CF3-4-((2-fluorocyclopropyl)amino)pyrimidin-2-yl aminopyrazole with 3-methyl and N-(2-cyanopropan-2-yl) |
| 39A | 5-CF3-4-(((1R,2S)-2-fluorocyclopropyl)amino)pyrimidin-2-yl aminopyrazole with 3-methyl and N-(2-cyanopropan-2-yl) |
| 40 | 5-CF3-4-(CD3-amino)pyrimidin-2-yl aminopyrazole with 3-CD3 and N-(2-cyano-1,1,1,3,3,3-hexadeutero-propan-2-yl) |

TABLE 1A-continued

| No. | Structure |
|---|---|
| 41 | 5-bromo-4-methoxy-pyrimidin-2-yl aminopyrazole with 3-methyl and N-(2-cyanopropan-2-yl) |
| 42 | 5-bromo-4-(methylamino)pyrimidin-2-yl aminopyrazole with 3-methyl and N-(2-cyanopropan-2-yl) |
| 43 | 5-bromo-4-(ethylamino)pyrimidin-2-yl aminopyrazole with 3-methyl and N-(2-cyanopropan-2-yl) |
| 44 | 5-CF3-4-(ethylamino)pyrimidin-2-yl aminopyrazole with 3-CD3 and N-(2-cyano-1,1,1,3,3,3-hexadeutero-propan-2-yl) |
| 45 | 5-CF3-4-(methylamino)pyrimidin-2-yl aminopyrazole with 3-CD3 and N-(2-cyano-1,1,1,3,3,3-hexadeutero-propan-2-yl) |

TABLE 1A-continued

| No. | Structure |
|---|---|
| 46 | (structure) |
| 47 | (structure) |
| 48 | (structure) |
| 49 | (structure) |
| 50 | (structure) |
| 51 | (structure) |
| 52A | (structure) (First eluting isomer) |
| 52B | (structure) (Second eluting isomer) |
| 53 | (structure) |
| 54A | (structure) (First eluting isomer) |

TABLE 1A-continued

| No. | Structure |
|---|---|
| 54B | (Second eluting isomer) |
| 55 | 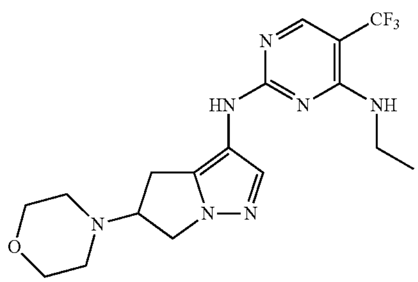 [SMILES: CCNc1nc(Nc2cnn3c2CC(N2CCOCC2)C3)ncc1C(F)(F)F] |
| 56 | 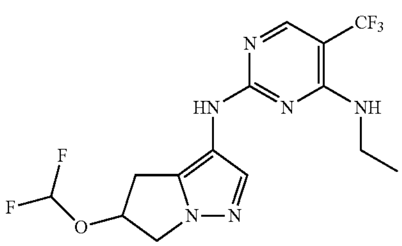 [SMILES: CCNc1nc(Nc2cnn3c2CC(OC(F)F)C3)ncc1C(F)(F)F] |
| 58 | 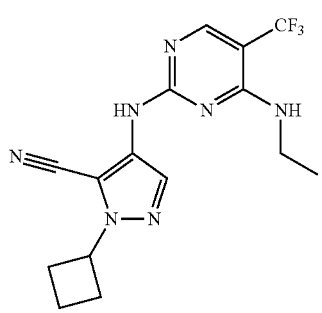 [SMILES: CCNc1nc(Nc2cnn(C3CCC3)c2C#N)ncc1C(F)(F)F] |
| 59 | 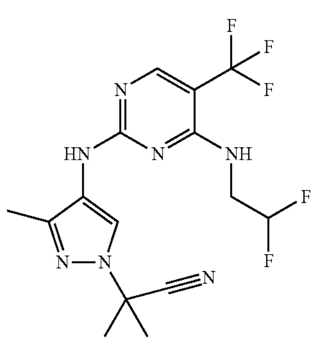 [SMILES: Cc1nn(C(C)(C)C#N)cc1Nc1ncc(C(F)(F)F)c(NCC(F)F)n1] |
| 60 | 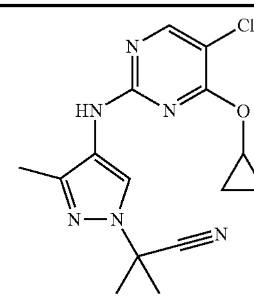 |
| 61 | 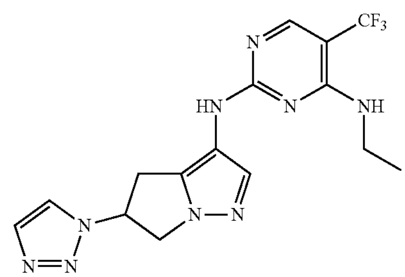 [SMILES: CCNc1nc(Nc2cnn3c2CC(n2ccnn2)C3)ncc1C(F)(F)F] |
| 62 | 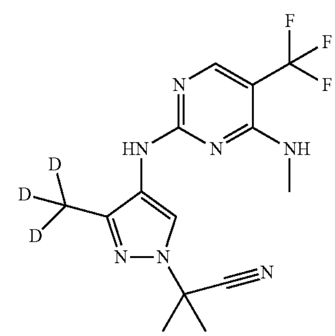 [SMILES: [2H]C([2H])([2H])c1nn(C(C)(C)C#N)cc1Nc1ncc(C(F)(F)F)c(NC)n1] |
| 63 | 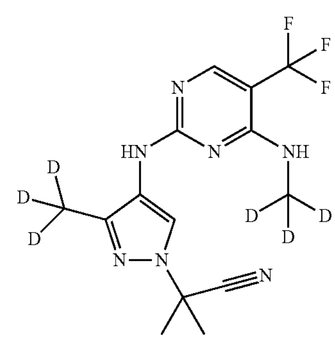 [SMILES: [2H]C([2H])([2H])Nc1nc(Nc2cn(C(C)(C)C#N)nc2C([2H])([2H])[2H])ncc1C(F)(F)F] |
| 64A | (First eluting isomer) |

TABLE 1A-continued

| No. | Structure |
|-----|-----------|
| 64B | (Second eluting isomer) |
| 65 | 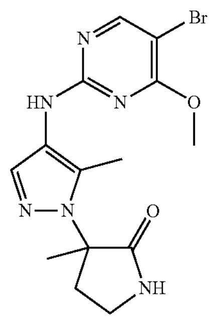 [SMILES: COc1nc(Nc2cnn(C3(C)CCNC3=O)c2C)ncc1Br] |
| 66 | 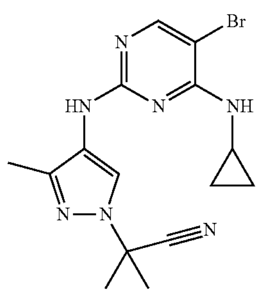 |
| 67 | 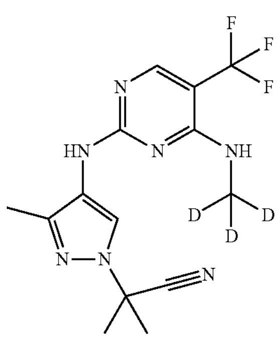 [SMILES: [2H]C([2H])([2H])Nc1nc(Nc2cn(C(C)(C)C#N)nc2C)ncc1C(F)(F)F] |
| 72 | 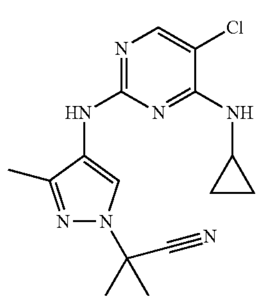 [SMILES: Cc1nn(C(C)(C)C#N)cc1Nc1ncc(Cl)c(NC2CC2)n1] |

TABLE 1A-continued

| No. | Structure |
|-----|-----------|
| 73 | 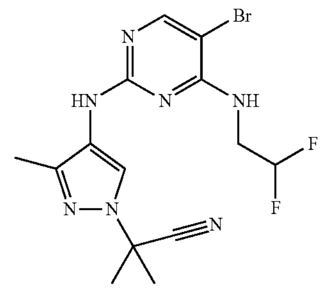 [SMILES: Cc1nn(C(C)(C)C#N)cc1Nc1ncc(Br)c(NCC(F)F)n1] |
| 74 | 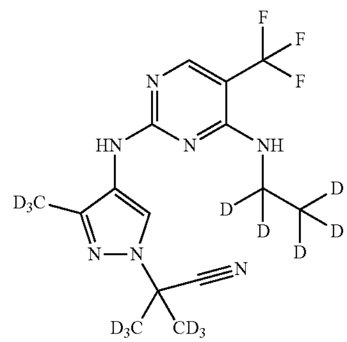 [SMILES: [2H]C([2H])([2H])c1nn(C(C#N)(C([2H])([2H])[2H])C([2H])([2H])[2H])cc1Nc1ncc(C(F)(F)F)c(NC([2H])([2H])C([2H])([2H])[2H])n1] |
| 76 | 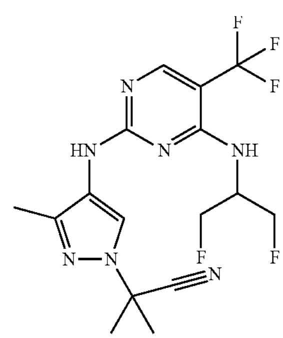 [SMILES: Cc1nn(C(C)(C)C#N)cc1Nc1ncc(C(F)(F)F)c(NC(CF)CF)n1] |
| 80 | 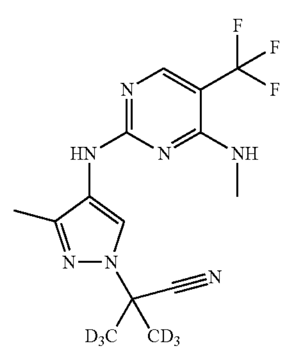 [SMILES: [2H]C([2H])([2H])C(C#N)(n1cc(Nc2ncc(C(F)(F)F)c(NC)n2)c(C)n1)C([2H])([2H])[2H]] |

TABLE 1A-continued

| No. | Structure |
|---|---|
| 84 | (structure) |
| 85 | (structure) |
| 87 | (structure) |
| 89 | (structure) |
| 90 | (structure) (Second eluting isomer) |
| 91 | (structure) (Second eluting isomer) |
| 92 | (structure) (Second eluting isomer) |
| 93 | (structure) |

TABLE 1A-continued

| No. | Structure |
|---|---|
| 94 | (structure) |
| 95 | (structure) |
| 96 | (structure) |
| 97 | (structure) |
| 98 | (structure) |
| 99 | (structure) (Second eluting isomer) |
| 100 | (structure) (First eluting isomer) |
| 101 | (structure) |

TABLE 1A-continued

| No. | Structure |
|---|---|
| 102 | (First eluting isomer) |
| 103 | (Second eluting isomer) |
| 104 | (First eluting isomer) |
| 105 | 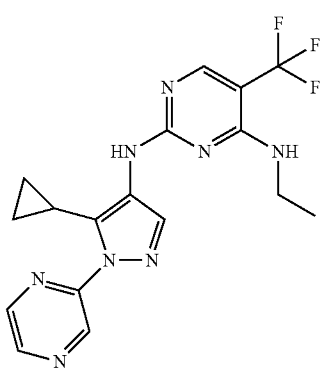 [SMILES: CCNc1nc(Nc2cnn(-c3cnccn3)c2C2CC2)ncc1C(F)(F)F] |
| 106 | |
| 107 | |
| 108 | |
| 109 | |

TABLE 1A-continued

| No. | Structure |
|---|---|
| 110 | (structure) |
| 111 | (structure) |
| 112 | (structure) |
| 113 | (structure) (Second eluting isomer) |
| 114 | (structure) (First eluting isomer) |
| 115 | (structure) (Second eluting isomer) |
| 116 | (structure) (First eluting isomer) |
| 117 | (structure) (Second eluting isomer) |

TABLE 1A-continued
| No. | Structure |
|---|---|
| 118 | 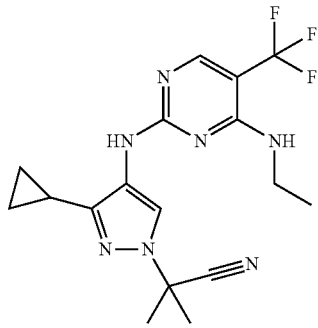 [SMILES: CCNc1nc(Nc2cn(C(C)(C)C#N)nc2C2CC2)ncc1C(F)(F)F] |
| 119 | 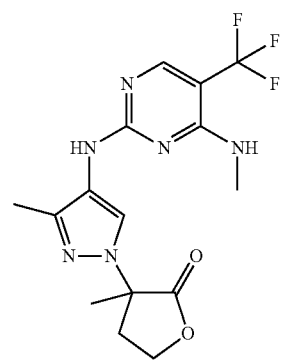
(Second eluting isomer) |
| 120 | 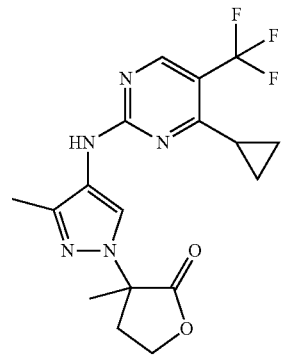
(First eluting isomer) |
| 121 | 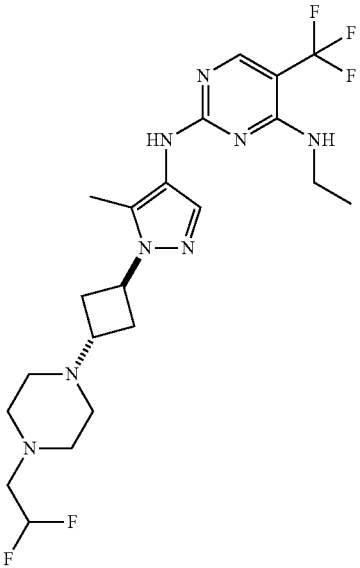 |
| 122 | 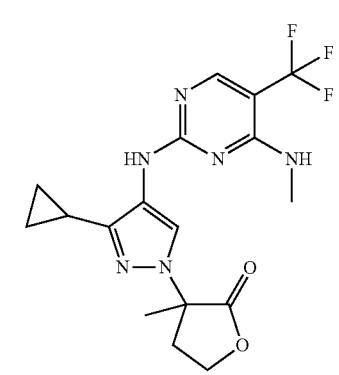
(First eluting isomer) |
| 123 | 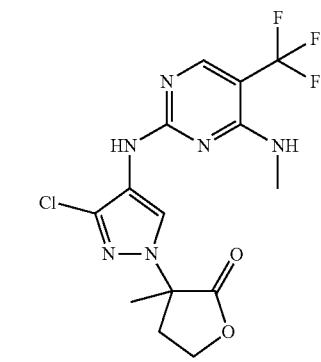
(First eluting isomer) |

TABLE 1A-continued
| No. | Structure |
|---|---|
| 124 | 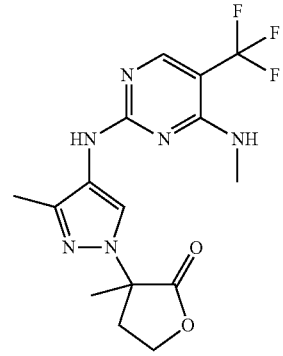<br>(First eluting isomer) |
| 125 | 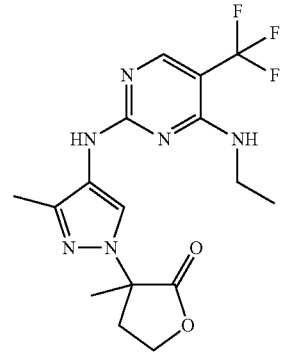<br>(Second eluting isomer) |
| 194 | 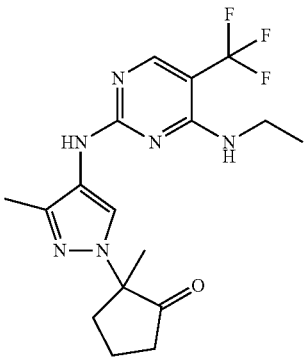 [SMILES: CCNc1nc(Nc2cn(C3(C)CCCC3=O)nc2C)ncc1C(F)(F)F] |
| 195 | 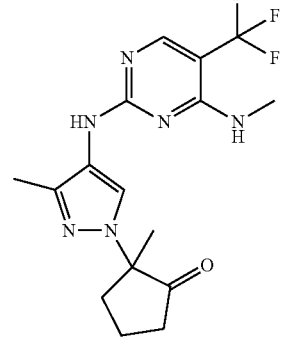 |
| 196 | 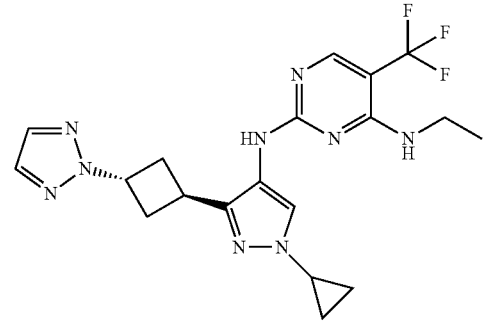 [SMILES: CCNc1nc(Nc2cn(C3CC3)nc2[C@H]2C[C@H](n3nccn3)C2)ncc1C(F)(F)F] |
| 197 | 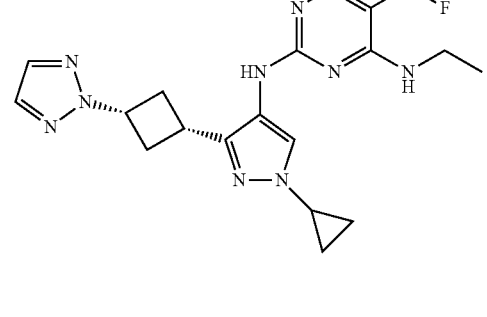 |
| 198 | 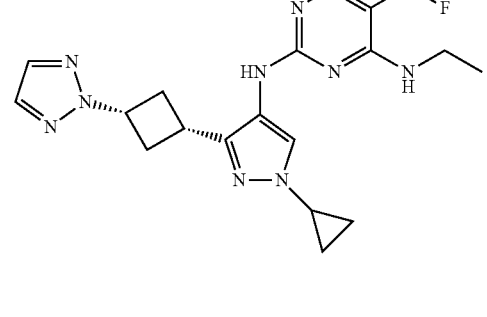 |
| 199 | 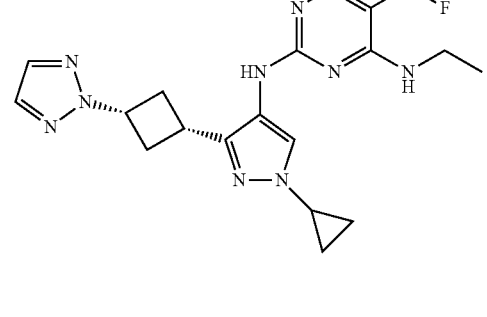 |

TABLE 1A-continued
| No. | Structure |
|---|---|
| 200 | (first eluting isomer) |
| 201 | (second eluting isomer) |
| 202 | (first eluting isomer) |
| 203 | (second eluting isomer) |
| 204 | (first eluting isomer) |
| 205 | (second eluting isomer) |
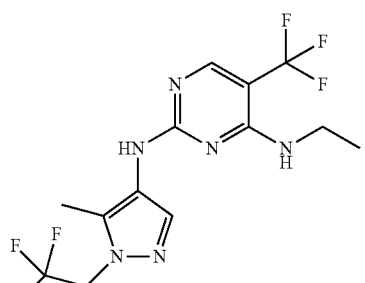
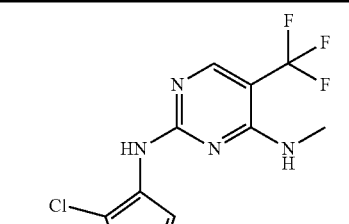

TABLE 1A-continued
| No. | Structure |
|---|---|
| 206 | 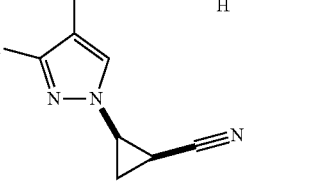 (second eluting isomer) |
| 207 | (first eluting isomer) |
| 208 | (first eluting isomer) |
| 209 | (second eluting isomer) |
| 210 | 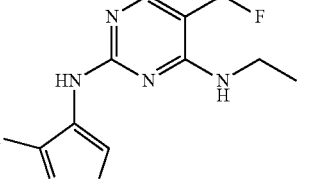 (first eluting isomer) |
| 211 | (second eluting isomer) |
| 212 | (first eluting isomer) |
| 213 | (second eluting isomer) |

TABLE 1A-continued
| No. | Structure |
|---|---|
| 214 | 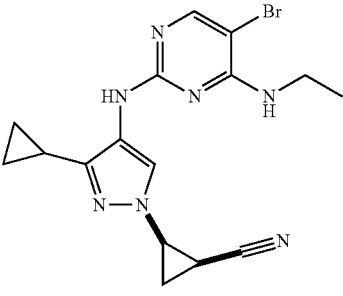 (second eluting isomer) |
| 215 | (second eluting isomer) |
| 216 | (First eluting isomer) |
| 217 | (second eluting isomer) |
| 218 | 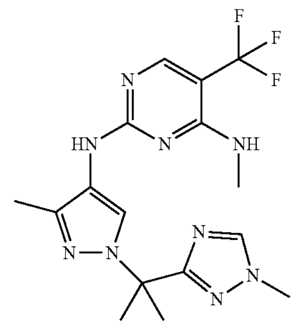 |
In some embodiments, the compound is in Table 1B or is a pharmaceutically acceptable salt, prodrug, tautomer, stereoisomer, or a mixture of stereoisomers thereof:
TABLE 1B
| No. | Structure |
|---|---|
| 34 | 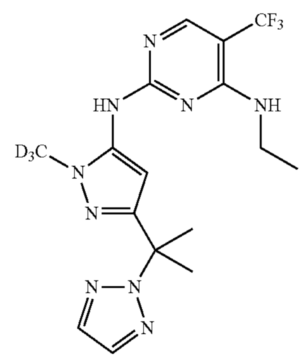 [SMILES: [2H]C([2H])([2H])n1nc(C(C)(C)n2nccn2)cc1Nc1ncc(C(F)(F)F)c(NCC)n1] |
| 57 | 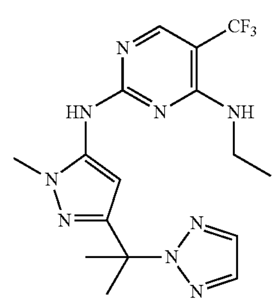 [SMILES: CCNc1nc(Nc2cc(C(C)(C)n3nccn3)nn2C)ncc1C(F)(F)F] |
| 68 | 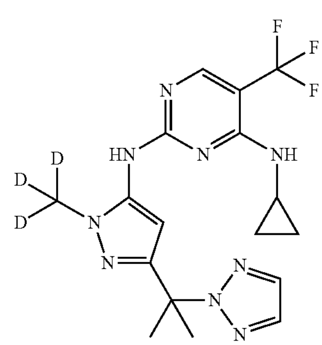 [SMILES: [2H]C([2H])([2H])n1nc(C(C)(C)n2nccn2)cc1Nc1ncc(C(F)(F)F)c(NC2CC2)n1] |

TABLE 1B-continued

| No. | Structure |
|-----|-----------|
| 69 | 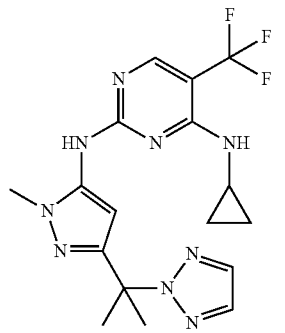 [SMILES: Cn1nc(C(C)(C)n2nccn2)cc1Nc1ncc(C(F)(F)F)c(NC2CC2)n1] |
| 70 | 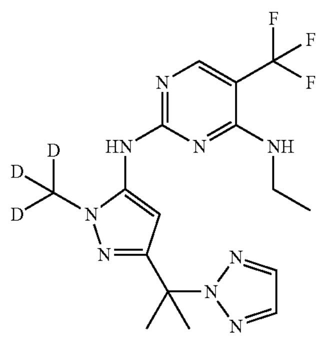 [SMILES: [2H]C([2H])([2H])n1nc(C(C)(C)n2nccn2)cc1Nc1ncc(C(F)(F)F)c(NCC)n1] |
| 71 | 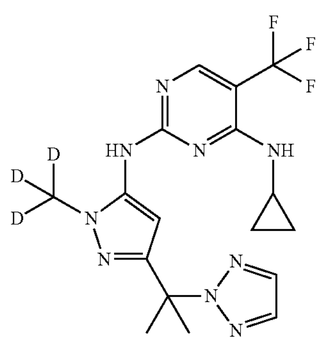 [SMILES: [2H]C([2H])([2H])n1nc(C(C)(C)n2nccn2)cc1Nc1ncc(C(F)(F)F)c(NC2CC2)n1] |
| 75 | 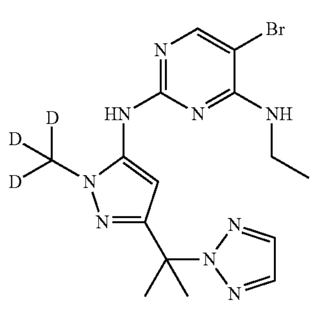 [SMILES: [2H]C([2H])([2H])n1nc(C(C)(C)n2nccn2)cc1Nc1ncc(Br)c(NCC)n1] |
| 77 | 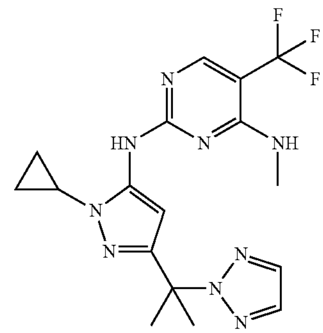 [SMILES: CNc1nc(Nc2cc(C(C)(C)n3nccn3)nn2C2CC2)ncc1C(F)(F)F] |
| 78 | 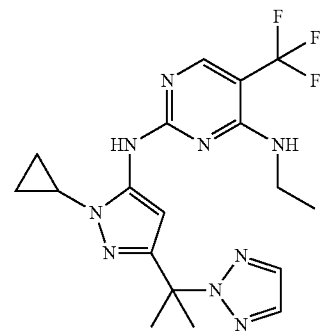 [SMILES: CCNc1nc(Nc2cc(C(C)(C)n3nccn3)nn2C2CC2)ncc1C(F)(F)F] |
| 79 | 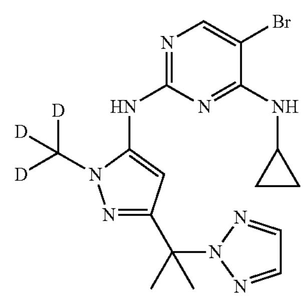 [SMILES: [2H]C([2H])([2H])n1nc(C(C)(C)n2nccn2)cc1Nc1ncc(Br)c(NC2CC2)n1] |
| 81 | 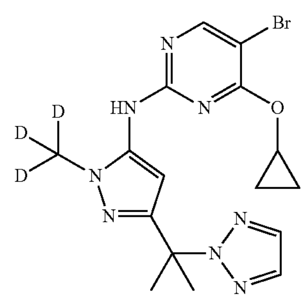 [SMILES: [2H]C([2H])([2H])n1nc(C(C)(C)n2nccn2)cc1Nc1ncc(Br)c(OC2CC2)n1] |
| 82 | 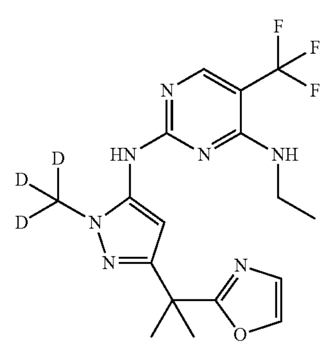 [SMILES: [2H]C([2H])([2H])n1nc(C(C)(C)c2ncco2)cc1Nc1ncc(C(F)(F)F)c(NCC)n1] |

TABLE 1B-continued

| No. | Structure |
|-----|-----------|
| 83  | (structure) |
| 86  | (structure) |
| 88  | (structure) |
| 126 | (structure) |
| 127 | (structure) |
| 128 | (structure) |
| 129 | (structure) |
| 130 | (structure) |

TABLE 1B-continued

| No. | Structure |
|---|---|
| 131 | (structure) |
| 132 | (structure) |
| 133 | (structure) |
| 134 | (structure) |
| 135 | (structure) |
| 136 | (structure) |
| 137 | (structure) (First eluting isomer) |
| 138 | (structure) (Second eluting isomer) |

TABLE 1B-continued

| No. | Structure |
|---|---|
| 139 | (chemical structure) |
| 140 | (chemical structure) |
| 141 | (chemical structure) |
| 142 | (chemical structure) |
| 143 | (chemical structure) (First eluting isomer) |
| 144 | (chemical structure) (Second eluting isomer) |
| 145 | (chemical structure) |
| 146 | (chemical structure) (First eluting isomer) |

US 10,590,114 B2
TABLE 1B-continued
| No. | Structure |
|---|---|
| 147 | 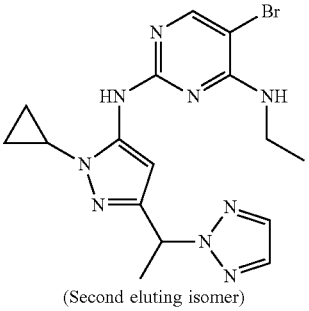<br>(Second eluting isomer) |
| 148 | 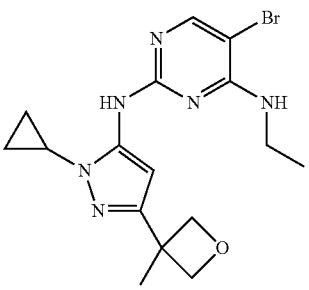 [SMILES: CCNc1nc(Nc2cc(C3(C)COC3)nn2C2CC2)ncc1Br] |
| 149 | 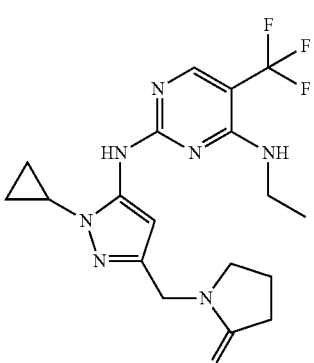 |
| 150 | 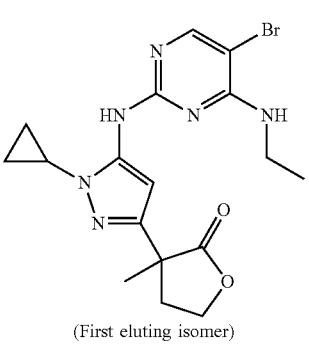<br>(First eluting isomer) |
| 151 | 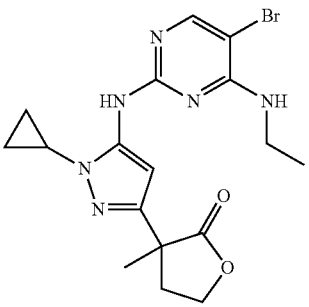 [SMILES: CCNc1nc(Nc2cc(C3(C)CCOC3=O)nn2C2CC2)ncc1Br] |
TABLE 1B-continued
| No. | Structure |
|---|---|
|  | (Second eluting isomer) |
| 152 | 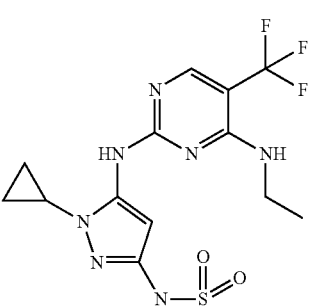 |
| 153 | 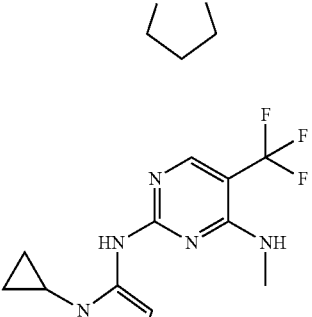 |
| 154 |  |
| 155 | <br>(First eluting isomer) |

TABLE 1B-continued

| No. | Structure |
|---|---|
| 156 | (Second eluting isomer) |
| 157 | 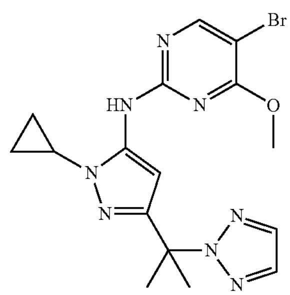 [SMILES: COc1nc(Nc2cc(C(C)(C)n3nccn3)nn2C2CC2)ncc1Br] |
| 158 | 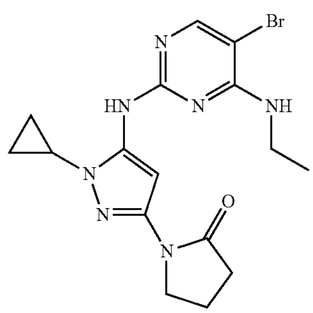 [SMILES: CCNc1nc(Nc2cc(N3CCCC3=O)nn2C2CC2)ncc1Br] |
| 159 | 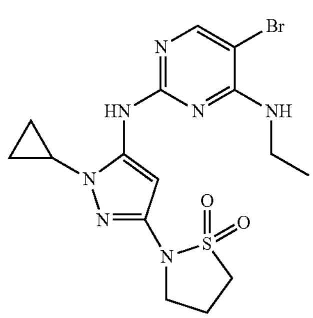 [SMILES: CCNc1nc(Nc2cc(N3CCCS3(=O)=O)nn2C2CC2)ncc1Br] |
| 160 | (First eluting isomer) |
| 161 | (Second eluting isomer) |
| 162 | |
| 163 | |

TABLE 1B-continued

| No. | Structure |
|---|---|
| 164 | 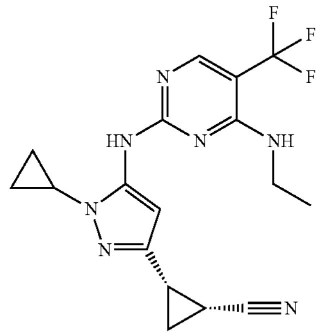 [SMILES: CCNc1nc(Nc2cc([C@H]3C[C@H]3C#N)nn2C2CC2)ncc1C(F)(F)F] |
| 165 | 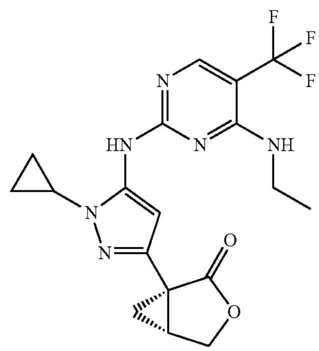 [SMILES: CCNc1nc(Nc2cc([C@]34C[C@H]3COC4=O)nn2C2CC2)ncc1C(F)(F)F] |
| 166 | (First eluting isomer) |
| 167 | (Second eluting isomer) |

TABLE 1B-continued

| No. | Structure |
|---|---|
| 168 | 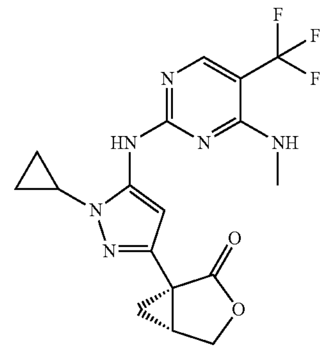 [SMILES: CNc1nc(Nc2cc([C@]34C[C@H]3COC4=O)nn2C2CC2)ncc1C(F)(F)F] |
| 169 | 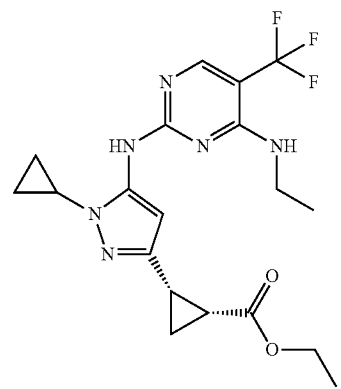 [SMILES: CCNc1nc(Nc2cc([C@H]3C[C@H]3C(=O)OCC)nn2C2CC2)ncc1C(F)(F)F] |
| 170 | 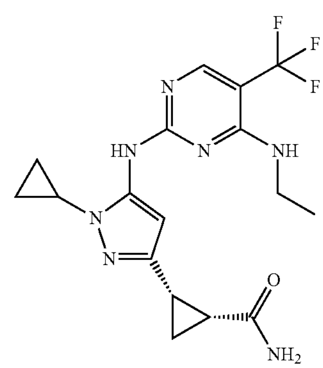 [SMILES: CCNc1nc(Nc2cc([C@H]3C[C@H]3C(N)=O)nn2C2CC2)ncc1C(F)(F)F] |
| 171 | (First eluting isomer) |

TABLE 1B-continued

| No. | Structure |
|---|---|
| 172 | (Second eluting isomer) |
| 173 | (First eluting isomer) |
| 174 | (Second eluting isomer) |
| 175 | (First eluting isomer) |
| 176 | (Second eluting isomer) |
| 177 | (First eluting isomer) |
| 178 | (Second eluting isomer) |
| 179 | |

TABLE 1B-continued
| No. | Structure |
|-----|-----------|
| 180 | 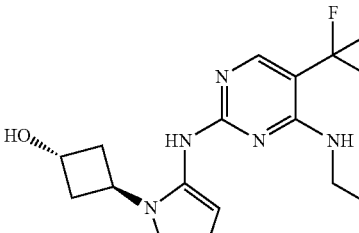 |
| 181 | 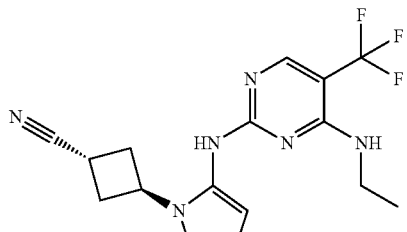 |
| 182 | 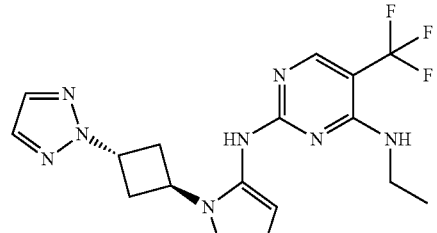 |
| 183 | 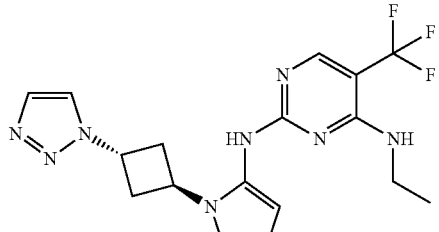 |
| 184 | 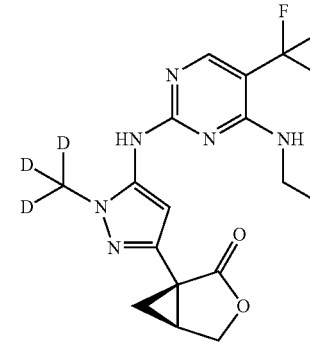 |
| 185 | 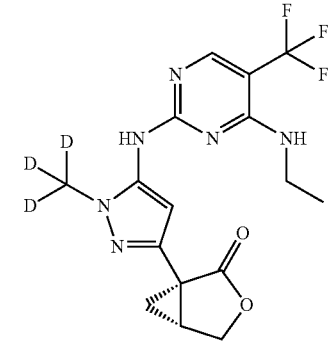 [SMILES: [2H]C([2H])([2H])n1nc([C@]23C[C@H]2COC3=O)cc1Nc1ncc(C(F)(F)F)c(NCC)n1] |
| 186 | 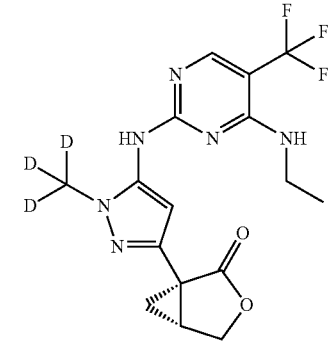 [SMILES: [2H]C([2H])([2H])n1nc([C@]23C[C@H]2COC3=O)cc1Nc1ncc(C(F)(F)F)c(NCC)n1] (First eluting isomer) |
| 187 | 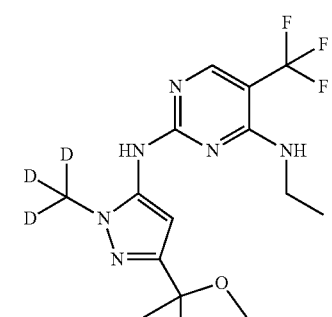 (Second eluting isomer) |
| 188 | 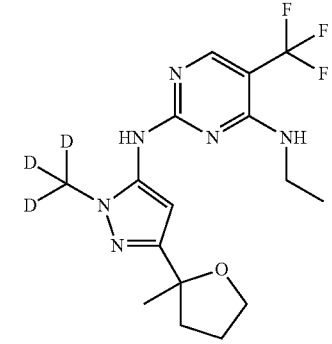 [SMILES: [2H]C([2H])([2H])n1nc(C2(C)CCCO2)cc1Nc1ncc(C(F)(F)F)c(NCC)n1] |

TABLE 1B-continued

| No. | Structure |
|---|---|
| 189 | (structure) |
| 190 | (structure) |
| 191 | (structure) |
| 192 | (structure) |
| 193 | (structure) |

In one embodiment, a compound may be selected from those compounds in Table 1A. Also included within the disclosure are pharmaceutically acceptable salts, prodrugs, stereoisomers, or a mixture of stereoisomers thereof. In certain embodiments, provided are compounds of Table 1A for use in the methods described herein.

In one embodiment, a compound may be selected from those compounds in Table 1B. Also included within the disclosure are pharmaceutically acceptable salts, prodrugs, stereoisomers, or a mixture of stereoisomers thereof. In certain embodiments, provided are compounds of Table 1B for use in the methods described herein.

Specific stereoisomers contemplated include the following in Table 2A and Table 2B.

TABLE 2A

| Structure |
|---|
| (structure) |
| (structure) |

TABLE 2A-continued

Structure

TABLE 2A-continued
Structure
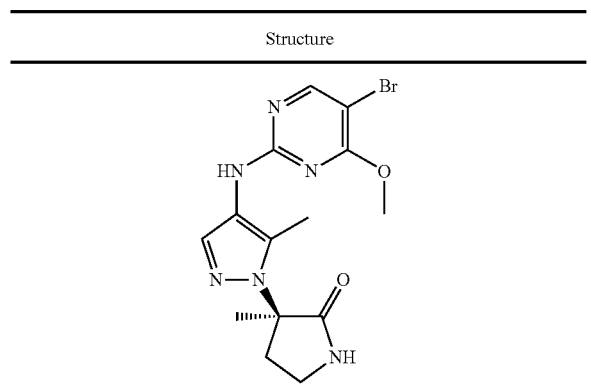
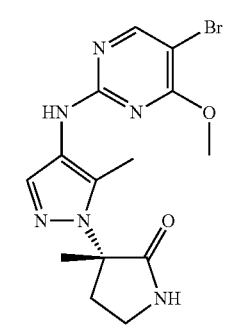 [SMILES: COc1nc(Nc2cnn([C@@]3(C)CCNC3=O)c2C)ncc1Br]
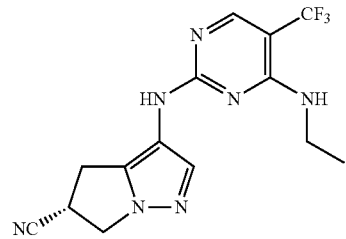 [SMILES: CCNc1nc(Nc2cnn3c2C[C@@H](C#N)C3)ncc1C(F)(F)F]
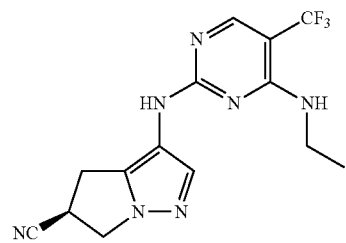 [SMILES: CCNc1nc(Nc2cnn3c2C[C@H](C#N)C3)ncc1C(F)(F)F]
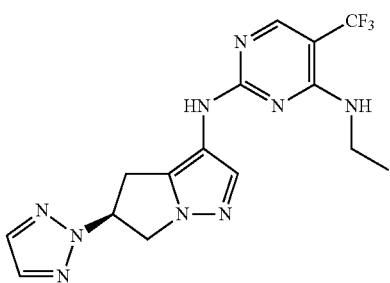 [SMILES: CCNc1nc(Nc2cnn3c2C[C@H](n2nccn2)C3)ncc1C(F)(F)F]
TABLE 2A-continued
Structure
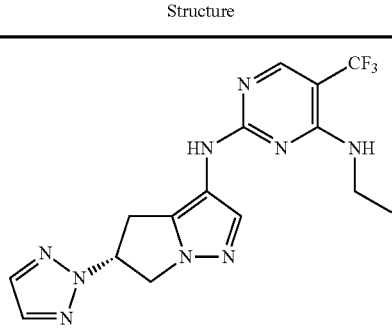
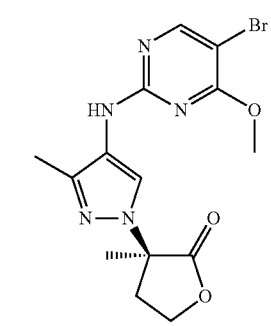 [SMILES: COc1nc(Nc2cn([C@]3(C)CCOC3=O)nc2C)ncc1Br]
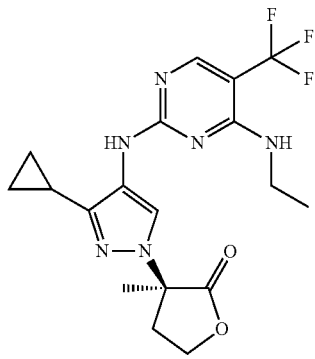 [SMILES: CCNc1nc(Nc2cn([C@]3(C)CCOC3=O)nc2C2CC2)ncc1C(F)(F)F]
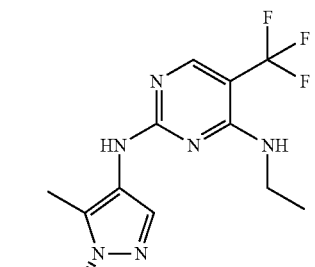

TABLE 2A-continued
Structure
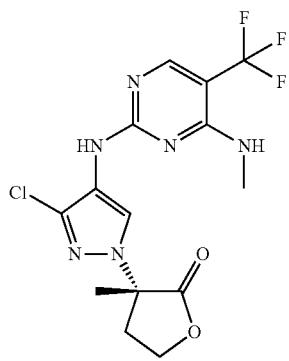 [SMILES: CNc1nc(Nc2cn([C@@]3(C)CCOC3=O)nc2Cl)ncc1C(F)(F)F]
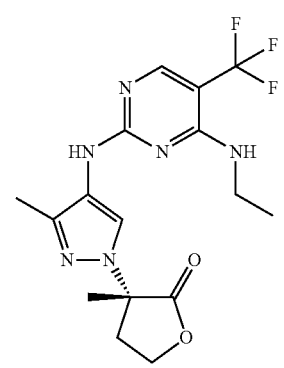 [SMILES: CCNc1nc(Nc2cn([C@@]3(C)CCOC3=O)nc2C)ncc1C(F)(F)F]
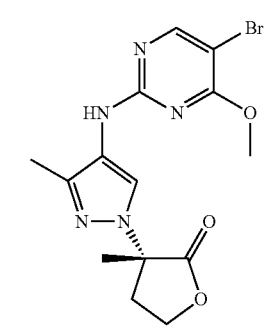 [SMILES: COc1nc(Nc2cn([C@@]3(C)CCOC3=O)nc2C)ncc1Br]
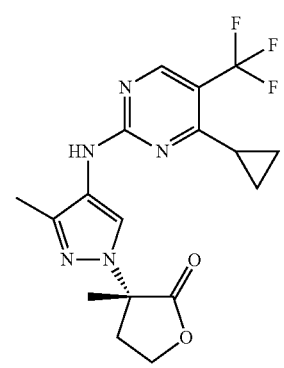 [SMILES: Cc1nn([C@@]2(C)CCOC2=O)cc1Nc1ncc(C(F)(F)F)c(C2CC2)n1]
TABLE 2A-continued
Structure
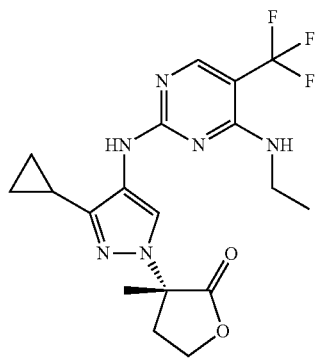 [SMILES: CCNc1nc(Nc2cn([C@@]3(C)CCOC3=O)nc2C2CC2)ncc1C(F)(F)F]
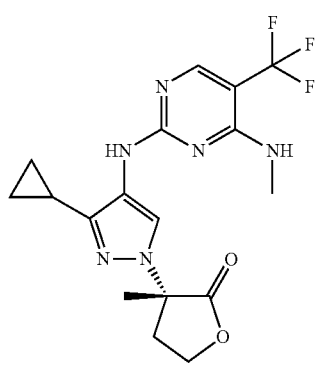 [SMILES: CNc1nc(Nc2cn([C@@]3(C)CCOC3=O)nc2C2CC2)ncc1C(F)(F)F]
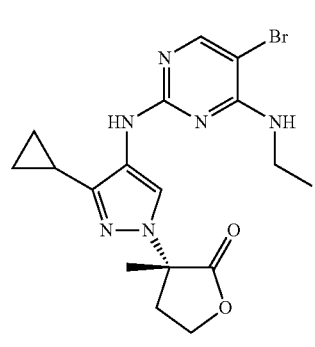 [SMILES: CCNc1nc(Nc2cn([C@@]3(C)CCOC3=O)nc2C2CC2)ncc1Br]
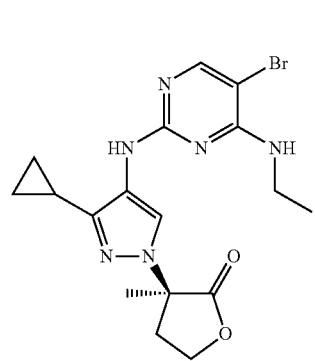 [SMILES: CCNc1nc(Nc2cn([C@]3(C)CCOC3=O)nc2C2CC2)ncc1Br]

TABLE 2A-continued

| Structure |
|---|
| (chemical structures) |

TABLE 2A-continued

Structure

TABLE 2A-continued

Structure

TABLE 2A-continued
Structure
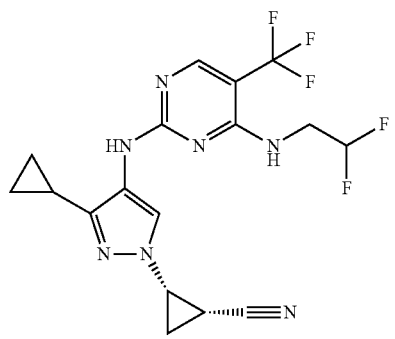 [SMILES: N#C[C@@H]1C[C@@H]1n1cc(Nc2ncc(C(F)(F)F)c(NCC(F)F)n2)c(C2CC2)n1]
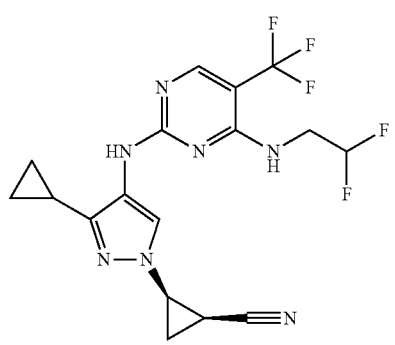 [SMILES: N#C[C@H]1C[C@H]1n1cc(Nc2ncc(C(F)(F)F)c(NCC(F)F)n2)c(C2CC2)n1]
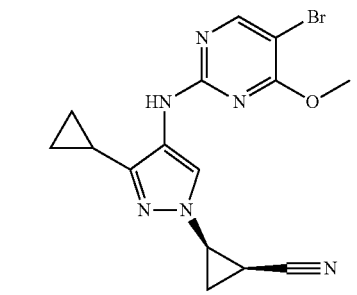 [SMILES: COc1nc(Nc2cn([C@@H]3C[C@@H]3C#N)nc2C2CC2)ncc1Br]
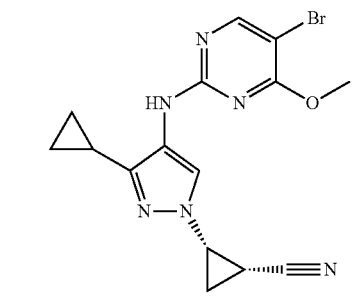 [SMILES: COc1nc(Nc2cn([C@H]3C[C@H]3C#N)nc2C2CC2)ncc1Br]
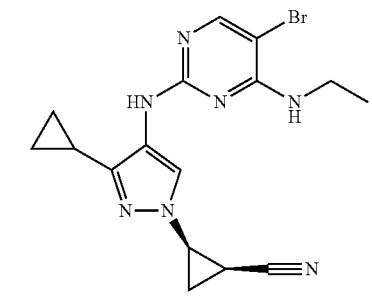 [SMILES: CCNc1nc(Nc2cn([C@@H]3C[C@@H]3C#N)nc2C2CC2)ncc1Br]
TABLE 2A-continued
Structure
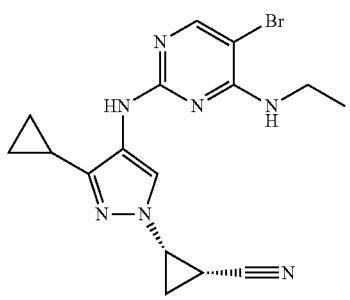 [SMILES: CCNc1nc(Nc2cn([C@H]3C[C@H]3C#N)nc2C2CC2)ncc1Br]
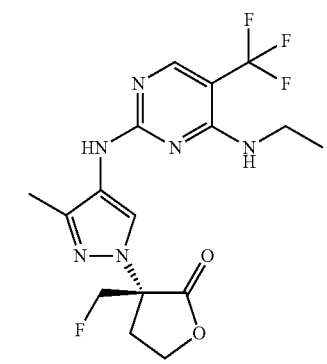 [SMILES: CCNc1nc(Nc2cn([C@@]3(CF)CCOC3=O)nc2C)ncc1C(F)(F)F]
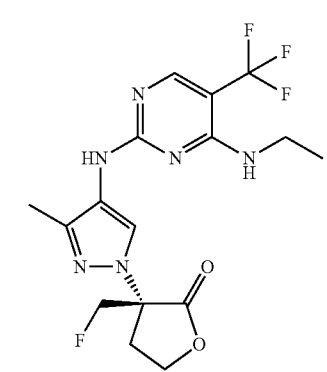 [SMILES: CCNc1nc(Nc2cn([C@@]3(CF)CCOC3=O)nc2C)ncc1C(F)(F)F]
or a pharmaceutically acceptable salt, deuterated analog, prodrug, stereoisomer, or a mixture of stereoisomers thereof.
TABLE 2B
Structure
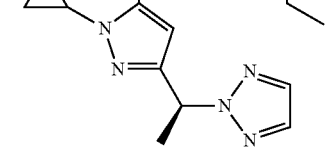

TABLE 2B-continued

Structure

TABLE 2B-continued
| Structure |
|---|
| 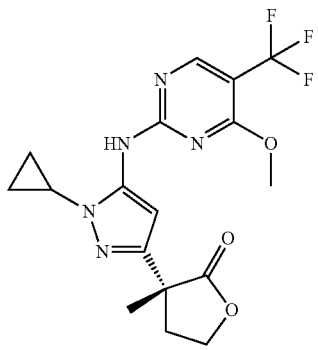 [SMILES: COc1nc(Nc2cc([C@@]3(C)CCOC3=O)nn2C2CC2)ncc1C(F)(F)F] |
| 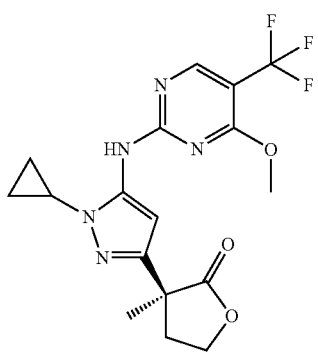 [SMILES: COc1nc(Nc2cc([C@]3(C)CCOC3=O)nn2C2CC2)ncc1C(F)(F)F] |
| 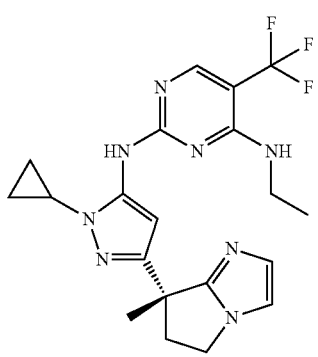 [SMILES: CCNc1nc(Nc2cc([C@@]3(C)CCn4ccnc43)nn2C2CC2)ncc1C(F)(F)F] |
| 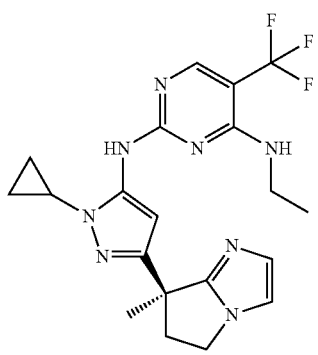 [SMILES: CCNc1nc(Nc2cc([C@]3(C)CCn4ccnc43)nn2C2CC2)ncc1C(F)(F)F] |
TABLE 2B-continued
| Structure |
|---|
| 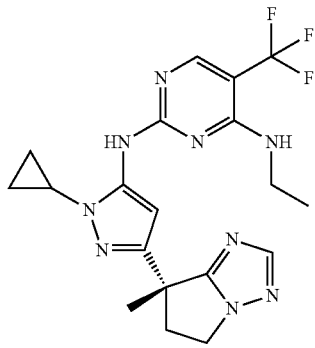 [SMILES: CCNc1nc(Nc2cc([C@@]3(C)CCn4ncnc43)nn2C2CC2)ncc1C(F)(F)F] |
| 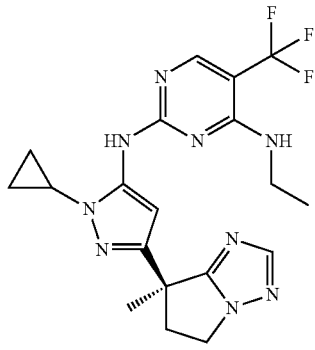 [SMILES: CCNc1nc(Nc2cc([C@]3(C)CCn4ncnc43)nn2C2CC2)ncc1C(F)(F)F] |
| 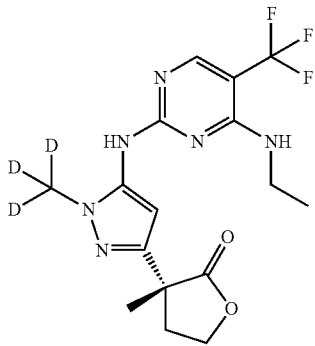 [SMILES: [2H]C([2H])([2H])n1nc([C@@]2(C)CCOC2=O)cc1Nc1ncc(C(F)(F)F)c(NCC)n1] |
| 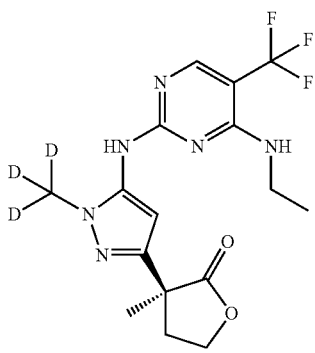 [SMILES: [2H]C([2H])([2H])n1nc([C@]2(C)CCOC2=O)cc1Nc1ncc(C(F)(F)F)c(NCC)n1] |

TABLE 2B-continued

Structure

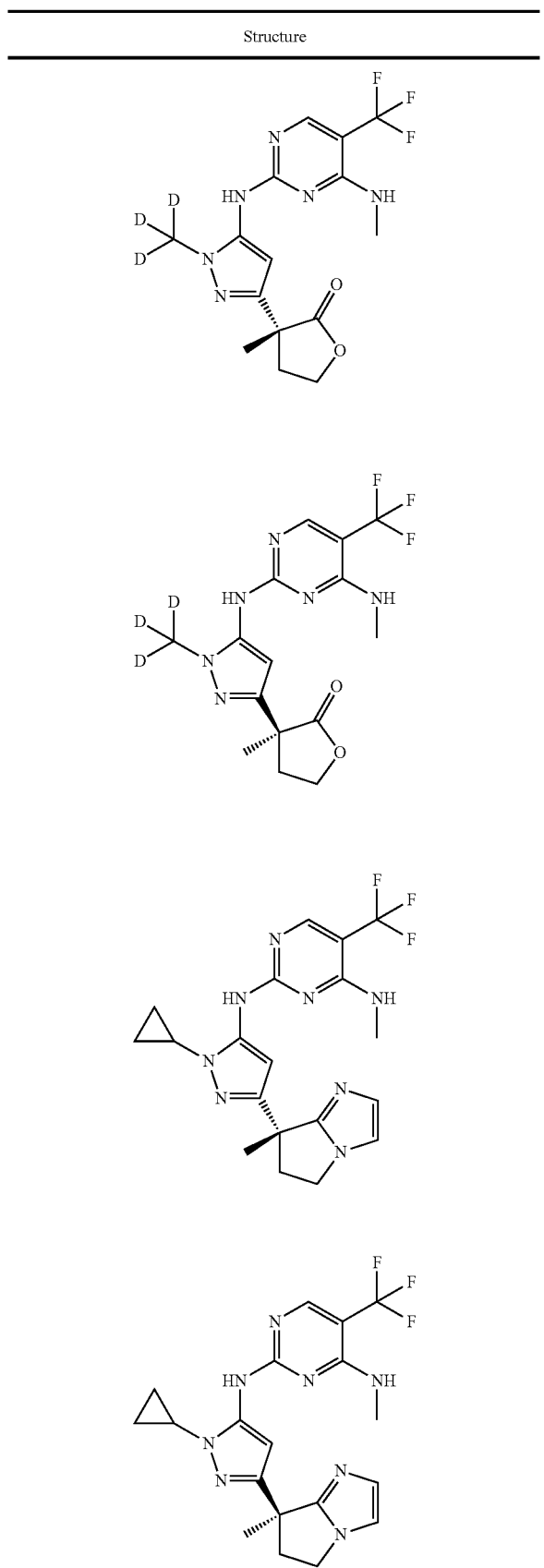
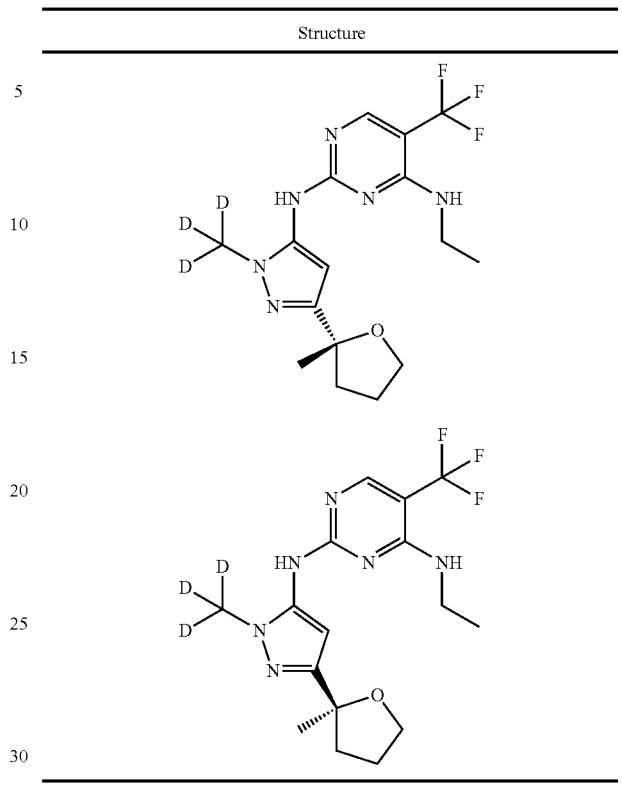

or a pharmaceutically acceptable salt, deuterated analog, prodrug, stereoisomer, or a mixture of stereoisomers thereof.

In one embodiment, a compound may be selected from those compounds in Table 2A. Also included within the disclosure are pharmaceutically acceptable salts, prodrugs, stereoisomers, or a mixture of stereoisomers thereof. In one embodiment, a compound may be selected from those compounds in Table 2B. Also included within the disclosure are pharmaceutically acceptable salts, deuterated analogs, prodrugs, stereoisomers, or a mixture of stereoisomers thereof. In certain embodiments, provided are compounds of Table 2A for use in the methods described herein. In certain embodiments, provided are compounds of Table 2B for use in the methods described herein.

3. Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, deuterated analog, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

LRRK2 has been associated with the transition from mild cognitive impairment to Alzheimer's disease; L-Dopa induced dyskinesia (Hurley et al., Eur. J, Neurosci., Vol. 26, 2007, 171-177); CNS disorders associated with neuroprogenitor cell proliferation and migration, and regulation of LRRK2 may have utility in improving neurological outcomes following ischemic injury, and stimulating restoration of CNS function following neuronal injury such as ischemic stroke, traumatic brain injury, or spinal cord injury (Milosevic et al., Neurodegen., Vol. 4, 2009, 25; See Zhang et al., J. Neurosci. Res. Vol. 88, 2010, 3275-3281); Parkinson's disease, Alzheimer's disease, multiple sclerosis, and HIV-induced dementia (See Milosevic et al., Mol. Neurodegen., Vol. 4, 2009, 25); kidney, breast, prostate (e.g. solid tumor), blood and lung cancer, and acute myeologenouse leukemia (AML); lymphomas and leukemias (See Ray et al., J. Immunolo., Vol. 230, 2011, 109); multiple myeoloma (Chapman et al., Nature, Vol. 471, 2011, 467-472); papillary renal and thyroid carcinomas; multiple myeloma (Chapman et al., Nature, Vol. 471, 2011, 467-472); diseases of the immune system, including rheumatoid arthritis, systemic lupus erythematosus autoimmune hemolytic anemia, pure red cell aplasia, idiopathic thrombocytopenic pupura (ITP), Evans syndrome, vasculitis, bullous skin disorders, type 1 diabetes mellitus, Sjogren's syndrome, Delvic's disease, and inflammatory myopathies (Nakamura et al., DNA Res. Vol. 13(4), 2006, 169-183; See Engel et al., Pharmacol. Rev. Vol. 63, 2011, 127-156; Homam et al., J. Clin. Neuromuscular Disease, Vol. 12, 2010, 91-102); ankylosing spondylitis and leprosy infection (DAnoy et al., PLoS Genetics, Vol. 6(12), 2010, e1001195, 1-5; see Zhang et al., N. Eng. J. Med. Vol. 361, 2009, 2609-2618); alpha-synucleinopathies, taupathies (See Li et al., 2010 Neurodegen. Dis. Vol. 7, 2010, 265-271); Gaucher disease (See Westbroek et al., Trends. Mol. Med. Vol. 17, 2011, 485-493); tauopathy diseases characterized by hyperphosphorylation of Tau such as argyrophilic grain disease, Pick's disease, corticobasal degeneration, progressive supranuclear palsy, and inherited frontotemporal dementia and parkinsonism linked to chromosome 17 (See Goedert, M and Jakes, R, Biochemica et Biophysica Acta, Vol. 1739, 2005, 240-250); diseases characterized by diminished dopamine levels such as withdrawal symptoms/relapse associated with drug addiction (See Rothman et al., og. Brain Res., Vol. 172, 2008, 385); microglial proinflammatory responses (See Moehle et al., J. Neuroscience Vol. 32, 2012, 1602-1611); Crohn's disease pathogenesis (see Barrett et al., Nature Genetics, Vol. 40, 2008, 955-962); and amyotrophic lateral sclerosis (ALS).

It is suggested that increased LRRK2 activity may be characteristic of ALS. Significantly elevated levels of LRRK2 mRNA have been observed in fibroblasts of Niemann-Pick Type C (NPC) disease patients, indicating abnormal LRRK2 function may play a role in lysosomal disorders.

In another aspect, the present disclosure relates to a method of treating a disease or condition mediated, at least in part, by LRRK2. In particular, the disclosure provides methods for preventing or treating a disorder associated with LRRK2 in a mammal, comprising the step of administering to said mammal a therapeutically effective amount of a compound of Table 1A or Table 1B or therapeutic preparation of the present disclosure. In some embodiments, the disease or condition mediated, at least in part, by LRRK2 is a neurodegenerative disease, for example, a central nervous system (CNS) disorder, such as Parkinson's disease (PD), Alzheimer's disease (AD), dementia (including Lewy body dementia and cascular dementia), amyotrophic lateral sclerosis (ALS), age related memory dysfunction, mild cognitive impairment (e.g., including the transition from mild cognitive impairment to Alzheimer's disease), argyrophilic grain disease, lysosomal disorders (for example, Niemann-PickType C disease, Gaucher disease) corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, Huntington's disease (HD), and HIV-associated dementia (HAD). In other embodiments, the disorder is an ischemic disease of organs including but not limited to brain, heart, kidney, and liver.

In some other embodiments, the disease or condition mediated, at least in part, by LRRK2 is cancer. In certain specific embodiments, the cancer is thyroid, renal (including papillary renal), breast, lung, blood, and prostate cancers (e.g. solid tumor), leukemias (including acute myelogenous leukemia (AML)), or lymphomas. In some embodiments, the cancer is kidney cancer, breast cancer, prostate cancer, blood cancer, papillary cancer, lung cancer, acute myelogenous leukemia, or multiple myeloma.

In other embodiments, the presently disclosed compounds are used in methods for treatment of inflammatory disorders. In some embodiments, the disorder is an inflammatory disease of the intestines, such as Crohn's disease or ulcerative colitis (both generally known together as inflammatory bowel disease). In other embodiments, the inflammatory disease is leprosy, amyotrophic lateral sclerosis, rheumatoid arthritis, or ankylosing spondylitis. In some embodiments, the inflammatory disease is leprosy, Crohn's disease, inflammatory bowel disease, ulcerative colitis, amyotrophic lateral sclerosis, rheumatoid arthritis, or ankylosing spondylitis.

In other embodiments, the presently disclosed compounds are used in methods for treatment of multiple sclerosis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease, and inflammatory myopathies.

Other embodiments include methods for enhancing cognitive memory of a subject, the method comprising administering an effective amount of a composition comprising the compound of Table 1A, Table 1B, Table 2A or Table 2B to a subject in need thereof.

Other embodiments include use of the presently disclosed compounds in therapy. Some embodiments include their use in the treatment of a neurodegenerative disease, cancer, or an inflammatory disease.

In other embodiments, provided are the presently disclosed compounds for use in the treatment of Alzheimer's disease, L-Dopa induced dyskinesia, Parkinson's disease, dementia, ALS, kidney cancer, breast cancer, prostate cancer, blood cancer, papillary cancer, lung cancer, acute myelogenous leukemia, multiple myeloma, leprosy, Crohn's disease, inflammatory bowel disease, ulcerative colitis, amyotrophic lateral sclerosis, rheumatoid arthritis, or ankylosing spondylitis.

In other embodiments, provided is the use of the presently disclosed compounds for the manufacture of a medicament for treating a neurodegenerative disease, cancer, or an inflammatory disease.

In other embodiments, provided is the use of the presently disclosed compounds for the manufacture of a medicament for treating Alzheimer's disease, L-Dopa induced dyskinesia, Parkinson's disease, dementia, amyotrophic lateral sclerosis, kidney cancer, breast cancer, prostate cancer, blood cancer, papillary cancer, lung cancer, acute myelogenous leukemia, multiple myeloma, leprosy, Crohn's disease, inflammatory bowel disease, ulcerative colitis, amyotrophic lateral sclerosis, rheumatoid arthritis, or ankylosing spondylitis.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel, and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

In certain embodiments, the present disclosure relates to compounds for inhibiting cell death, wherein the compounds are shown in Table 1A, Table 1B, Table 2A or Table 2B. In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar, and most preferably at a concentration less than 1 micromolar.

4. Kits

Provided herein are also kits that include a compound of the disclosure, or a pharmaceutically acceptable salt, deuterated analog, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, deuterated analog, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, deuterated analog, tautomer, stereoisomer, mixture of stereoisomers, prodrug, or deuterated analog thereof in a suitable container. The container may be a vial, jar, ampoule, preloaded syringe, and intravenous bag.

5. Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, deuterated analog, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, deuterated analog, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, deuterated analog, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Transdermal patches may be used to provide continuous or discontinuous infusion of the compounds described herein in controlled amounts. Transdermal patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, deuterated analog, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

6. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, a dosage of from about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Table 1A, Table 1B, Table 2A or Table 2B may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, four, or more times daily, using any suitable mode described above.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

7. Combination Therapy

In another aspect of the disclosure the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; hypertension, hypercholesterolemia and type II diabetes; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

In other embodiments, the compounds of the present disclosure can be administered in combination with an additional agent having activity for treatment of a neurodegenerative disease. For example, in some embodiments the compounds are administered in combination with one or more additional therapeutic agents useful for treatment of Parkinson's disease. In some embodiments, the additional therapeutic agent is L-dopa (e.g., Sinemet®), a dopaminergic agonist (e.g. Ropinerol or Pramipexole), a catechol-O-methyltransferase (COMT) inhibitor (e.g. Entacapone), a L-monoamine oxidase (MAO) inhibitor (e.g., selegiline or rasagiline) or an agent which increases dopamine release (e.g., Zonisamide).

The present disclosure also provides combinations of two or more compounds that inhibit cellular necrosis (e.g., a compound as disclosed herein and an additional agent for inhibiting necrosis). The present disclosure also provides combinations of one or more compounds that inhibit cellular necrosis combined with one or more additional agents or compounds (e.g., other therapeutic compounds for treating a disease, condition, or infection).

8. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of the compounds described herein may be accomplished as described in the following examples. If available, reagents may be purchased commercially, e.g. from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

General Synthesis

The following General Reaction Scheme I illustrates a general method of making the compounds disclosed herein.

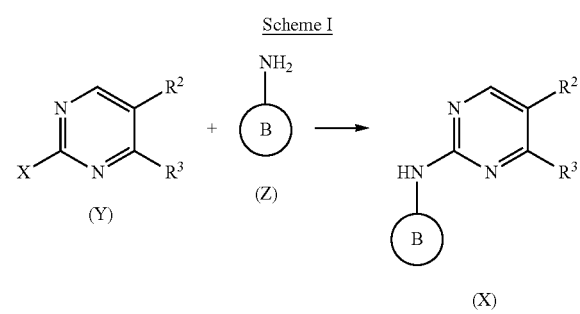

Referring to General Reaction Scheme I, compounds of formula (X) are prepared by coupling of a substituted pyrimidine of formula (Y) with an amine of formula (Z), wherein $R^2$, $R^3$, ring B and m are defined as in any of the formulas provided herein or by the specific compounds exemplified in Table 1A, Table 1B, Table 2A or Table 2B, and X is a leaving group. In certain embodiments, X is halo. Appropriate compounds of formula (Y) or (Z) can be prepared according to the more specific methods described in the Examples which follow or by methods known to one of skill in the art. Coupling of compounds of formula (Y) and (Z) in presence of an acid, provides a compound of formula (X). In some embodiments, the acid is toluene sulfonic acid or trifluroacetic acid. In some embodiments, coupling of compounds of formula (Y) and (Z) in the presence of a base provides a compound of formula (X). In some embodiments, the base is triethylamine.

In one embodiment, provided is a method of preparing a compound of formula (X) comprising coupling a compound of formula (Y) with a compound of formula (Z) under conditions to provide the compound of formula (X), wherein $R^1$, $R^2$, $R^3$, ring B and m are defined as in any of the formulas provided herein or by the specific compounds exemplified in Table 1A, Table 1B, Table 2A or Table 2B, and X is a leaving group. In certain embodiments, X is halo.

When not commercially available, amines of formula (Z) can be prepared from commercially available starting materials. For example, in certain embodiments, amines of formula (Z) can be prepared from reducing the corresponding nitro substituted compound. The amines of formula (Z) are typically functionalized prior to the coupling with the substituted pyrimidine of formula (Y). Where a certain stereoisomer is desired (e.g., a cis- or trans-stereoisomer of formula III, IIIA, or IIIB), a single stereoisomer of the corresponding amine may be prepared prior to coupling with the substituted pyrimidine of formula (Y). Each of the cis- and trans-stereoisomers can be prepared by selectively inverting the stereochemistry prior to the installation of the cyano moiety on the cyclobutyl ring. In certain embodiments, amines of formula (Z) are prepared via 1,3-dipolar cycloaddition reactions using appropriately functionalized starting materials. Further functionalization or functional group interconversion may be performed before or after the cycloaddition reaction.

In certain embodiments, compounds of formula Ia can be prepared according to Scheme II.

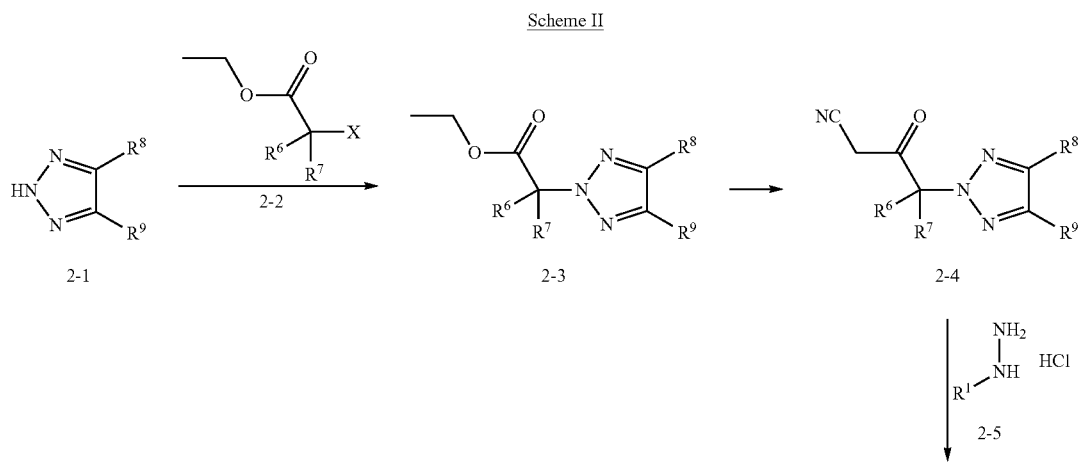

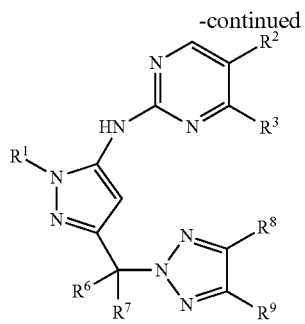
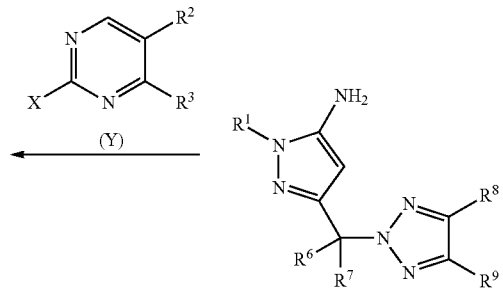

Referring to General Reaction Scheme II, compounds of formula (2-3) can be prepared by coupling appropriately substituted triazole (2-1) with appropriately substituted ester (2-2). Conversion of the ester of compound (2-3) to the α-cyanoketone compound (2-4) can be accomplished under substitution reaction conditions using a strong base (e.g., butyllithium) and acetonitrile. Contacting compound (2-4) with an appropriately substituted hydrazine (2-5) or salt thereof, provides an amine of formula (2-6). Coupling of the amine of formula (2-6) with the appropriately substituted pyrimidine of formula (Y) can be accomplished according to Scheme I, thus providing the compounds of formula Ia.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Experimental Methods:

All non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 μm pre-coated silica gel plates, visualized either with UV, or in an iodine chamber. Flash column chromatography was performed using silica gel (100-200 mesh). Chemical shifts are reported relative to chloroform (δ7.26), methanol (δ3.31), or DMSO (δ2.50) for $^1$H NMR. HPLC analysis was performed on Shimadzu 20AB HPLC system with a photodiode array detector and Luna-C18(2) 2.0×50 mm, 5 um column at a flow rate of 1.2 mL/min with a gradient solvent Mobile phase A (MPA, $H_2O$+0.037% (v/v) TFA): Mobile phase B (MPB, ACN+0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 μm; MPA: HCl/$H_2O$=0.04%, or formic acid/$H_2O$=0.2% (v/v); MPB: ACN. Neutral: Waters Xbridge 150×25.5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector. SFC analysis was performed on Thar analytical SFC system with a UV/Vis detector and series of chiral columns including AD-3, AS-H, OJ-3, OD-3, AY-3 and IC-3, 4.6×100 mm, 3 μm column at a flow rate of 4 mL/min with a gradient solvent Mobile phase A (MPA, $CO_2$): Mobile phase B (MPB, MeOH+0.05% (v/v) IPAm) (0.01 min, 10% MPB; 3 min, 40% MPB; 3.5 min, 40% MPB; 3.56-5 min, 10% MPB). SFC preparative was performed on Thar 80 preparative SFC system with a UV/Vis detector and series of chiral preparative columns including AD-H, AS-H, OJ-H, OD-H, AY-H and IC-H, 30×250 mm, Sum column at a flow rate of 65 mL/min with a gradient solvent Mobile phase A (MPA, $CO_2$): Mobile phase B (MPB, MeOH+0.1% (v/v) $NH_3H_2O$) (0.01 min, 10% MPB; 5 min, 40% MPB; 6 min, 40% MPB; 6.1-10 min, 10% MPB).

Compounds were named by using either ChemBioDraw Ultra 13.0 or chemaxon.

Compound Preparation

Where the preparation of starting materials is not described, these are commercially available, known in the literature or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

Example 1

Synthesis of N4-ethyl-N2-[1-(3-isocyanocyclobutyl)-5-methyl-pyrazol-4-yl]-5-(trifluoromethyl)pyrimidine-2,4-diamine (26)

3-(benzyloxy)cyclobutanol

To a stirring solution of 3-benzyloxycyclobutanone (125 g, 709.38 mmol) in MeOH (1.5 L) was added NaBH$_4$ (26.84 g, 709.38 mmol) portionwise at −20° C. under N$_2$ over a period of 4 h. After addition, the mixture was allowed to warm to 25° C. and stirred for 30 min. The mixture was added with water (50 mL) and stirred for 30 min. The mixture was concentrated under reduced pressure to give a residue. (Two batches of the same scale were combined to workup.) The residue was purified by silica gel column chromatography (PE:EtOAc=6:1) to afford (1S,3S)-3-(benzyloxy)cyclobutanol as a colorless oil.

1-(3-(benzyloxy)cyclobutyl)-4-nitro-1H-pyrazole

To a mixture of (1S,3S)-3-(benzyloxy)cyclobutanol (250 g, 1.40 mol) and 4-nitro-1H-pyrazole (158.3 g, 1.40 mol) in THF (5 L) was added PPh$_3$ (477.37 g, 1.82 mol) and DIAD (368.02 g, 1.82 mol, 353.87 mL) dropwise at 0° C. under N$_2$. After addition, the mixture was stirred at 25° C. for 16 h. The mixture was concentrated in reduced pressure to give a residue. The residue was triturated with PE:EtOAc=2:1 (2 L) and filtered. The filter cake was washed with PE:EtOAc=2:1 (2×1 L) and the combined filtrate were concentrated to afford a crude product. The crude product was purified by silica gel column chromatography (PE:EtOAc=6:1) to afford 1-((1R,3R)-3-(benzyloxy)cyclobutyl)-4-nitro-1H-pyrazole as a white solid. LCMS: RT 0.851 min, m/z=274.2 [M+H]$^+$. $^1$H NMR (400 MHz, CDCl$_3$) δ 8.15 (s, 1H), 8.12 (s, 1H), 7.29-7.41 (m, 5H), 4.92-4.99 (m, 1H), 4.49 (s, 2H), 4.41-4.47 (m, 1H), 2.63-2.84 (m, 4H).

1-(3-(benzyloxy)cyclobutyl)-5-chloro-4-nitro-1H-pyrazole

To a solution of 1-((1R,3R)-3-(benzyloxy)cyclobutyl)-4-nitro-1H-pyrazole (80 g, 292.73 mmol) in THF (1.6 L) was added LiHMDS (1 M, 567.90 mL) dropwise at −75° C. under N$_2$ over a period of 1 h. After addition, the mixture was stirred for 1 h, then the solution of 1,1,1,2,2,2-hexachloroethane (83.16 g, 351.28 mmol) in THF (200 mL) was added drop wise at −78° C. The mixture was stirred at −78° C. and stirred for 1 h. The mixture was poured into aqueous NH$_4$Cl (1.5 L). The organic phase was separated and the aqueous phase was extracted with EtOAc (2×500 mL). The combined organic phase was washed with brine (1 L), dried with anhydrous Na$_2$SO$_4$, filtered and concentrated under reduced pressure. The residue was purified by silica gel column chromatography (PE:EtOAc=10:1) to afford 14(1R,3R)-3-(benzyloxy)cyclobutyl)-5-chloro-4-nitro-1H-pyrazole as a white solid. $^1$H NMR (400 MHz, CDCl$_3$) δ 8.21 (s, 1H), 7.29-7.41 (m, 5H), 5.16-5.24 (m, 1H), 4.50 (s, 2H), 4.42-4.47 (m, 1H), 2.81-2.89 (m, 2H), 2.61-2.70 (m, 2H).

1-(3-(benzyloxy)cyclobutyl)-5-methyl-4-nitro-1H-pyrazole

To a mixture of 1-((1R,3R)-3-(benzyloxy)cyclobutyl)-5-chloro-4-nitro-1H-pyrazole (65 g, 211.22 mmol), 2,4,6-trimethyl-1,3,5,2,4,6-trioxatriborinane (212.12 g, 844.90 mmol, 235.69 mL) and Na$_2$CO$_3$ (44.78 g, 422.45 mmol) in 1,4-dioxane (1.5 L) and H$_2$O (150 mL) was added Pd(dppf)Cl$_2$.CH$_2$Cl$_2$ (27.6 g, 33.80 mmol) at 25° C. under N$_2$. The mixture was then heated to 100° C. and stirred for 40 h. The mixture was cooled to 25° C. and concentrated under reduced pressure to dryness. The residue was dissolved in PE:EtOAc=2:1 (2 L), then added with anhydrous Na$_2$SO$_4$ (100 g), celite (100 g) and stirred for 30 min. The mixture was filtered through a pad of celite. The filter cake was washed with PE:EtOAc=2:1 (2×1 L) and the filtrate was concentrated under reduced pressure to give a residue. The residue was purified by silica gel column chromatography (PE:EtOAc=10:1) to afford 1-(1R,3R)-3-(benzyloxy)cyclobutyl)-5-methyl-4-nitro-1H-pyrazole as a white solid. LCMS: RT 0.844 min, m/z=288.2 [M+H]$^+$.

3-(5-methyl-4-nitro-1H-pyrazol-1-yl)cyclobutanol

To a solution of 1-(1R,3R)-3-(benzyloxy)cyclobutyl)-5-methyl-4-nitro-1H-pyrazole (59.5 g, 207.09 mmol) in DCM (1.2 L) was added BCl$_3$ (1 M, 621.27 mL) dropwise at 0° C. under N$_2$ over a period of 2 h. The mixture was then stirred at 0° C. for 1 h. The mixture was poured into ice-water (600 mL). The aqueous phase was extracted with DCM (2×600 mL). The combined organic phase was washed with aqueous NaHCO$_3$ (500 mL), brine (500 mL), dried with anhydrous Na$_2$SO$_4$, filtered and concentrated under reduced pressure. (Four batches of the same scale were combined to workup) The residue was purified by silica gel column chromatography (PE:EtOAc=1:1) to afford (1R,3R)-3-(5-methyl-4-nitro-1H-pyrazol-1-yl)cyclobutanol as white solid. $^1$H NMR (400 MHz, CDCl$_3$) δ 8.10 (br d, J=4.63 Hz, 1H), 4.98-5.03 (m, 1H), 4.70-4.82 (m, 1H), 2.85-2.97 (m, 2H), 2.59-2.66 (m, 3H), 2.47-2.58 (m, 2H), 2.38 (br s, 1H).

1-(3-iodocyclobutyl)-5-methyl-4-nitro-1H-pyrazole

To a mixture of (1R,3R)-3-(5-methyl-4-nitro-1H-pyrazol-1-yl)cyclobutanol (70 g, 354.99 mmol), PPh$_3$ (139.66 g, 532.49 mmol) and imidazole (36.25 g, 532.49 mmol) in THF (1.2 L) was added the solution of I$_2$ (135.15 g, 532.49 mmol) in THF (200 mL) dropwise at 0° C. under N$_2$. After that the mixture was stirred at 25° C. for 16 h. The mixture was poured into ice-water (500 mL). The aqueous phase was extracted with EtOAc (2×300 mL). The combined organic phase was washed with brine (500 mL), dried with anhydrous Na$_2$SO$_4$, filtered and concentrated under reduced pressure. The residue was purified by silica gel column chromatography (PE:EtOAc=10:1) to afford 1-((1R,3R)-3-iodocyclobutyl)-5-methyl-4-nitro-1H-pyrazole as white solid. $^1$H NMR (400 MHz, CDCl$_3$) δ 8.14 (s, 1H), 4.61-4.83 (m, 1H), 4.12-4.34 (m, 1H), 3.09-3.36 (m, 4H), 2.61 (s, 3H).

3-(5-methyl-4-nitro-pyrazol-1-yl)cyclobutanecarbonitrile

To a solution of 1-(3-iodocyclobutyl)-5-methyl-4-nitro-pyrazole (2 g, 6.51 mmol) in DMF (30 mL) was added KCN (2.5 g, 39.06 mmol) at 0° C. Then the mixture was stirred at 70° C. for 2 days. The mixture was diluted with water (60 mL), extracted with EtOAc (4×20 mL). The combined organic layers were washed with water (2×50 mL), brine (50 mL), dried over Na$_2$SO$_4$, filtered and concentrated. The crude product was purified by silica gel column chromatography (PE:EtOAc=1:0 to 1:1) to give 3-(5-methyl-4-nitro-pyrazol-1-yl)cyclobutanecarbonitrile as a yellow solid. LCMS: RT 1.066 min, m/z=207.3 [M+H]$^+$. $^1$H NMR (400 MHz, CDCl$_3$) δ ppm 8.16 (s, 1H), 5.11 (quin, J=7.81 Hz, 1H), 3.32-3.47 (m, 1H), 3.08-3.21 (m, 2H), 2.85-2.95 (m, 2H), 2.67 (s, 3H), 1.59 (s, 1H).

3-(4-amino-5-methyl-pyrazol-1-yl)cyclobutanecarbonitrile

To a mixture of 3-(5-methyl-4-nitro-pyrazol-1-yl)cyclobutanecarbonitrile (200 mg, 969.93 µmol), NH$_4$Cl (259 mg, 4.85 mmol) in the mixture of EtOH (4.8 mL) and H$_2$O (1.2 mL) was added Fe (270 mg, 4.85 mmol) at 15° C. The mixture was stirred at 80° C. for 2 h. The mixture was filtered and the filtrate was concentrated under reduced pressure. The residue was diluted with water (10 mL), extracted with EtOAc (10×5 mL). The combined organic layers were dried over Na$_2$SO$_4$, filtered and concentrated to give 3-(4-amino-5-methyl-pyrazol-1-yl)cyclobutanecarbonitrile. LCMS: RT 0.101 min, m/z=177.2 [M+H]$^+$.

2-chloro-N-ethyl-5-(trifluoromethyl)pyrimidin-4-amine

To a solution of 2,4-dichloro-5-(trifluoromethyl)pyrimidine (70 g, 322.61 mmol) in THF (1.4 L) was added a solution of ethanamine (32 g, 709.74 mmol, 46.37 mL) in THF (100 mL) dropwise at 0° C. under N$_2$ over a period of 1 h. After addition, the mixture was stirred at 25° C. for 1 h. The mixture was filtered and concentrated under reduced pressure to afford a residue. The residue was triturated with DCM (200 mL) and filtered. The filtrate was recrystallized with n-heptane (600 mL) and MTBE (400 mL). The precipitated phase was syrup. The liquid was discarded. The syrup residue was purified by silica gel column chromatography (PE:EtOAc=20:1) to afford 2-chloro-N-ethyl-5-(trifluoromethyl)pyrimidin-4-amine as a white solid. $^1$H NMR (400 MHz, CDCl$_3$): δ 8.22-8.27 (m, 1H), 5.40 (br s, 1H), 3.56-3.65 (m, 2H), 1.29 (t, J=7.22 Hz, 3H). HPLC: RT: 2.68 min.

N4-ethyl-N$_2$-[1-(3-isocyanocyclobutyl)-5-methyl-pyrazol-4-yl]-5-(trifluoromethyl)pyrimidine-2,4-diamine A mixture of 1-(3-isocyanocyclobutyl)-5-methyl-pyrazol-4-amine (170 mg, 964.70 μmol), 2-chloro-N-ethyl-5-(trifluoromethyl)pyrimidin-4-amine (217 mg, 964.70 μmol), p-TsOH.H$_2$O (55 mg, 289.41 μmol) in 1,4-dioxane (10 mL) was stirred at 90° C. for 2 h. The mixture was concentrated under reduced pressure. The residue was diluted with water (20 mL), extracted with EtOAc (3×10 mL). The combined organic layers were washed with water (30 mL), brine (30 mL), dried over Na$_2$SO$_4$, filtered and concentrated. The crude product was purified by prep-TLC (DCM:MeOH=15:1) to give N4-ethyl-N$_2$-[1-(3-isocyanocyclobutyl)-5-methyl-pyrazol-4-yl]-5-(trifluoromethyl)pyrimidine-2,4-diamine $^1$H NMR (400 MHz, CDCl$_3$) δ ppm 8.10 (s, 1H), 7.65-7.93 (m, 1H), 6.15-6.60 (m, 1H), 4.91-5.15 (m, 2H), 3.44-3.55 (m, 2H), 3.23-3.35 (m, 1H), 3.07-3.21 (m, 2H), 2.75-2.89 (m, 2H), 2.20 (s, 3H), 1.61 (br s, 1H), 1.25 (t, J=7.1 Hz, 3H). HPLC: RT: 1.73 min. MS: m/z=366.2 [M+H]$^+$.

Example 2

Synthesis of [9]N4-ethyl-N2-[1-($^2$H$_3$))methyl-3-[2-(2H-1,2,3-triazol-2-yl)propan-2-yl]-1H-pyrazol-5-yl]-5-(trifluoromethyl)pyrimidine-2,4-diamine (34)

Ethyl 2-methyl-2-(2H-1,2,3-triazol-2-yl)propanoate

To a mixture of 2H-triazole (20 g, 289.56 mmol) in DMF (200 mL) was added t-BuOK (48.74 g, 434.34 mmol) at 0° C. After the addition, ethyl 2-bromo-2-methyl-propanoate (78.63 g, 434.34 mmol) was added dropwise at 0° C., then the mixture was stirred at 25° C. for 3 h. The mixture was poured into ice-water (70 mL) and stirred for 5 min. The aqueous phase was extracted with EtOAc (3×300 mL). The combined organic phase was washed with brine (2×200 mL), dried with anhydrous Na$_2$SO$_4$, filtered and concentrated under reduced pressure. The residue was purified by silica gel column chromatography (PE:EtOAc=3:1) to give ethyl 2-methyl-2-(1H-1,2,3-triazol-1-yl)propanoate and isomer ethyl 2-methyl-2-(2H-1,2,3-triazol-1-yl)propanoate. LCMS: RT 0.565 min, m/z=184.1 [M+H]$^+$. $^1$H NMR (400 MHz, CDCl$_3$): δ ppm 7.64 (s, 2H), 4.12-4.18 (m, 2H), 1.95 (s, 6H), 1.18 (t, J=7.28 Hz, 3H). Undesired isomer, ethyl 2-methyl-2-(1H-1,2,3-triazol-1-yl)propanoate. $^1$H NMR (400 MHz, CDCl$_3$): δ ppm 7.70 (d, J=6.40 Hz, 2H), 4.14-4.19 (m, 2H), 1.94 (s, 6H), 1.20 (t, J=7.28 Hz, 3H).

4-Methyl-3-oxo-4-(2H-1,2,3-triazol-2-yl)pentanenitrile

To a mixture of MeCN (96.88 mg, 2.36 mmol) in THF (10 mL) was added n-BuLi (2.5 M, 0.94 mL) dropwise at −78° C. under N$_2$. After 0.5 h, ethyl 2-methyl-2-(2H-1,2,3-triazol-1-yl)propanoate (200 mg, 2.36 mmol) was added dropwise over 1 h at −78° C., then the reaction was stirred at −78° C. for 2 h. The mixture was poured into ice-water (20 mL) and stirred for 5 min. The mixture was adjusted to pH=5~6 by HCl (1 M). The aqueous phase was extracted with ethyl acetate EtOAc (3×10 mL). The combined organic phase was washed with brine (10 mL), dried with anhydrous Na$_2$SO$_4$, filtered and concentrated. The residue was purified by silica gel column chromatography (PE:EtOAc=10:1 to 1:1) to give 4-methyl-3-oxo-4-(2H-1,2,3-triazol-2-yl)pentanenitrile. LCMS: RT 0.945 min, m/z=179.1 [M+H]$^+$. $^1$H NMR (400 MHz, CDCl$_3$): δ ppm 7.76 (s, 1H), 3.11 (s, 2H), 1.90 (s, 6H).

1-($^2$H$_3$)Methyl-3-[2-(2H-1,2,3-triazol-2-yl)propan-2-yl]-1H-pyrazol-5-amine

To a solution of 4-methyl-3-oxo-4-(2H-1,2,3-triazol-2-yl)pentanenitrile (250 mg, 1.4 mmol), trideuteriomethylhydrazine (512.4 mg, 4.2 mmol 2HCl, equiv) in EtOH (20 mL) was added dropwise TEA (992 mg, 9.8 mmol, 1.36 mL, 7 equiv) at 0° C. After addition, the mixture was stirred at 95° C. for 4 h. The reaction mixture was concentrated to get a residue, which was diluted with H$_2$O (5 mL) and extracted with EtOAc (3×5 mL), dried over Na$_2$SO$_4$, filtered and concentrated under reduced pressure to give 1-($^2$H$_3$)methyl-3-[2-(2H-1,2,3-triazol-2-yl)propan-2-yl]-1H-pyrazol-5-amine. LCMS: RT 0.236 min, m/z=210.2 [M+H]$^+$. $^1$H NMR (400 MHz, CDCl$_3$): δ ppm 7.61 (s, 1H), 5.25 (s, 1H), 3.39 (br s, 1H), 2.05 (s, 3H).

N4-Ethyl-N$_2$-[1-($^2$H$_3$)methyl-3-[2-(2H-1,2,3-triazol-2-yl)propan-2-yl]-1H-pyrazol-5-]-5-(trifluoromethyl)pyrimidine-2,4-diamine To a solution of 1-($^2$H$_3$)methyl-3-[2-(2H-1,2,3-triazol-2-yl)propan-2-yl]-1H-pyrazol-5-amine (100 mg, 477.85 μmol) and 2-chloro-N-ethyl-5-(trifluoromethyl)pyrimidin-4-amine (107.8 mg, 477.85 μmol) in 1,4-dioxane (10 mL) was added p-TsOH (24.69 mg, 143.36 μmol). The mixture was stirred at 90° C. for 3 h. The reaction mixture was concentrated under reduced pressure. The residue was diluted with H$_2$O (5 mL) and adjusted to pH=8-9 with aq. NaHCO$_3$ and extracted with EtOAc (3×8 mL). The combined organic layers were washed with brine (10 mL), dried over Na$_2$SO$_4$, filtered and concentrated under reduced pressure. The residue was purified by prep-TLC (PE:EtOAc=1:1) and trituration with n-heptane to give N4-ethyl-N$_2$-[1-($^2$H$_3$)methyl-3-[2-(2H-1,2,3-triazol-2-yl)propan-2-yl]-1H-pyrazol-5-yl]-5-(trifluoromethyl)pyrimidine-2,4-diamine. $^1$H NMR (400 MHz, CDCl$_3$): δ ppm 8.10 (s, 1H), 7.62 (s, 2H), 6.73 (br s, 1H), 6.03 (s, 1H), 5.15 (br s, 1H), 3.35-3.44 (m, 2H), 2.11 (s, 6H), 1.18-1.21 (t, J=7.28 Hz, 3H). HPLC: RT 2.24 min, m/z: 399.2 [M+H]$^+$.

Example 3

Synthesis of N2-[2-cyclopropyl-5-[1-methyl-1-(triazol-2-yl)ethyl]pyrazol-3-yl]-N4-ethyl-5-(trifluoromethyl)pyrimidine-2,4-diamine (78)

4-methyl-3-oxo-4-(triazol-2-yl)pentanenitrile

To a mixture of 2H-triazole (20 g, 289.56 mmol) in DMF (200 mL) was added t-BuOK (48.74 g, 434.34 mmol) in one portion at 0° C. under $N_2$. After addition, methyl 2-bromo-2-methyl-propanoate (78.63 g, 434.34 mmol, 56.16 mL) was added dropwise. The mixture was stirred at 25° C. for 3 h. The residue was poured into ice-water (700 mL) and stirred for 5 min. The aqueous phase was extracted with EtOAc (3×300 mL). The combined organic phase was washed with brine (2×100 mL), dried over anhydrous $Na_2SO_4$, filtered and concentrated under reduced pressure. The residue was purified by silica gel column chromatography (PE:EtOAc=10:1 to 3:1) to give methyl 2-methyl-2-(triazol-2-yl)propanoate as a yellow oil. $^1$H NMR (400 MHz, CDCl$_3$): δ ppm 7.649 (s, 2H), 3.701 (s, 3H), 1.963 (s, 6H).

4-methyl-3-oxo-4-(triazol-2-yl)pentanenitrile

To a solution of CH$_3$CN (485.21 mg, 11.82 mmol) in THF (20 mL) was added dropwise n-BuLi (2.5 M, 4.73 mL) at −78° C. over 10 min. After addition, the mixture was stirred at this temperature for 50 min, and then methyl 2-methyl-2-(triazol-2-yl)propanoate (1 g, 5.91 mmol) was added dropwise at −78° C. The resulting mixture was stirred at −78° C. for 2 h. The reaction mixture was poured into ice-water (50 mL), adjusted to pH=5-6 with HCl (1N) and extracted with EtOAc (3×20 mL). The combined organic layers were washed with brine (10 mL), dried over Na$_2$SO$_4$, filtered and concentrated under reduced pressure. The residue was purified by silica gel column chromatography (PE:EtOAc=10:1 to 1:1) to give 4-methyl-3-oxo-4-(triazol-2-yl)pentanenitrile as a yellow solid. $^1$H NMR (400 MHz, CDCl$_3$): δ ppm 7.761 (s, 2H), 3.106 (s, 2H), 1.904 (s, 6H).

2-cyclopropyl-5-[1-methyl-1-(triazol-2-yl)ethyl]pyrazol-3-amine

To a mixture of 4-methyl-3-oxo-4-(triazol-2-yl)pentanenitrile (400 mg, 2.24 mmol) and cyclopropylhydrazine dihydrochloride (974.6 mg, 6.72 mmol) in EtOH (10 mL) was added HCl (12 M, 560 μL) at 25° C. under $N_2$. The mixture was stirred at 90° C. for 12 h. The mixture was concentrated. The residue was poured into aq. NaHCO$_3$ (10 mL) and stirred for 5 min. The aqueous phase was extracted with EtOAc (3×5 mL). The combined organic phase was dried with anhydrous Na$_2$SO$_4$, filtered and concentrated under reduced pressure. The residue was purified by prep-TLC (PE:EtOAc=1/1) to give 2-cyclopropyl-5-[1-methyl-1-(triazol-2-yl)ethyl]pyrazol-3-amine as a yellow oil. $^1$H NMR: (400 MHz, CDCl$_3$): δ ppm 7.756-7.722 (d, J=13.6 Hz, 1H), 7.616 (s, 1H), 2.041 (s, 6H), 1.1391.100 (m, 2H), 1.022-1.004 (m, 2H).

N$_2$-[2-cyclopropyl-5-[1-methyl-1-(triazol-2-yl)ethyl]pyrazol-3-yl]-N4-ethyl-5-(trifluoromethyl)pyrimidine-2,4-diamine A mixture of 2-cyclopropyl-5-[1-methyl-1-(triazol-2-yl)ethyl]pyrazol-3-amine (77 mg, 331.5 μmol), 2-chloro-N-ethyl-5-(trifluoromethyl)pyrimidin-4-amine (74.79 mg, 331.5 μmol) and p-TsOH.H$_2$O (31.53 mg, 165.75 μmol) in 1,4-dioxane (10 mL) was stirred at 90° C. for 3 h under $N_2$. The reaction mixture was quenched by sat. NaHCO$_3$ (10 mL) and extracted with EtOAc (2×10 mL). The combined organic layers were washed with brine (10 mL), dried over Na$_2$SO$_4$, filtered and concentrated under reduced pressure. The residue was purified by prep-TLC (SiO$_2$, PE:EtOAc=1:1) and further purification by prep-HPLC (FA) to give N2-[2-cyclopropyl-5-[1-methyl-1-(triazol-2-yl)ethyl]pyrazol-3-yl]-N4-ethyl-5-(trifluoromethyl)pyrimidine-2,4-diamine $^1$H NMR (400 MHz, CDCl$_3$): δ 8.13 (s, 1H), 7.62 (s, 2H), 7.30 (br s, 1H), 6.13 (s, 1H), 5.18 (br s, 1H), 3.38-3.47 (m, 2H), 3.24 (tt, J=3.59, 6.95 Hz, 1H), 2.10 (s, 6H), 1.24 (t, J=7.22 Hz, 3H), 1.09-1.21 (m, 4H). HPLC: RT 2.61 min. MS: m/z: 422.3 [M+H]$^+$.

Example 4

Synthesis of (3S)- and (3R)-3-[1-cyclopropyl-5-[[4-(ethylamino)-5-(trifluoromethyl)pyrimidin-2-yl]amino]pyrazol-3-yl]-3-methyl-tetrahydrofuran-2-one (143 and 144)

Tert-butyl N-(1-methylcyclopropyl)carbamate

To a mixture of sodium (5.34 g, 232.32 mmol) in diethyl carbonate (50 mL) was added a solution of tetrahydrofuran-2-one (20 g, 232.32 mmol) in diethyl carbonate (25 mL) at 100° C. over a period of 3 h. The mixture was cooled to 20° C. and quenched by ice sat. NH$_4$Cl, then adjusted to pH=5 by adding 1N HCl. The aqueous phase was extracted with EtOAc (3×30 mL). The combined organic phase was washed with brine (2×20 mL), dried over anhydrous Na$_2$SO$_4$, filtered and concentrated under reduced pressure. The residue was purified by silica gel column chromatography (PE:EtOAc=10:1 to 0:1) to give ethyl 2-oxotetrahydrofuran-3-carboxylate as a light yellow oil. $^1$H NMR (400 MHz, CDCl$_3$): δ ppm 4.49 (td, J=8.47, 5.52 Hz, 1H), 4.34 (dt, J=8.69, 7.45 Hz, 1H), 4.24-4.30 (m, 2H), 3.55 (dd, J=9.35, 7.59 Hz, 1H), 2.69 (dq, J=13.07, 7.57 Hz, 1H), 2.51 (dddd, J=13.08, 9.32, 7.59, 5.52 Hz, 1H), 1.32 (t, J=7.09 Hz, 3H).

Ethyl 3-methyl-2-oxo-tetrahydrofuran-3-carboxylate

To a solution of ethyl 2-oxotetrahydrofuran-3-carboxylate (6.9 g, 43.63 mmol) in THF (150 mL) was added NaH (1.92 g, 47.99 mmol, 60% purity) at 0° C. over 30 min. After addition, the mixture was stirred at 20° C. for 30 min, and then MeI (9.29 g, 65.45 mmol, 4.07 mL) was added dropwise at 0° C. over 30 min. The resulting mixture was stirred at 20° C. for 10.5 h. The reaction mixture was poured into aqueous sat. NH$_4$Cl solution at 0° C. and extracted with EtOAc (3×50 mL). The combined organic layers were washed with brine (30 mL), dried over anhydrous Na$_2$SO$_4$, filtered and concentrated under reduced pressure. The residue was purified by silica gel column chromatography (PE:EtOAc=20:1 to 1:1) to give ethyl 3-methyl-2-oxo-tetrahydrofuran-3-carboxylate as a yellow oil. $^1$H NMR (400 MHz, CDCl$_3$): δ ppm 4.32-4.44 (m, 2H) 4.24 (q, J=7.20 Hz, 2H), 2.76 (ddd, J=13.01, 7.06, 4.19 Hz, 1H), 2.20 (dt, J=13.23, 8.38 Hz, 1H), 1.54 (s, 3H), 1.30 (t, J=7.17 Hz, 3H).

3-(3-methyl-2-oxo-tetrahydrofuran-3-yl)-3-oxo-propanenitrile

To a solution of CH$_3$CN (1.2 g, 30.03 mmol, 1.58 mL) in THF (50 mL) was added dropwise n-BuLi (12.01 mL, 2.5

M) at −78° C. over 30 min under N$_2$. After addition, the mixture was stirred at this temperature for 30 min. The suspension mixture was added dropwise to a solution of ethyl 3-methyl-2-oxo-tetrahydrofuran-3-carboxylate (4.7 g, 27.30 mmol) in THF (50 mL) at −78° C. for 30 min. The resulting mixture was warmed to −40° C. and stirred at −40° C. for 1.5 h. The reaction mixture was quenched by addition of sat. NH$_4$Cl at 0° C., and then adjusted to pH=4-5 with 1N HCl and extracted with EtOAc (3×50 mL). The combined organic layers were washed with brine (20 mL), dried over anhydrous Na$_2$SO$_4$, filtered and concentrated under reduced pressure to give 3-(3-methyl-2-oxo-tetrahydrofuran-3-yl)-3-oxo-propanenitrile as a yellow solid, which was used in next step without further purification. $^1$H NMR (400 MHz, CDCl$_3$): δ ppm 4.29-4.46 (m, 2H), 3.79-4.12 (m, 2H), 3.03 (ddd, J=13.40, 7.55, 6.17 Hz, 1H), 2.10 (dt, J=13.73, 7.14 Hz, 1H), 1.60 (s, 3H).

3-(5-amino-1-cyclopropyl-pyrazol-3-yl)-3-methyl-tetrahydrofuran-2-one

A mixture of 3-(3-methyl-2-oxo-tetrahydrofuran-3-yl)-3-oxo-propanenitrile (200 mg, 1.2 mmol) and cyclopropylhydrazine dihydrochloride salt (174 mg, 1.2 mmol) in i-PrOH (5 mL) was stirred at 50° C. for 16 h under N$_2$. The reaction solution was adjusted to pH=7 with sat. NaHCO$_3$, extracted with EtOAc (3×5 mL). The organic layers were combined, washed with brine (5 mL), dried over anhydrous Na$_2$SO$_4$, filtered and concentrated under reduced pressure. The crude product was purified by prep-TLC (DCM:MeOH=10:1) to give 3-(5-amino-1-cyclopropyl-pyrazol-3-yl)-3-methyl-tetrahydrofuran-2-one as a yellow oil. $^1$H NMR (400 MHz, CDCl$_3$): δ ppm 5.47 (s, 1H), 4.24-4.41 (m, 2H), 3.76-3.94 (br, 2H), 3.04-3.14 (m, 1H), 2.89-3.02 (m, 1H), 2.12-2.28 (m, 1H), 1.53 (s, 3H), 0.95-1.04 (m, 4H).

(3S) and (3R) N$_2$-[5-cyclopropyl-1-[3-(triazol-2-yl)cyclobutyl]pyrazol-4-yl]-N4-ethyl-5-(trifluoromethyl)pyrimidine-2,4-diamine To a solution of 3-(5-amino-1-cyclopropyl-pyrazol-3-yl)-3-methyl-tetrahydrofuran-2-one (90 mg, 406.76 µmol) in 1,4-dioxane (5 mL) was added 2-chloro-N-ethyl-5-(trifluoromethyl)pyrimidin-4-amine (91.77 mg, 406.76 µmol) and p-TsOH (14.01 mg, 81.35 µmol). The mixture was stirred at 90° C. for 10 h. The reaction solution was adjusted to pH=7 with sat.NaHCO$_3$, extracted with EtOAc (3×5 mL). The organic layers were combined, washed with brine (5 mL), dried over anhydrous Na$_2$SO$_4$, filtered and concentrated under reduced pressure. The crude product was purified by prep-TLC (PE:EtOAc=1:1) to give a mixtures of enantiomers, which were separated by SFC.
First Eluting Isomer:
$^1$H NMR (400 MHz, CDCl$_3$): δ ppm 8.09 (s, 1H), 7.16 (br s, 1H), 6.55 (s, 1H), 5.17 (br s, 1H), 4.20-4.32 (m, 2H), 3.48-3.57 (m, 2H), 3.12-3.20 (m, 1H), 2.93 (ddd, J=12.58, 6.49, 4.02 Hz, 1H), 2.19 (dt, J=12.58, 8.52 Hz, 1H), 1.53 (s, 3H), 1.24 (t, J=7.22 Hz, 3H), 1.02-1.13 (m, 4H). HPLC: RT: 2.33 min. MS: m/z: 411.2 [M+H]$^+$.
Second Eluting Isomer:
$^1$H NMR (400 MHz, CDCl$_3$): δ ppm 8.17 (d, J=0.75 Hz, 1H), 7.28 (br s, 1H), 6.62 (s, 1H), 5.26 (br s, 1H), 4.28-4.42 (m, 2H), 3.55-3.66 (m, 2H), 3.17-3.28 (m, 1H), 3.01 (ddd, J=12.61, 6.46, 4.02 Hz, 1H), 2.26 (dt, J=12.55, 8.47 Hz, 1H), 1.53-1.64 (m, 3H), 1.32 (t, J=7.22 Hz, 3H), 1.10-1.21 (m, 5H). HPLC: RT: 2.33 min. MS: m/z: 411.2 [M+H]$^+$.

Example 5

Synthesis of 1-(1-cyclopropyl-5-((4-(ethylamino)-5-(trifluoromethyl)pyrimidin-2-yl)amino)-1H-pyrazol-3-yl)pyrrolidin-2-one (153)

1-cyclopropyl-1H-pyrazole-3,5-diamine

A mixture of propanedinitrile (6.15 g, 93.09 mmol) and cyclopropylhydrazine (9 g, 62.06 mmol, 2HCl salt) in i-PrOH (10 mL) was heated at 105° C. for 5 h. The reaction solution was cooled to 0° C., adjusted to pH=7 with sat. NaHCO$_3$, concentrated under reduced pressure. The crude product was purified by silica gel column chromatography (DCM:MeOH=30:1 to 10:1) to give 1-cyclopropylpyrazole-3,5-diamine as a brown syrup. $^1$H NMR (400 MHz, CDCl$_3$): δ ppm 4.88 (s, 1H), 3.80 (br s, 2H), 2.98 (tt, J=6.89, 3.47 Hz, 1H), 2.84 (br s, 2H), 1.05 (dq, J=7.86, 3.70 Hz, 2H), 0.93-1.00 (m, 2H).

N-(5-amino-1-cyclopropyl-1H-pyrazol-3-yl)-4-chlorobutanamide

To a solution of 1-cyclopropylpyrazole-3,5-diamine (2.25 g, 16.28 mmol) and TEA (3.29 g, 32.56 mmol) in DCM (200 mL) was added dropwise 4-chlorobutanoyl chloride (2.07 g, 14.65 mmol) at 0° C. for 30 min. The mixture was stirred at 0° C. for 30 min and stirred at 15° C. for 1 h. The reaction mixture was diluted with H$_2$O (50 mL) and extracted with DCM:i-PrOH (V:V=3:1, 3×30 mL). The combined organic layers were dried over Na$_2$SO$_4$, filtered and concentrated under reduced pressure. The residue was purified by silica gel column chromatography (PE:EtOAc=10:1 to 0:1) to give N-(5-amino-1-cyclopropyl-pyrazol-3-yl)-4-chloro-butanamide as a yellow oil. $^1$H NMR (400 MHz, CDCl$_3$): δ ppm 7.97 (br s, 1H), 5.94 (s, 1H), 3.90 (br s, 2H), 3.63 (t, J=6.21 Hz, 2H), 3.08 (tt, J=6.82, 3.59 Hz, 1H), 2.49 (t, J=7.09 Hz, 2H), 2.16 (quin, J=6.62 Hz, 2H), 0.93-1.13 (m, 4H).

1-(5-amino-1-cyclopropyl-1H-pyrazol-3-yl)pyrrolidin-2-one

To a solution of N-(5-amino-1-cyclopropyl-pyrazol-3-yl)-4-chloro-butanamide (1.3 g, 5.36 mmol) in THF (390 mL) was added NaH (536 mg, 13.40 mmol, 60% purity) at 0° C. over 10 min. After addition, the mixture was stirred at 0° C. for 20 min, and then stirred at 15° C. for 1.5 h. The reaction mixture was quenched by addition of aq. NH$_4$Cl (100 mL) at 0° C., and then extracted with DCM:i-PrOH (V:V=3:1, 3×100 mL). The combined organic layers were dried over Na$_2$SO$_4$, filtered and concentrated under reduced pressure. The residue was purified by silica gel column chromatography (PE:EtOAc=10:1 to 0:1) to give 1-(5-amino-1-cyclopropyl-pyrazol-3-yl)pyrrolidin-2-one as an off-white solid. $^1$H NMR (400 MHz, CDCl$_3$): δ ppm 6.10 (s, 1H), 3.89 (t, J=7.06 Hz, 4H), 3.10 (tt, J=6.86, 3.61 Hz, 1H), 2.52 (t, J=8.05 Hz, 2H), 2.11 (quin, J=7.61 Hz, 2H), 1.06-1.12 (m, 2H), 1.00-1.06 (m, 2H).

1-(1-cyclopropyl-5-((4-(ethylamino)-5-(trifluoromethyl)pyrimidin-2-yl)amino)-1H-pyrazol-3-yl)pyrrolidin-2-one To a solution of 1-(5-amino-1-cyclopropyl-pyrazol-3-yl)pyrrolidin-2-one (180 mg, 872.77 µmol) and 2-chloro-N-ethyl-5-(trifluoromethyl)pyrimidin-4-amine (197 mg, 872.77 µmol) in 1,4-dioxane (10 mL) was added p-TsOH.H$_2$O (45 mg, 261.83 µmol). The mixture was stirred at 90° C. for 12 h. The reaction mixture was diluted with H$_2$O (30 mL) and adjusted to pH=8-9 with aq. NaHCO$_3$ (10 mL) at 0° C. and extracted with EtOAc (3×30 mL). The combined organic layers were washed with brine (10 mL), dried over Na$_2$SO$_4$, filtered and concentrated under reduced pressure. The residue was purified by prep-HPLC (FA) to give 1-(1-cyclopropyl-5-((4-(ethylamino)-5-(trifluoromethyl)pyrimidin-2-yl)amino)-1H-pyrazol-3-yl)pyrrolidin-2-one. $^1$H NMR (400 MHz, CDCl$_3$): δ ppm 8.16 (s, 1H), 7.35 (br s, 1H), 7.22 (s, 1H), 5.27 (br s, 1H), 3.93 (t, J=7.06 Hz, 2H), 3.62-3.73 (m, 2H), 3.19-3.27 (m, 1H), 2.56 (t, J=8.16 Hz, 2H), 2.09-2.20 (m, 2H), 1.34 (t, J=7.28 Hz, 3H), 1.15-1.20 (m, 2H), 1.09-1.15 (m, 2H). HPLC: RT 2.11 min. MS: m/z: 396.2 [M+H]$^+$.

Example 6

Synthesis of N2-[3-cyclopropyl-1-(1,1-dioxothietan-3-yl)pyrazol-4-yl]-N4-ethyl-5-(trifluoromethyl)pyrimidine-2,4-diamine (110)

3-(3-cyclopropyl-4-nitro-pyrazol-1-yl)thietane 1,1-dioxide

To a mixture of 3-cyclopropyl-4-nitro-1H-pyrazole (500 mg, 3.26 mmol) in DMF (15 mL) was added NaH (156 mg, 3.91 mmol, 60% purity) at 0° C. under N$_2$. The mixture was stirred at 20° C. for 30 min, then treated with 3-bromothietane 1,1-dioxane (1.01 g, 3.26 mmol) and stirred at 20° C. for 15.5 h. The mixture was poured into ice-water (30 mL) and extracted with EtOAc (3×15 mL). The combined organic phase was washed with brine (3×15 mL), dried over anhydrous Na$_2$SO$_4$, filtered and concentrated under reduced pressure. The residue was purified by silica gel column chromatography (PE:EtOAc=1:0 to 3:1), to give 3-(3-cyclopropyl-4-nitro-pyrazol-1-yl)thietane 1,1-dioxide as a yellow oil.

3-cyclopropyl-1-(1,1-dioxothietan-3-yl)pyrazol-4-amine

To a solution of 3-(3-cyclopropyl-4-nitro-pyrazol-1-yl)thietane 1,1-dioxide (160 mg, 621.91 µmol) in EtOH (8 mL) and H$_2$O (2 mL) was added Fe (174 mg, 3.11 mmol) and NH$_4$Cl (166 mg, 3.11 mmol, 108.71 µL) at 20° C. The reaction mixture was heated at 70° C. for 2 h, then concentrated under reduced pressure. The residue was washed with a mixture solvent of DCM and MeOH (10 mL, 10:1), filtered and the filtrate was concentrated under reduced pressure to give 3-cyclopropyl-1-(1,1-dioxothietan-3-yl)pyrazol-4-amine as a brown oil.

N2-[3-cyclopropyl-1-(1,1-dioxothietan-3-yl)pyrazol-4-yl]-N4-ethyl-5-(trifluoromethyl)pyrimidine-2,4-diamine To a solution of 3-cyclopropyl-1-(1,1-dioxothietan-3-yl)pyrazol-4-amine (100 mg, 439.99 µmol) and 2-chloro-N-ethyl-5-(trifluoromethyl)pyrimidin-4-amine (99 mg, 439.99 µmol) in 1,4-dioxane (5 mL) was added p-TsOH (15 mg, 88 µmol). The reaction solution was stirred at 80° C. for 1 h. The mixture was adjusted to pH=7 with sat.NaHCO$_3$, extracted with EtOAc (3×5 mL). The combined organic layers were washed with brine (5 mL), dried over anhydrous Na$_2$SO$_4$, filtered and concentrated under reduced pressure. The crude product was purified by prep-HPLC (neutral) to give N2-[3-cyclopropyl-1-(1,1-dioxothietan-3-yl)pyrazol-4-yl]-N4-ethyl-5-(trifluoromethyl)pyrimidine-2,4-diamine $^1$H NMR (400 MHz, CDCl$_3$): δ 8.16 (s, 1H), 8.12 (br s, 1H), 6.62-7.03 (m, 1H), 5.15 (br s, 1H), 5.07 (br s, 1H), 4.66 (br s, 2H), 4.58 (br s, 2H), 3.58 (br d, J=5.90 Hz, 2H), 1.67-1.78 (m, 1H), 1.32 (br t, J=6.78 Hz, 3H), 0.91-0.98 (m, 2H), 0.81-0.90 (m, 2H). HPLC: RT: 1.92 min. MS: m/z=417.2 [M+H]$^+$.

Example 7

Synthesis of (1R,5S)-1-[1-cyclopropyl-5-[[4-(ethylamino)-5-(trifluoromethyl)pyrimidin-2-yl]amino]pyrazol-3-yl]-3-oxabicyclo[3.1.0]hexan-2-one (162)

Methyl (1R,5S)-2-oxo-3-oxabicyclo[3.1.0]hexane-1-carboxylate

Na (8.27 g, 359.52 mmol) was added into MeOH (500 mL) and the mixture was stirred at 20° C. for 3 h until the Na dissolved. Dimethyl propanedioate (50 g, 378.44 mmol) was added at 0° C., after 30 min, (2S)-2-(chloromethyl)oxirane (31.51 g, 340.6 mmol) was added at 20° C. under N$_2$. The mixture was stirred at 90° C. for 12 h. The mixture was concentrated under reduced pressure at 45° C. The residue was poured into ice-water (100 mL) and stirred for 5 min. The aqueous phase was extracted with EtOAc (3×300 mL). The combined organic phase was washed with brine, dried over anhydrous Na$_2$SO$_4$, filtered and concentrated under reduced pressure. The residue was purified by silica gel column chromatography (PE:EtOAc=100:1 to 5:1) to give methyl (1R,5S)-2-oxo-3-oxabicyclo[3.1.0]hexane-1-carboxylate as an oil. $^1$H NMR (400 MHz, CDCl$_3$): δ ppm 4.35 (dd, J=9.37, 4.74 Hz, 1H), 4.18 (d, J=9.48 Hz, 1H), 3.79 (s, 3H), 3.33-3.40 (m, 1H), 2.74 (dt, J=7.94, 5.18 Hz, 1H), 2.07 (dd, J=7.94, 4.85 Hz, 1H), 1.39 (t, J=5.07 Hz, 1H).

3-oxo-3-[(1R,5S)-2-oxo-3-oxabicyclo[3.1.0]hexan-1-yl]propanenitrile

To a mixture of MeCN (1.45 g, 35.22 mmol) in THF (20 mL) was added n-BuLi (2.5 M, 14.09 mL) at −78° C. under N$_2$. After 1 h the mixture was added into the solution of methyl (1R,5S)-2-oxo-3-oxabicyclo[3.1.0]hexane-1-carboxylate (5 g, 32.02 mmol) in THF (30 mL) at −78° C., then the mixture was stirred at −78° C. for 2 h. The mixture was poured into aq. NH$_4$Cl (30 mL) and stirred for 5 min and adjusted the pH=3 with diluted HCl (1N). The aqueous phase was extracted with EtOAc (3×30 mL). The combined organic phase was washed with brine (30 mL), dried over anhydrous Na$_2$SO$_4$, filtered and concentrated under reduced pressure. The residue was purified by silica gel column chromatography (PE:MTBE=50:1 to 0:1) to give 3-oxo-3-[(1R, 5S)-2-oxo-3-oxabicyclo[3.1.0]hexan-1-yl]propanenitrile as a white solid. $^1$H NMR (400 MHz, CDCl$_3$): δ ppm 4.25-4.47 (m, 3H), 4.03-4.15 (m, 1H), 3.02 (dt, J=7.99, 5.26 Hz, 1H), 2.19 (dd, J=8.16, 4.41 Hz, 1H), 1.58-1.65 (m, 1H).

(1R, 5S)-1-(5-amino-1-cyclopropyl-pyrazol-3-yl)-3-oxabicyclo[3.1.0]hexan-2-one

To a mixture of 3-oxo-3-[(1R,5S)-2-oxo-3-oxabicyclo[3.1.0]hexan-1-yl]propanenitrile (800 mg, 4.84 mmol) in i-PrOH (20 mL) was added cyclopropylhydrazine dihydrochloride salt (632.28 mg, 4.36 mmol) in one portion at 25° C. under N$_2$. The mixture was stirred at 50° C. for 12 h. The mixture was poured into aq. NaHCO$_3$ (50 mL) and stirred for 10 min. The aqueous phase was extracted with DCM/MeOH (3:1, 3×20 mL). The combined organic phase was washed with brine (20 mL), dried with anhydrous $Na_2SO_4$, filtered and concentrated under reduced pressure. The residue was purified by prep-TLC ($SiO_2$, DCM:MeOH=20:1) to give (1R,5S)-1-(5-amino-1-cyclopropyl-pyrazol-3-yl)-3-oxabicyclo[3.1.0]hexan-2-one as a brown oil. LCMS: RT 0.370 min, m/z=220.2 $[M+H]^+$. $^1H$ NMR (400 MHz, $CDCl_3$): δ ppm 5.76 (s, 1H), 4.38 (dd, J=9.15, 4.74 Hz, 1H), 4.20 (d, J=9.26 Hz, 1H), 3.83 (br s, 2H), 3.06 (tt, J=6.89, 3.58 Hz, 1H), 2.61 (dt, J=7.72, 4.63 Hz, 1H), 1.81 (dd, J=7.72, 4.41 Hz, 1H), 1.24 (t, J=4.74 Hz, 1H), 0.94-1.11 (m, 4H).

(1R,5S)-1-[1-cyclopropyl-5-[[4-(ethylamino)-5-(trifluoromethyl)pyrimidin-2-yl]amino]pyrazol-3-yl]-3-oxabicyclo[3.1.0]hexan-2-one To a mixture of (1R,5S)-1-(5-amino-1-cyclopropyl-pyrazol-3-yl)-3-oxabicyclo[3.1.0]hexan-2-one (150 mg, 684.18 μmol) and 2-chloro-N-ethyl-5-(trifluoromethyl)pyrimidin-4-amine (154.35 mg, 684.18 μmol) in 1,4-dioxane (5 mL) was added p-TsOH.$H_2O$ (26.03 mg, 136.84 μmol) in one portion at 20° C. under $N_2$. The mixture was stirred at 90° C. for 12 h. The mixture was poured into aq. $NaHCO_3$ (30 mL) and stirred for 10 min. The aqueous phase was extracted with EtOAc (3×20 mL). The combined organic phase was washed with brine (30 mL), dried with anhydrous $Na_2SO_4$, filtered and concentrated under reduced pressure. The residue was purified by prep-HPLC (neutral condition) to give (1R,5S)-1-[1-cyclopropyl-5-[[4-(ethylamino)-5-(trifluoromethyl)pyrimidin-2-yl]amino]pyrazol-3-yl]-3-oxabicyclo[3.1.0]hexan-2-one. $^1H$ NMR (400 MHz, $CDCl_3$): δ ppm 8.10 (s, 1H), 7.13 (br s, 1H), 6.87 (s, 1H), 5.16 (br s, 1H), 4.35 (dd, J=9.22, 4.71 Hz, 1H), 4.18 (d, J=9.29 Hz, 1H), 3.49-3.64 (m, 2H), 3.07-3.19 (m, 1H), 2.57-2.68 (m, 1H), 1.81 (dd, J=7.72, 4.45 Hz, 1H), 1.22-1.30 (m, 4H), 0.98-1.12 (m, 3H), 1.09 (br s, 1H). HPLC: reaction time: 2.17 min. MS: m/z: 409 $[M+H]^+$.

Example 8

Synthesis of (1R,3R)-3-(5-((4-(ethylamino)-5-(trifluoromethyl)pyrimidin-2-yl)amino)-1H-pyrazol-1-yl)cyclobutanecarbonitrile (181)

3-[2-(3-benzyloxycyclobutylidene)hydrazino]propanenitrile

A mixture of 3-benzyloxycyclobutanone (10 g, 56.75 mmol) and 3-hydrazinopropanenitrile (4.83 g, 56.75 mmol) in EtOH (150 mL) was stirred at 20° C. for 16 h. The mixture was concentrated under reduced pressure to afford 3-[2-(3-benzyloxycyclobutylidene)hydrazino]propanenitrile (13.81 g, crude) as a yellow oil. LCMS: RT 0.686 min, m/z=244.2 $[M+H]^+$.

2-(3-benzyloxycyclobutyl)pyrazol-3-amine

To a mixture of 3-[2-(3-benzyloxycyclobutylidene)hydrazino]propanenitrile (13.81 g, 56.76 mmol) in t-BuOH (130 mL) was added t-BuONa (5.45 g, 56.76 mmol) under $N_2$. The mixture was stirred at 110° C. for 3 h. The mixture was poured into ice-water (100 mL) and extracted with EtOAc (2×100 mL). The organic phase was adjusted to pH=3 by 2N HCl and washed with water (3×100 mL). The aqueous phase was adjusted to pH=8 by 6 N NaOH, extracted with EtOAc (3×100 mL), washed with brine (100 mL), dried over anhydrous $Na_2SO_4$, filtered and concentrated to afford 2-(3-benzyloxycyclobutyl)pyrazol-3-amine as a yellow oil. LCMS: RT 0.625 min, m/z=244.2 $[M+H]^+$.

3-(5-aminopyrazol-1-yl)cyclobutanol

To a solution of 2-(3-benzyloxycyclobutyl)pyrazol-3-amine (5 g, 20.55 mmol) in DCM (200 mL) was added $BCl_3$ (1 M, 8.02 mL) at 0° C. under $N_2$. The mixture was stirred at 20° C. for 2 h. The mixture was poured into saturated $NaHCO_3$ (200 mL) and the aqueous phase was concentrated under reduced pressure. The residue was washed with DCM:MeOH (v:v=10:1, 100 mL), filtered and the filtrate was concentrated under reduced pressure to afford 3-(5-aminopyrazol-1-yl)cyclobutanol as a yellow oil. LCMS: RT 0.096 min, m/z=154.1 $[M+H]^+$.

(1S,3S)-3-(5-((4-(ethylamino)-5-(trifluoromethyl)pyrimidin-2-yl)amino)-1H-pyrazol-1-yl)cyclobutanol and (1R,3R)-3-(5-((4-(ethylamino)-5-(trifluoromethyl)pyrimidin-2-yl)amino)-1H-pyrazol-1-yl)cyclobutanol To a mixture of 3-(5-aminopyrazol-1-yl)cyclobutanol (2.2 g, 14.36 mmol) in NMP (22 mL) was added 2-chloro-N-ethyl-5-(trifluoromethyl)pyrimidin-4-amine (2.59 g, 11.49 mmol) and p-TsOH.$H_2O$ (819.59 mg, 4.31 mmol) in one portion at 20° C. under $N_2$. The mixture was then heated to 100° C. and stirred for 16 h. The mixture was cooled to 20° C., poured into water (150 mL) and adjusted to pH=7-8 by aqueous $NaHCO_3$. The aqueous phase was extracted with EtOAc (3×50 mL). The combined organic phase was washed with brine (50 mL), dried over anhydrous $Na_2SO_4$, filtered and concentrated under reduced pressure to give a residue. The residue was purified by silica gel column chromatography (DCM:MeOH=30:1) to afford a mixture of (1S,3S)-3-(5-((4-(ethylamino)-5-(trifluoromethyl)pyrimidin-2-yl)amino)-1H-pyrazol-1-yl)cyclobutanol and (1R,3R)-3-(5-((4-(ethylamino)-5-(trifluoromethyl)pyrimidin-2-yl)amino)-1H-pyrazol-1-yl)cyclobutanol as a yellow gum.

(1S,3S)-3-(5-((4-(ethylamino)-5-(trifluoromethyl)pyrimidin-2-yl)amino)-1H-pyrazol-1-yl)cyclobutyl methanesulfonate (1R,3R)-3-(5-((4-(ethylamino)-5-(trifluoromethyl)pyrimidin-2-yl)amino)-1H-pyrazol-1-yl)cyclobutyl methanesulfonate To a mixture of (1S,3S)-3-(5-((4-(ethylamino)-5-(trifluoromethyl)pyrimidin-2-yl)amino)-1H-pyrazol-1-yl)cyclobutanol and (1R,3R)-3-(5-((4-(ethylamino)-5-(trifluoromethyl)pyrimidin-2-yl)amino)-1H-pyrazol-1-yl)cyclobutano (2 g, 5.84 mmol) in DCM (40 mL) was added TEA (709.14 mg, 7.01 mmol) and MsCl (802.77 mg, 7.01 mmol) at 0° C. under $N_2$. The mixture was then stirred at 0° C. for another 1 h. The mixture was added with water (10 mL) and stirred for 3 min. The organic phase was separated, washed with brine (10 mL), dried over anhydrous $Na_2SO_4$, filtered and concentrated under reduced pressure to give a residue. The residue was purified by silica gel column chromatography (DCM:MeOH=30:1) to afford a mixture of (1S,3S)-3-(5-((4-(ethylamino)-5-(trifluoromethyl)pyrimidin-2-yl)amino)-1H-pyrazol-1-ypcyclobutyl methanesulfonate and (1R,3R)-3-(5-((4-(ethylamino)-5-(trifluoromethyl)pyrimidin-2-yl)amino)-1H-pyrazol-1-ypcyclobutyl methanesulfonate as a yellow oil.

(1R,3R)-3-(5-((4-(ethylamino)-5-(trifluoromethyl)pyrimidin-2-yl)amino)-1H-pyrazol-1-yl)cyclobutanecarbonitrile To a mixture of (1S,3S)-3-(5-((4-(ethylamino)-5-(trifluoromethyl)pyrimidin-2-yl)amino)-1H-pyrazol-1-ypcyclobutylmethanesulfonate and (1R,3R)-3-(5-((4-(ethylamino)-5-(trifluoromethyl)pyrimidin-2-yl)amino)-1H-pyrazol-1-yl)cyclobutyl methanesulfonate (200 mg, 475.73 μmol) in DMSO (4 mL) was added 18-crown-6 (12 mg, 47.57 μmol) and NaCN (140 mg, 2.85 mmol) at 20° C. under $N_2$. The mixture was then heated to 120° C. and stirred for 8 h. The mixture was cooled to 20° C. and poured into water (50 mL). The aqueous phase was extracted with EtOAc (3×20 mL). The combined organic phase was washed with brine (20 mL), dried over anhydrous $Na_2SO_4$, filtered and concentrated under reduced pressure to give a residue. The residue was purified by prep-HPLC (FA) to give product, which was further purified by prep-TLC (PE:EtOAc=1:1) to afford (1R,3R)-3-(5-((4-(ethylamino)-5-(trifluoromethyl)pyrimidin-2-yl)amino)-1H-pyrazol-1-yl)cyclobutanecarbonitrile and a byproduct 2-(6,7-dihydro-5,7-methanopyrazolo[1,5-a]pyrimidin-4(5H)-yl)-N-ethyl-5-(trifluoromethyl)pyrimidin-4-amine.

(1R,3R)-3-(5-((4-(ethylamino)-5-(trifluoromethyl)pyrimidin-2-yl)amino)-1H-pyrazol-1-yl)cyclobutanecarbonitrile $^1$H NMR (400 MHz, $CDCl_3$): δ 8.08 (s, 1H), 7.57 (d, J=1.76 Hz, 1H), 7.08 (br s, 1H), 6.19 (d, J=1.76 Hz, 1H), 5.16 (br s, 1H), 5.06 (quin, J=7.87 Hz, 1H), 3.36-3.48 (m, 2H), 3.24-3.36 (m, 1H), 3.06-3.18 (m, 2H), 2.73-2.84 (m, 2H), 1.20 (t, J=7.22 Hz, 3H). LCMS: RT: 0.652 min. MS: m/z: 352.1 [M+H]$^+$.

Example 9

Synthesis of N2-(1-((1r,3r)-3-(2H-1,2,3-triazol-2-yl)cyclobutyl)-1H-pyrazol-5-yl)-N4-ethyl-5-(trifluoromethyl)pyrimidine-2,4-diamine (182) and $N_2$-(1-((1r,3r)-3-(1H-1,2,3-triazol-1-yl)cyclobutyl)-1H-pyrazol-5-yl)-N4-ethyl-5-(trifluoromethyl)pyrimidine-2,4-diamine (183)

$N_2$-(1-((1R,3R)-3-(2H-1,2,3-triazol-2-yl)cyclobutyl)-1H-pyrazol-5-yl)-N4-ethyl-5-(trifluoromethyl)pyrimidine-2,4-diamine and $N_2$-(1-((1R,3R)-3-(1H-1,2,3-triazol-1-yl)cyclobutyl)-1H-pyrazol-5-yl)-N4-ethyl-5-(trifluoromethyl)pyrimidine-2,4-diamine To a mixture of (1S,3S)-3-(5-((4-(ethylamino)-5-(trifluoromethyl)pyrimidin-2-yl)amino)-1H-pyrazol-1-yl)cyclobutyl methanesulfonate and (1R,3R)-3-(5-((4-(ethylamino)-5-(trifluoromethyl)pyrimidin-2-yl)amino)-1H-pyrazol-1-ypcyclobutyl methanesulfonate (300 mg, 713.59 μmol) in DMF (5 mL) was added $K_2CO_3$ (148 mg, 1.07 mmol) and 2H-triazole (74 mg, 1.07 mmol) in one portion at 20° C. under $N_2$. The mixture was then heated to 120° C. and stirred for 8 h. The mixture was cooled to 20° C. and poured into water (50 mL). The aqueous phase was extracted with EtOAc (3×20 mL). The combined organic phase was washed with brine (20 mL), dried over anhydrous $Na_2SO_4$, filtered and concentrated under reduced pressure. The residue was separated by prep-HPLC (FA condition) to afford $N_2$-(1-((1R,3R)-3-(2H-1,2,3-triazol-2-yl)cyclobutyl)-1H-pyrazol-5-yl)-N4-ethyl-5-(trifluoromethyl)pyrimidine-2,4-diamine and $N_2$-(1-((1R,3R)-3-(1H-1,2,3-triazol-1-yl)cyclobutyl)-1H-pyrazol-5-yl)-N4-ethyl-5-(trifluoromethyl)pyrimidine-2,4-diamine.

$N_2$-(1-((1R,3R)-3-(2H-1,2,3-triazol-2-yl)cyclobutyl)-1H-pyrazol-5-yl)-N4-ethyl-5-(trifluoromethyl)pyrimidine-2,4-diamine (182)

$^1$H NMR (400 MHz, $CDCl_3$): δ 8.11 (s, 1H), 7.64 (s, 2H), 7.61 (d, J=1.88 Hz, 1H), 6.83 (br s, 1H), 6.29 (d, J=1.76 Hz, 1H), 5.50 (tt, J=4.49, 8.69 Hz, 1H), 5.17-5.27 (m, 1H), 5.13 (br s, 1H), 3.39-3.51 (m, 2H), 3.25-3.36 (m, 2H), 3.01-3.14 (m, 2H), 1.21 (t, J=7.22 Hz, 3H). LCMS: RT: 0.706 min. MS: m/z: 394.3 [M+H]$^+$.

$N_2$-(1-((1R,3R)-3-(1H-1,2,3-triazol-1-yl)cyclobutyl)-1H-pyrazol-5-yl)-N4-ethyl-5-(trifluoromethyl)pyrimidine-2,4-diamine (183)

$^1$H NMR (400 MHz, $CDCl_3$): δ 8.10 (s, 1H), 7.74 (s, 1H), 7.61 (d, J=1.63 Hz, 1H), 7.60 (s, 1H), 6.70 (br s, 1H), 6.28 (d, J=1.76 Hz, 1H), 5.36-5.45 (m, 1H), 5.18-5.27 (m, 1H), 5.14 (br s, 1H), 3.37-3.53 (m, 2H), 3.31 (ddd, J=5.77, 8.31, 13.65 Hz, 2H), 3.11-3.23 (m, 2H), 1.22 (t, J=7.22 Hz, 3H). LCMS: RT: 0.660 min. MS: m/z: 394.2 [M+H]$^+$.

Example 10

Synthesis of N2-(5-cyclopropyl-1-pyrazin-2-yl-pyrazol-4-yl)-N4-ethyl-5-(trifluoromethyl)pyrimidine-2,4-diamine (105)

2-(4-nitropyrazol-1-yl)pyrazine

To a solution of 4-nitro-1H-pyrazole (1 g, 8.84 mmol) in DMF (20 mL) was added NaH (424 mg, 10.61 mmol, 60% purity) at 0° C. under $N_2$. The mixture was stirred at 0° C. for 1 h. Then 2-chloropyrazine (1.01 g, 8.84 mmol, 790.99 μL) was added at 0° C. and the mixture was heated to 80° C. and stirred for 12 h. The mixture was cooled to 20° C., quenched by cold aqueous sat. $NH_4Cl$ solution (60 mL). The aqueous phase was extracted with EtOAc (3×20 mL). The combined organic phase was washed with brine (3×15 mL), dried over anhydrous $Na_2SO_4$, filtered and concentrated under reduced pressure. The residue was purified by silica gel column chromatography (PE:EtOAc=10:1 to 0:1) to give 2-(4-nitropyrazol-1-yl)pyrazine as a light-yellow solid. 1H NMR (400 MHz, DMSO-d6): δ ppm 9.54 (s, 1H), 9.31 (d, J=1.13 Hz, 1H), 8.81 (d, J=2.51 Hz, 1H), 8.70-8.74 (m, 1H), 8.71 (s, 1H), 8.69 (dd, J=2.45, 1.32 Hz, 1H).

2-(5-chloro-4-nitro-pyrazol-1-yl)pyrazine

To a solution of 2-(4-nitropyrazol-1-yl)pyrazine (0.78 g, 4.08 mmol) in THF (15 mL) was added LiHMDS (1 M, 4.49 mmol, 4.49 mL) at −78° C. under $N_2$. The mixture was stirred at −78° C. for 30 min, then a solution of 1,1,1,2,2,2-hexachloroethane (1.06 g, 4.49 mmol, 508.45 μL) in THF (10 mL) was added at −78° C. under $N_2$ and the mixture was stirred for 3.5 h. The mixture was quenched by cold aqueous sat. $NH_4Cl$ (30 mL). The aqueous phase was extracted with EtOAc (3×10 mL). The combined organic phase was washed with brine (10 mL), dried over anhydrous $Na_2SO_4$, filtered and concentrated. The residue was purified by silica gel column chromatography (PE:EtOAc=10:1 to 1:1) to give 2-(5-chloro-4-nitro-pyrazol-1-yl)pyrazine as a white solid. LCMS: RT 1.066 min. MS m/z=226.0 [M+H]$^+$.

2-(5-cyclopropyl-4-nitro-pyrazol-1-yl)pyrazine

To a mixture of 2-(5-chloro-4-nitro-pyrazol-1-yl)pyrazine (200 mg, 886.56 μmol) and cyclopropylboronic acid (380 mg, 4.43 mmol) in 1,4-dioxane (10 mL) was added KF (154 mg, 2.66 mmol) and Pd(dppf)Cl$_2$.CH$_2$Cl$_2$ (145 mg, 177.31 μmol) at 20° C. under N$_2$. The mixture was heated to 110° C. and stirred for 12 h. The mixture was cooled to 20° C. and filtered. The residue was added with water (15 mL). The aqueous phase was extracted with EtOAc (3×8 mL). The combined organic phase was washed with brine (8 mL), dried over anhydrous Na$_2$SO$_4$, filtered and concentrated. The residue was purified by silica gel column chromatography (PE:EtOAc=10:1 to 0:1) to give 2-(5-cyclopropyl-4-nitro-pyrazol-1-yl)pyrazine. 1H NMR (400 MHz, CDCl$_3$): δ ppm 9.08 (s, 1H), 8.71 (d, J=2.38 Hz, 1H), 8.56-8.61 (m, 1H), 8.29 (s, 1H), 2.36 (tt, J=8.52, 5.79 Hz, 1H), 1.07-1.17 (m, 2H), −0.17 (tt, J=8.96, 5.91 Hz, 2H).

5-cyclopropyl-1-pyrazin-2-yl-pyrazol-4-amine

To a solution of 2-(5-cyclopropyl-4-nitro-pyrazol-1-yl)pyrazine (240 mg, 1.04 mmol) in EtOH (16 mL) and H$_2$O (4 mL) was added NH$_4$Cl (277 mg, 5.19 mmol) and Fe (290 mg, 5.19 mmol) at 20° C. The mixture was heated to 80° C. and stirred for 2 h. The mixture was cooled to 20° C., filtered and concentrated under reduced pressure. The residue was washed with DCM:MeOH (10 mL, v:v=10:1), filtered and concentrated under reduced pressure to give 5-cyclopropyl-1-pyrazin-2-yl-pyrazol-4-amine as a brown oil. LCMS: RT 0.711 min. MS m/z=202.1 [M+H]$^+$.

N2-(5-cyclopropyl-1-pyrazin-2-yl-pyrazol-4-yl)-N4-ethyl-5-(trifluoromethyl)pyrimidine-2,4-diamine To a mixture of 5-cyclopropyl-1-pyrazin-2-yl-pyrazol-4-amine (100 mg, 496.95 μmol) and 2-chloro-N-ethyl-5-(trifluoromethyl)pyrimidin-4-amine (112 mg, 496.95 μmol) in 1,4-dioxane (5 mL) was added p-TsOH.H$_2$O (34 mg, 198.78 μmol) at 20° C. The mixture was heated to 90° C. and stirred for 2 h. The mixture was cooled to 20° C., added with water (10 mL) and adjusted to pH=7-8 by sat. NaHCO$_3$. The aqueous phase was extracted with EtOAc (3×8 mL). The combined organic phase was washed with brine (2×5 mL), dried over anhydrous Na$_2$SO$_4$, filtered and concentrated. The residue was purified by silica gel column chromatography (PE:EtOAc=10:1 to 0:1) to give N$_2$-(5-cyclopropyl-1-pyrazin-2-yl-pyrazol-4-yl)-N4-ethyl-5-(trifluoromethyl)pyrimidine-2,4-diamine $^1$H NMR (400 MHz, MeOD): δ ppm 9.08 (s, 1H), 8.55 (s, 2H), 8.04 (br s, 2H), 3.53 (q, J=6.82 Hz, 2H), 2.16-2.34 (m, 1H), 1.20 (br t, J=7.03 Hz, 3H), 0.91 (br d, J=6.90 Hz, 2H), 0.55 (br d, J=4.77 Hz, 2H). HPLC: RT: 2.06 min. MS: m/z: 391.2 [M+H]$^+$.

Example 11

Synthesis of (3S)-3-[3-cyclopropyl-4-[[4-(methylamino)-5-(trifluoromethyl)pyrimidin-2-yl]amino]pyrazol-1-yl]-3-methyl-tetrahydrofuran-2-one and (3R)-3-[3-cyclopropyl-4-[[4-(methylamino)-5-(trifluoromethyl)pyrimidin-2-yl]-amino]pyrazol-1-yl]-3-methyl-tetrahydrofuran-2-one (113 and 122)

3-(3-cyclopropyl-4-nitro-pyrazol-1-yl)tetrahydrofuran-2-one

To a solution of 3-cyclopropyl-4-nitro-1H-pyrazole (1 g, 6.53 mmol) in DMF (10 mL) was added NaH (313 mg, 7.84 mmol, 60% purity) at 0° C. under N$_2$. The mixture was stirred at 20° C. for 30 min, then treated with 3-bromotetrahydrofuran-2-one (1.19 g, 7.18 mmol, 670 μL) and stirred for 15.5 h. The mixture was poured into ice-water (20 mL) and extracted with EtOAc (3×10 mL). The combined organic phase was washed with brine (3×10 mL), dried over anhydrous Na$_2$SO$_4$, filtered and concentrated under reduced pressure. The residue was purified by silica gel column chromatography (PE:EtOAc=1:0 to 1:1) to give 3-(3-cyclopropyl-4-nitro-pyrazol-1-yl)tetrahydrofuran-2-one as a yellow oil. $^1$H NMR (400 MHz, CDCl$_3$): δ 8.31 (s, 1H), 4.96 (t, J=9.16 Hz, 1H), 4.65 (td, J=8.88, 3.45 Hz, 1H), 4.39-4.51 (m, 1H), 2.95 (dq, J=13.25, 8.92 Hz, 1H), 2.77-2.87 (m, 1H), 2.56-2.65 (m, 1H), 1.01-1.09 (m, 2H), 0.93-1.01 (m, 2H). LCMS: RT 0.746 min, m/z=252.1 [M+H]$^+$.

3-(3-cyclopropyl-4-nitro-pyrazol-1-yl)-3-methyl-tetrahydrofuran-2-one

To a solution of 3-(3-cyclopropyl-4-nitro-pyrazol-1-yl)tetrahydrofuran-2-one (780 mg, 3.29 mmol) in THF (15 mL) was added LDA (4.93 mmol, 2 M, 2.47 mL) at −78° C. under N$_2$. The mixture was stirred at −78° C. for 30 min, then treated with MeI (700 mg, 4.93 mmol, 307 μL) at −78° C. and warmed to 0° C. and stirred for 1.5 h. The mixture was poured into sat. NH$_4$Cl (15 mL) and extracted with EtOAc (3×5 mL). The combined organic phase was washed with brine (5 mL), dried over anhydrous Na$_2$SO$_4$, filtered and concentrated under reduced pressure. The residue was purified by silica gel column chromatography (PE:EtOAc=1:0 to 1:1) to give 3-(3-cyclopropyl-4-nitro-pyrazol-1-yl)-3-methyl-tetrahydrofuran-2-one as a colorless oil. $^1$H NMR (400 MHz, CDCl$_3$): δ 8.40 (s, 1H), 7.27 (s, 1H), 4.55 (td, J=8.53, 5.77 Hz, 1H), 4.38-4.48 (m, 1H), 3.12-3.22 (m, 1H), 2.56-2.65 (m, 1H), 2.49 (ddd, J=13.49, 7.59, 5.90 Hz, 1H), 1.84 (s, 3H), 1.00-1.09 (m, 2H), 0.90-1.00 (m, 3H). LCMS: RT 0.746 min, m/z=252.1 [M+H]$^+$.

3-(4-amino-3-cyclopropyl-pyrazol-1-yl)-3-methyl-tetrahydrofuran-2-one

To a solution of 3-(3-cyclopropyl-4-nitro-pyrazol-1-yl)-3-methyl-tetrahydrofuran-2-one (555 mg, 2.21 mmol) in MeOH (15 mL) was added Pd—C (10%, 220 mg) under N$_2$. The suspension was degassed under reduced pressure and purged with H$_2$ for three times. The mixture was stirred under H$_2$ (15 psi) at 20° C. for 2 h. The mixture was filtered and the filtrate was concentrated under reduced pressure to give 3-(4-amino-3-cyclopropyl-pyrazol-1-yl)-3-methyl-tetrahydrofuran-2-one as a yellow oil. NMR (400 MHz, CDCl$_3$): δ 7.18 (s, 1H), 4.43-4.51 (m, 1H), 4.30-4.39 (m, 1H), 3.25 (ddd, J=13.05, 7.53, 5.02 Hz, 1H), 2.91 (br s, 2H), 2.36 (dt, J=13.43, 7.47 Hz, 1H), 1.72 (s, 3H), 1.62-1.70 (m, 1H), 0.82-0.90 (m, 2H), 0.79 (ddd, J=7.81, 4.99, 2.38 Hz, 2H).

(3S)-3-[3-cyclopropyl-4-[[4-(methylamino)-5-(trifluoromethyl)pyrimidin-2-yl]amino]pyrazol-1-yl]-3-methyl-tetrahydrofuran-2-one and (3R)-3-[3-cyclopropyl-4-[[4-(methylamino)-5-(trifluoromethyl)pyrimidin-2-yl]amino]pyrazol-1-yl]-3-methyl-tetrahydrofuran-2-one A mixture of 2-chloro-N-methyl-5-(trifluoromethyl)pyrimidin-4-amine (143 mg, 677.95 μmol) and 3-(4-amino-3-cyclopropyl-pyrazol-1-yl)-3-methyl-tetrahydrofuran-2-one (150 mg, 677.95 μmol) in 1,4-dioxane (10 mL) was added p-TsOH.H$_2$O (40 mg, 203.39 µmol) at 20° C. under N$_2$ and stirred at 90° C. for 4 h. The mixture was poured into ice-water (10 mL) and extracted with EtOAc (3×8 mL). The combined organic phase was washed with brine (8 mL), dried over anhydrous Na$_2$SO$_4$, filtered and concentrated under reduced pressure. The residue was purified by prep-TLC (SiO$_2$, PE:EtOAc=1:1) to give 3-[3-cyclopropyl-4-[[4-(methylamino)-5-(trifluoromethyl)pyrimidin-2-yl]amino] pyrazol-1-yl]-3-methyl-tetrahydrofuran-2-one. The enantiomers were separated by SFC to provide (3S)-3-[3-cyclopropyl-4-[[4-(methylamino)-5-(trifluoromethyl)pyrimidin-2-yl]amino]pyrazol-1-yl]-3-methyl-tetrahydrofuran-2-one and (3R)-3-[3-cyclopropyl-4-[[4-(methylamino)-5-(trifluoromethyl)pyrimidin-2-yl]amino] pyrazol-1-yl]-3-methyl-tetrahydrofuran-2-one.

First Eluting Isomer—
$^1$H NMR (400 MHz, CDCl$_3$): δ 8.28 (br s, 1H), 8.13 (br s, 1H), 7.08 (br s, 1H), 5.25 (br s, 1H), 4.47 (br d, J=7.53 Hz, 1H), 4.38 (td, J=8.38, 4.83 Hz, 1H), 3.31 (br s, 1H), 3.11 (br s, 3H), 2.43 (dt, J=13.52, 7.48 Hz, 1H), 1.78 (s, 3H), 1.67-1.75 (m, 1H), 0.77-0.95 (m, 4H). HPLC: RT: 2.00 min. MS: m/z=397.2 [M+H]$^+$.

Second Eluting Isomer—
NMR (400 MHz, CDCl$_3$): δ 8.28 (br s, 1H), 8.13 (br s, 1H), 7.08 (br s, 1H), 5.25 (br s, 1H), 4.47 (br d, J=7.40 Hz, 1H), 4.33-4.42 (m, 1H), 3.32 (br s, 1H), 3.11 (br s, 3H), 2.37-2.49 (m, 1H), 1.78 (s, 3H), 1.67-1.76 (m, 1H), 0.79-0.94 (m, 4H). HPLC: RT: 2.00 min. MS: m/z=397.2 [M+H]$^+$.

Example 12

Synthesis of 2-[4-[[4-(ethylamino)-5-(trifluoromethyl)pyrimidin-2-yl]amino]-3-methyl-pyrazol-1-yl]-2-methyl-cyclopentanone (194)

2-(4-bromo-3-methyl-pyrazol-1-yl)cyclopentanone and 2-(4-bromo-5-methyl-pyrazol-1-yl)cyclopentanone To a solution of 4-bromo-3-methyl-1H-pyrazole (10 g, 62.11 mmol) in DMF (60 mL) was added NaH (3.23 g, 80.75 mmol, 60% purity) at 0° C. and stirred at 15° C. for 1 h. Then 2-chlorocyclopentanone (8.84 g, 74.53 mmol, 7.43 mL) was added to the mixture and stirred at 15° C. for 15 h. The reaction mixture was quenched by addition aq. NH$_4$Cl (300 mL) at 0° C., and then extracted with EtOAc (3×100 mL). The combined organic layers were washed with brine (200 mL), dried over Na$_2$SO$_4$, filtered and concentrated under reduced pressure. The residue was purified by silica gel column chromatography (PE:MTBE=2:1 to 1:1) to give the mixture of 2-(4-bromo-3-methyl-pyrazol-1-yl)cyclopentanone and 2-(4-bromo-5-methyl-pyrazol-1-yl)cyclopentanone as a yellow gum. LCMS: RT 2.119 min, m/z=243.1 [M+H]$^+$.

2-(4-bromo-3-methyl-pyrazol-1-yl)-2-methyl-cyclopentanone and 2-(4-bromo-5-methyl-pyrazol-1-yl)-2-methyl-cyclopentanone To a mixture of 2-(4-bromo-3-methyl-pyrazol-1-yl)cyclopentanone and 2-(4-bromo-5-methyl-pyrazol-1-yl)cyclopentanone (6.5 g, 26.74 mmol) in THF (30 mL) was added LiHMDS (1 M, 34.76 mL) and stirred at −78° C. for 1 h. MeI (4.93 g, 34.76 mmol, 2.16 mL) was then added at −78° C. and stirred at 15° C. for 15 h. The reaction mixture was quenched by addition of saturated aq. NH$_4$Cl (200 mL) at 0° C., and then extracted with EtOAc (3×70 mL). The combined organic layers were washed with brine (100 mL), dried over Na$_2$SO$_4$, filtered and concentrated under reduced pressure. The residue was purified by silica gel column chromatography (PE:EtOAc=4:1 to 2:1) to give the mixture of 2-(4-bromo-3-methyl-pyrazol-1-yl)-2-methyl-cyclopentanone) and 2-(4-bromo-5-methyl-pyrazol-1-yl)-2-methyl-cyclopentanone as a yellow gum. LCMS: RT 0.747 min, m/z=257.1 [M+H]$^+$.

tert-butyl N-[3-methyl-1-(1-methyl-2-oxo-cyclopentyl)pyrazol-4-yl]carbamate and tert-butyl N-[5-methyl-1-(1-methyl-2-oxo-cyclopentyl)pyrazol-4-yl] carbamate A mixture of 2-(4-bromo-3-methyl-pyrazol-1-yl)-2-methyl-cyclopentanone and 2-(4-bromo-5-methyl-pyrazol-1-yl)-2-methyl-cyclopentanone (160 mg, 622.26 µmol), NH$_2$Boc (437 mg, 3.73 mmol), t-BuONa (120 mg, 1.24 mmol) and [2-(2-aminoethyl)phenyl]-chloro-palladium;di-tert-butyl-[2-(2,4,6-triisopropylphenyl)phenyl]phosphane (107 mg, 155.57 µmol) in THF (2 mL) was degassed and purged with N$_2$ for 3 times, and then the mixture was stirred at 90° C. for 2 h under N$_2$. The reaction mixture was filtered and the filtrate was concentrated under reduced pressure. The residue was purified by prep-HPLC (neutral) to give tert-butyl N-[3-methyl-1-(1-methyl-2-oxo-cyclopentyl) pyrazol-4-yl]carbamate and tert-butyl N-[5-methyl-1-(1-methyl-2-oxo-cyclopentyl)pyrazol-4-yl]carbamate as a yellow gum. LCMS: RT 1.203 min, m/z=294.3 [M+H]$^+$.

2-(4-amino-3-methyl-pyrazol-1-yl)-2-methyl-cyclopentanone

A solution of tert-buty N-[3-methyl-1-(1-methyl-2-oxo-cyclopentyl)pyrazol-4-yl]carbamate (80 mg, 272.7 µmol) in HCl/EtOAc (3 mL) was stirred at 0° C. for 1 h. The reaction mixture was concentrated under reduced pressure to give 2-(4-amino-3-methyl-pyrazol-1-yl)-2-methyl-cyclopentanone as a yellow solid. LCMS: RT 1.032 min, m/z=194.2 [M+H]$^+$.

2-[4-[[4-(ethylamino)-5-(trifluoromethyl)pyrimidin-2-yl]amino]-3-methyl-pyrazol-1-yl]-2-methyl-cyclopentanone 2-(4-amino-3-methyl-pyrazol-1-yl)-2-methyl-cyclopentanone (55 mg, 284.61 µmol), 2-chloro-N-ethyl-5-(trifluoromethyl)pyrimidin-4-amine (64 mg, 284.61 µmol) and TEA (86 mg, 853.84 µmol, 118.84 µL) were taken up into a microwave tube in n-BuOH (1 mL). The sealed tube was heated at 110° C. for 1 h under microwave. The mixture was concentrated under reduced pressure. The residue was purified by prep-HPLC (neutral) and prep-TLC (PE:EtOAc=1:1) to give 2-[4-[[4-(ethylamino)-5-(trifluoromethyl)pyrimidin-2-yl]amino]-3-methyl-pyrazol-1-yl]-2-methyl-cyclopentanone. $^1$H NMR (400 MHz, CHLOROFORM-d): δ ppm 8.12 (br s, 2H), 6.66 (br s, 1H), 5.15 (br s, 1H), 3.58 (br s, 2H), 2.90-3.07 (m, 1H), 2.38-2.58 (m, 2H), 2.24 (s, 3H), 2.04-2.19 (m, 2H), 1.88-2.00 (m, 1H), 1.58 (s, 3H), 1.31 (br t, J=7.09 Hz, 3H). HPLC: Retention Time: 2.557 min. MS: (M+H$^+$) m/z: 383.2.

Example 13

Synthesis of (S)-3-(4-((4-(ethylamino)-5-(trifluoromethyl)pyrimidin-2-yl)amino)-3-methyl-1H-pyrazol-1-yl)-3-(fluoromethyl)dihydrofuran-2(3H)-one and (R)-3-(4-((4-(ethylamino)-5-(trifluoromethyl) pyrimidin-2-yl)amino)-3-methyl-1H-pyrazol-1-yl)-3-(fluoromethyl)dihydrofuran-2(3H)-one (216 and 217)

3-(hydroxymethyl)-3-(3-methyl-4-nitro-1H-pyrazol-1-yl)dihydrofuran-2(3H)-one

To a mixture of 3-(3-methyl-4-nitro-pyrazol-1-yl)tetrahydrofuran-2-one (2 g, 9.47 mmol) in THF (25 mL) was added LiHMDS (1 M, 12.31 mL) at −78° C. under $N_2$, and then the mixture was stirred at −78° C. for 0.5 h. A solution of paraformaldehyde (1.02 g, 11.37 mmol) in THF (1 mL) was then added to the reaction mixture and then the mixture was stirred at 10° C. for 2.5 h. The reaction was quenched by addition aq. sat. $NH_4Cl$ (150 mL) at 0° C., and then extracted with EtOAc (3×50 mL). The combined organic layers were washed with brine (50 mL), dried over $Na_2SO_4$, filtered and concentrated under reduced pressure. The residue was purified by silica gel column chromatography (PE:EtOAc=2:1 to 1:1) to give 3-(hydroxymethyl)-3-(3-methyl-4-nitro-pyrazol-1-yl)tetrahydrofuran-2-one as a white solid. LCMS: RT 0.497 min, m/z=242.1 [M+H]$^+$. $^1$H NMR (400 MHz, CHLOROFORM-d): δ 8.54 (s, 1H), 4.59-4.48 (m, 2H), 4.20-4.07 (m, 2H), 3.07-2.98 (m, 1H), 2.95-2.86 (m, 2H), 2.55 (s, 3H).

3-(fluoromethyl)-3-(3-methyl-4-nitro-1H-pyrazol-1-yl)dihydrofuran-2(3H)-one

To a solution of 3-(hydroxymethyl)-3-(3-methyl-4-nitro-pyrazol-1-yl)tetrahydrofuran-2-one (1.1 g, 4.56 mmol) in DCM (30 mL) was added DAST (5.88 g, 36.48 mmol, 4.82 mL) at 0° C., then the mixture was stirred at 20° C. for 15 h. The mixture was quenched by addition aq. sat. $NaHCO_3$ (200 mL) at 0° C., and extracted with EtOAc (3×70 mL). The combined organic layers were washed with brine (70 mL), dried over $Na_2SO_4$, filtered and concentrated under reduced pressure. The residue was purified by silica gel column chromatography (PE:EtOAc=3:1 to 1:1) to give 3-(fluoromethyl)-3-(3-methyl-4-nitro-pyrazol-1-yptetrahydrofuran-2-one as a white solid. LCMS: RT 0.576 min, m/z=244.1 [M+H]$^+$. $^1$H NMR (400 MHz, CHLOROFORM-d): δ 8.56 (s, 1H), 4.96-4.74 (m, 2H), 4.59-4.49 (m, 2H), 3.30-3.20 (m, 1H), 2.95-2.86 (m, 1H), 2.55 (s, 3H).

3-(4-amino-3-methyl-1H-pyrazol-1-yl)-3-(fluoromethyl)dihydrofuran-2(3H)-one

A mixture of 3-(fluoromethyl)-3-(3-methyl-4-nitro-pyrazol-1-yl)tetrahydrofuran-2-one (0.7 g, 2.88 mmol), Fe (804 mg, 14.39 mmol) and $NH_4Cl$ (770 mg, 14.39 mmol) in EtOH (8 mL) and $H_2O$ (2 mL) was stirred at 70° C. for 2 h. The reaction mixture was concentrated under reduced pressure, the residue was diluted with DCM:MeOH (50 mL, ratio=10:1), filtered and concentrated under reduced pressure to give 3-(4-amino-3-methyl-pyrazol-1-yl)-3-(fluoromethyptetrahydrofuran-2-one as a brown solid. LCMS: RT 0.087 min, m/z=214.1 [M+H]$^+$. $^1$H NMR (400 MHz, CHLOROFORM-d): δ 7.30 (s, 1H), 4.89-4.66 (m, 2H), 4.52-4.40 (m, 2H), 3.31 (br dd, J=6.2, 13.2 Hz, 1H), 2.87-2.80 (m, 1H), 2.21-2.15 (m, 3H).

(R)-3-(4-((4-(ethylamino)-5-(trifluoromethyl)pyrimidin-2-yl)amino)-3-methyl-1H-pyrazol-1-yl)-3-(fluoromethyl)dihydrofuran-2(3H)-one and (S)-3-(4-((4-(ethylamino)-5-(trifluoromethyl)pyrimidin-2-yl)amino)-3-methyl-1H-pyrazol-1-yl)-3-(fluoromethyl)dihydrofuran-2(3H)-one A mixture of 3-(4-amino-3-methyl-pyrazol-1-yl)-3-(fluoromethyl)tetrahydrofuran-2-one (0.2 g, 938.05 μmol), 2-chloro-N-ethyl-5-(trifluoromethyl)pyrimidin-4-amine (190 mg, 844.24 μmol) and p-TsOH.$H_2O$ (71 mg, 375.22 μmol) in 1,4-dioxane (3 mL) was stirred at 90° C. for 6 h under $N_2$. The reaction mixture was quenched by addition aq. sat. $NaHCO_3$ (60 mL) at 0° C., and then extracted with EtOAc (3×20 mL). The combined organic layers were washed with brine (20 mL), dried over $Na_2SO_4$, filtered and concentrated under reduced pressure. The residue was purified by silica gel column chromatography (PE:EtOAc=3:1 to 1:1) to give desired compound as a brown oil, which was separated by SFC.

SFC, First Eluting Isomer:
$^1$H NMR (400 MHz, CHLOROFORM-d): δ 8.30 (br s, 1H), 8.12 (s, 1H), 7.01-6.61 (m, 1H), 5.32-5.06 (m, 1H), 4.91-4.68 (m, 2H), 4.54-4.37 (m, 2H), 3.64-3.53 (m, 2H), 3.32 (br s, 1H), 2.92-2.79 (m, 1H), 2.26 (s, 3H), 1.33 (br t, J=7.0 Hz, 3H). HPLC: Retention Time: 2.02 min. MS: (M+H$^+$) m/z=403.3.

SFC, Second Eluting Isomer:
$^1$H NMR (400 MHz, CHLOROFORM-d): δ 8.30 (br s, 1H), 8.12 (s, 1H), 7.01-6.61 (m, 1H), 5.32-5.06 (m, 1H), 4.91-4.68 (m, 2H), 4.54-4.37 (m, 2H), 3.64-3.53 (m, 2H), 3.32 (br s, 1H), 2.92-2.79 (m, 1H), 2.26 (s, 3H), 1.33 (br t, J=7.0 Hz, 3H). HPLC: Retention Time: 1.99 min. MS: (M+W) m/z=403.3.

Example 14

Synthesis of N2-[5-chloro-1-[(3S)-1-ethyl-4,4-difluoro-3-piperidyl]pyrazol-4-yl]-N4-ethyl-5-(trifluoromethyl)pyrimidine-2,4-diamine and N2-[5-chloro-1-[(3R)-1-ethyl-4,4-difluoro-3-piperidyl]pyrazol-4-yl]-N4-ethyl-5-(trifluoromethyl)pyrimidine-2,4-diamine (204 and 205)

tert-butyl 3-(4-nitropyrazol-1-yl)-4-oxo-piperidine-1-carboxylate

To a solution of tert-butyl 3-bromo-4-oxo-piperidine-1-carboxylate (20 g, 71.91 mmol) and 4-nitro-1H-pyrazole (8.94 g, 79.10 mmol) in DMF (100 mL) was added $K_2CO_3$ (19.88 g, 143.81 mmol) at 20° C. under $N_2$. The mixture was stirred at 20° C. for 16 h. The mixture was poured into ice-water (300 mL) and extracted with EtOAc (3×100 mL). The combined organic phase was washed with brine (3×100 mL), dried over anhydrous $Na_2SO_4$, filtered and concentrated under reduced pressure. The residue was purified by silica gel column chromatography (PE:EtOAc=1:0 to 3:1) to give tert-butyl 3-(4-nitropyrazol-1-yl)-4-oxo-piperidine-1-carboxylate as a yellow oil. LCMS: RT 1.306 min, m/z=255.2 [M−56]$^+$. $^1$H NMR (400 MHz, CDCl$_3$): δ 8.22-8.27 (m, 1H), 8.12 (s, 1H), 4.97 (dd, J=10.85, 6.34 Hz, 1H), 4.75 (br s, 1H), 4.43 (br s, 1H), 3.64 (br t, J=11.86 Hz, 1H), 3.30 (br d, J=5.77 Hz, 1H), 1.41-1.58 (m, 9H), 1.41-1.58 (m, 2H).

tert-butyl 4,4-difluoro-3-(4-nitropyrazol-1-yl)piperidine-1-carboxylate

To a solution of tert-butyl3-(4-nitropyrazol-1-yl)-4-oxo-piperidine-1-carboxylate (1 g, 3.22 mmol) in DCM (10 mL) was added DAST (2.6 g, 16.11 mmol, 2.13 mL) at −78° C. under $N_2$. The mixture was stirred at 20° C. for 16 h. The mixture was poured into ice cold sat. $NaHCO_3$ (15 mL) and extracted with EtOAc (3×5 mL). The combined organic phase was washed with brine (5 mL), dried over anhydrous $Na_2SO_4$, filtered and concentrated under reduced pressure. The residue was purified by silica gel column chromatography (PE:EtOAc=1:0 to 3:1) to give tert-butyl 4,4-difluoro-3-(4-nitropyrazol-1-yl)piperidine-1-carboxylate as a white solid. LCMS: RT 1.335 min, m/z=277.1 [M−56]$^+$. $^1$H NMR (400 MHz, CDCl$_3$): δ 8.30 (s, 1H), 8.13 (s, 1H), 4.52 (ddq, J=14.23, 9.60, 4.65, 4.65, 4.65 Hz, 1H), 4.39 (br s, 1H), 4.10 (br s, 1H), 3.66 (br t, J=11.36 Hz, 1H), 3.30 (br t, J=11.42 Hz, 1H), 2.26-2.42 (m, 1H), 1.95-2.18 (m, 1H), 1.37-1.57 (m, 9H).

tert-butyl 3-(5-chloro-4-nitro-pyrazol-1-yl)-4,4-difluoro-piperidine-1-carboxylate To a solution of tert-butyl 4,4-difluoro-3-(4-nitropyrazol-1-yl)piperidine-1-carboxylate (740 mg, 2.23 mmol) in THF (10 mL) was added dropwise LiHMDS (1 M, 3.34 mmol, 3.34 mL) at −78° C. under $N_2$. The reaction was stirred at −78° C. for 1 h. Then 1,1,1,2,2,2-hexachloroethane (1.05 g, 4.45 mmol, 504.49 jut) in THF (5 mL) was added dropwise and the mixture was stirred at −78° C. for 1 h. The mixture was poured into sat. $NH_4Cl$ (15 mL) and extracted with EtOAc (3×5 mL). The combined organic phase was washed with brine (5 mL), dried over anhydrous $Na_2SO_4$, filtered and concentrated under reduced pressure. The residue was purified by silica gel column chromatography (PE:EtOAc=1:0 to 3:1) to give tert-butyl 3-(5-chloro-4-nitro-pyrazol-1-yl)-4,4-difluoro-piperidine-1-carboxylate as a yellow oil. LCMS: RT 1.352 min, m/z=311.2 [M−56]$^+$. $^1$H NMR (400 MHz, CDCl$_3$): δ 8.22 (s, 1H), 4.59-4.72 (m, 1H), 4.00-4.16 (m, 2H), 3.81-3.90 (m, 1H), 3.55 (br d, J=9.03 Hz, 1H), 2.38-2.54 (m, 1H), 1.96-2.15 (m, 1H), 1.39-1.56 (m, 9H).

3-(5-chloro-4-nitro-pyrazol-1-yl)-4,4-difluoro-piperidine

The mixture of tert-butyl 3-(5-chloro-4-nitro-pyrazol-1-yl)-4,4-difluoro-piperidine-1-carboxylate (1.8 g, 4.91 mmol) in HCl EtOAc (40 mL) was stirred at 20° C. for 2 h. The reaction mixture was concentrated under reduced pressure and the mixture was adjusted to pH=7-8 with sat. aq. $NaHCO_3$. Then the aqueous phase was extracted with EtOAc (3×15 mL), dried over anhydrous $Na_2SO_4$, filtered and concentrated under reduced pressure to give 3-(5-chloro-4-nitro-pyrazol-1-yl)-4,4-difluoro-piperidine as a light yellow solid. $^1$H NMR (400 MHz, CHLOROFORM-d): δ 8.17-8.32 (m, 1H), 4.57-4.81 (m, 1H), 3.59 (br dd, J=13.68, 4.89 Hz, 1H), 3.36 (br dd, J=13.93, 4.02 Hz, 1H), 3.14-3.27 (m, 1H), 2.98-3.11 (m, 1H), 2.37 (br s, 1H), 2.14-2.34 (m, 1H).

3-(5-chloro-4-nitro-pyrazol-1-yl)-1-ethyl-4,4-difluoro-piperidine

To a mixture of 3-(5-chloro-4-nitro-pyrazol-1-yl)-4,4-difluoro-piperidine (0.5 g) and acetaldehyde (2.07 g, 18.75 mmol, 2.63 mL) in MeOH (10 mL) was added $NaBH_3CN$ (589 mg, 9.38 mmol) and stirred for 15 min. Then $CH_3COOH$ (1.13 g, 18.75 mmol, 1.07 mL) was added to the solution at 20° C. and the mixture was stirred at 20° C. for 1 h. The mixture was adjusted to pH=7-8 with sat. aq. $NaHCO_3$ and the aqueous phase was extracted with EtOAc (3×15 mL). The combined organic phase was washed with brine (10 mL), dried over anhydrous $Na_2SO_4$, filtered and concentrated under reduced pressure. The residue was purified by silica gel column chromatography (PE:EtOAc=100:1 to 0:1) to give 3-(5-chloro-4-nitro-pyrazol-1-yl)-1-ethyl-4,4-difluoro-piperidine as a yellow oil. LCMS: RT 0.939 min, m/z=295.1 [M+H]$^+$. NMR (400 MHz, CHLOROFORM-d) δ: 8.19-8.33 (m, 1H), 4.78-4.95 (m, 1H), 3.10-3.22 (m, 2H), 2.97-3.06 (m, 1H), 2.57-2.67 (m, 2H), 2.39-2.51 (m, 1H), 2.22-2.36 (m, 1H), 2.12-2.21 (m, 1H), 1.13 (t, J=7.22 Hz, 3H).

5-chloro-1-(1-ethyl-4,4-difluoro-3-piperidyl)pyrazol-4-amine

To a mixture of 3-(5-chloro-4-nitro-pyrazol-1-yl)-1-ethyl-4,4-difluoro-piperidine (0.15 g, 509.02 µmol) in EtOH (4 mL) and $H_2O$ (1 mL) was added Fe (142 mg, 2.55 mmol) and $NH_4Cl$ (136 mg, 2.55 mmol, 88.98 µL) at 20° C. Then the mixture was stirred at 80° C. for 1 h. The reaction mixture was filtered and the filtrate was concentrated under reduced pressure. The crude was washed with DCM:MeOH (V:V=10:1) (30 mL), filtered and the filtrate was concentrated under reduced pressure to give 5-chloro-1-(1-ethyl-4,4-difluoro-3-piperidyl)pyrazol-4-amine as a red solid. LCMS: RT 1.150 min, m/z=265.1 [M+H]$^+$.

N2-[5-chloro-1-[(3S)-1-ethyl-4,4-difluoro-3-piperidyl]pyrazol-4-yl]-N4-ethyl-5-(trifluoromethyl)pyrimidine-2,4-diamine and N$_2$-[5-chloro-1-[(3R)-1-ethyl-4,4-difluoro-3-piperidyl]pyrazol-4-yl]-N4-ethyl-5-(trifluoromethyl)pyrimidine-2,4-diamine To a mixture of 5-chloro-1-(1-ethyl-4,4-difluoro-3-piperidyl)pyrazol-4-amine (0.13 g, 491.12 µmol) and 2-chloro-N-ethyl-5-(trifluoromethyl)pyrimidin-4-amine (110 mg, 491.12 µmol) in 1,4-dioxane (3 mL) was added p-TsOH.H$_2$O (25 mg, 147.33 µmol) at 20° C. and the mixture was stirred at 90° C. for 5 h. The mixture was adjusted to pH=7-8 with sat. aq. $NaHCO_3$ and the aqueous phase was extracted with EtOAc (3×5 mL). The combined organic phase was washed with brine (8 mL), dried over anhydrous $Na_2SO_4$, filtered and concentrated under reduced pressure. The residue was purified by prep-TLC (SiO$_2$, EtOAc) to give desired compound as a white syrup, which was further separated by SFC to give N2-[5-chloro-1-[(3S)-1-ethyl-4,4-difluoro-3-piperidyl]pyrazol-4-yl]-N4-ethyl-5-(trifluoromethyl)pyrimidine-2,4-diamine as a white syrup and N$_2$-[5-chloro-1-[(3R)-1-ethyl-4,4-difluoro-3-piperidyl]pyrazol-4-yl]-N4-ethyl-5-(trifluoromethyl)pyrimidine-2,4-diamine.

SFC, First Eluting Isomer:
$^1$H NMR (400 MHz, CHLOROFORM-d): δ 8.23 (br s, 1H), 8.13 (s, 1H), 6.72 (br s, 1H), 5.14 (br s, 1H), 4.64-4.79 (m, 1H), 3.48-3.64 (m, 2H), 3.14 (br d, J=8.41 Hz, 2H), 2.99 (br d, J=10.67 Hz, 1H), 2.60 (q, J=7.15 Hz, 2H), 2.35-2.50 (m, 1H), 2.04-2.34 (m, 2H), 1.27 (t, J=7.22 Hz, 3H), 1.13 (t, J=7.15 Hz, 3H). HPLC: RT: 1.116 min MS: m/z=454.4 [M+H]$^+$. SFC: Retention Time: 1.621 min.

SFC, Second Eluting Isomer:

¹H NMR (400 MHz, CHLOROFORM-d): δ 8.23 (br s, 1H), 8.14 (s, 1H), 6.71 (br s, 1H), 5.13 (br s, 1H), 4.60-4.81 (m, 1H), 3.49-3.61 (m, 2H), 3.15 (br d, J=8.28 Hz, 2H), 2.99 (br d, J=11.80 Hz, 1H), 2.60 (q, J=7.15 Hz, 2H), 2.43 (br t, J=12.05 Hz, 1H), 2.06-2.33 (m, 2H), 1.27 (t, J=7.22 Hz, 3H), 1.13 (t, J=7.15 Hz, 3H). HPLC: Retention Time: 1.108 min. MS: m/z=454.4 [M+H]⁺. SFC: Retention Time: 1.785 min.

Example 15

Synthesis of (1S,2R)-2-[4-[(5-bromo-4-methoxy-pyrimidin-2-yl)amino]-3-cyclopropyl-pyrazol-1-yl]cyclopropanecarbonitrile and (1R,2S)-2-[4-[(5-bromo-4-methoxy-pyrimidin-2-yl)amino]-3-cyclopropyl-pyrazol-1-yl]cyclopropanecarbonitrile (213 and 214)

3-cyclopropyl-4-nitro-1-vinyl-pyrazole

To a mixture of 3-cyclopropyl-4-nitro-1H-pyrazole (7 g, 45.71 mmol) and benzyl triethyl ammonium chloride (1.04 g, 4.57 mmol) in 1,2-dichloroethane (50 mL) was added NaOH (9.14 g, 228.55 mmol) and water (9 mL) at 20° C. under N₂. The mixture was stirred at 80° C. for 8 h. The reaction mixture was filtered and the filtrate was concentrated. The crude product was purified by silica gel column chromatography (PE:EtOAc=100:1 to 1:1) to give 3-cyclopropyl-4-nitro-1-vinyl-pyrazole as a yellow solid. ¹H NMR (400 MHz, CDCl₃): δ ppm 8.23 (s, 1H), 6.87 (dd, J=15.55, 8.71 Hz, 1H), 5.70, (d, J=15.66 Hz, 1H), 5.06 (d, J=8.60 Hz, 1H), 2.53-2.68 (m, 1H), 0.97-1.11 (m, 4H).

Ethyl (1S,2R)-2-(3-cyclopropyl-4-nitro-pyrazol-1-yl)cyclopropanecarboxylate and ethyl (1S,2S)-2-(3-cyclopropyl-4-nitro-pyrazol-1-yl)cyclopropanecarboxylate To a mixture of 3-cyclopropyl-4-nitro-1-vinyl-pyrazole (4.7 g, 26.23 mmol) and 3-[3-(2-carboxy-2-methyl-propyl)phenyl]-2,2-dimethyl-propanoic acid;rhodiorhodium (200 mg, 262.31 µmol) in DCM (100 mL) was added dropwise ethyl 2-diazoacetate (17.96 g, 157.39 mmol) in DCM (30 mL) at 20° C. under N₂ for 3 h. The mixture was stirred at 20° C. for 12 h. The mixture was concentrated. The residue was purified by silica gel column chromatography (PE:EtOAc=100:1 to 1:1) to give ethyl (1S*,2R*)-2-(3-cyclopropyl-4-nitro-pyrazol-1-yl)cyclopropanecarboxylate and ethyl (1S*,2S*)-2-(3-cyclopropyl-4-nitro-pyrazol-1-yl)cyclopropanecarboxylate as a brown oil.

(1S*,2R*)-2-(3-cyclopropyl-4-nitro-pyrazol-1-yl)cyclopropanecarboxylate

NMR (400 MHz, CDCl₃): δ 8.15 (s, 1H), 4.12-4.37 (m, 1H), 3.97-4.07 (m, 2H), 3.90 (td, J=7.50, 5.71 Hz, 1H), 2.43-2.71 (m, 1H), 2.13-2.37 (m, 1H), 1.88-2.07 (m, 1H), 1.59 (td, J=8.06, 6.46 Hz, 1H), 1.23-1.36 (m, 1H), 1.17 (t, J=7.15 Hz, 3H), 0.84-1.06 (m, 4H).

(1S*,2S*)-2-(3-cyclopropyl-4-nitro-pyrazol-1-yl)cyclopropanecarboxylate

¹H NMR (400 MHz, CDCl₃): δ 8.18 (s, 1H), 4.08-4.32 (m, 3H), 3.98 (ddd, J=7.97, 4.89, 3.07 Hz, 1H), 2.50-2.65 (m, 1H), 2.30 (ddd, J=9.54, 6.27, 3.01 Hz, 1H), 1.79 (dt, J=9.91, 5.21 Hz, 1H), 1.65 (dt, J=8.03, 5.96 Hz, 1H), 1.24-1.36 (m, 4H), 0.92-1.10 (m, 4H).

(1S,2R)-2-(3-cyclopropyl-4-nitro-pyrazol-1-yl)cyclopropanecarboxylic acid

To a mixture of ethyl (1S,2R)-2-(3-cyclopropyl-4-nitro-pyrazol-1-yl)cyclopropanecarboxylate (2.2 g, 8.29 mmol) in 1,4-dioxane (20 mL) was added HCl (2 M, 20 mL) at 20° C. under N₂. The mixture was stirred at 60° C. for 12 h. The mixture was concentrated to give (1S,2R)-2-(3-cyclopropyl-4-nitro-pyrazol-1-yl)cyclopropanecarboxylic acid as a brown solid. ¹H NMR (400 MHz, DMSO): δ 8.84 (s, 1H), 4.01-4.10 (m, 1H), 2.39-2.46 (m, 1H), 2.02-2.10 (m, 1H), 1.98 (q, J=6.03 Hz, 1H), 1.46-1.55 (m, 1H), 0.93-1.07 (m, 2H), 0.76-0.89 (m, 2H).

(1S,2R)-2-(3-cyclopropyl-4-nitro-pyrazol-1-yl)cyclopropanecarboxamide

To a mixture of (1S,2R)-2-(3-cyclopropyl-4-nitro-pyrazol-1-yl)cyclopropanecarboxylic acid (2 g, 8.43 mmol), NH₄Cl (2.71 g, 50.59 mmol) and DIPEA (6.54 g, 50.59 mmol) in DMF (20 mL) was added HATU (6.41 g, 16.86 mmol) at 20° C. under N₂. The mixture was stirred at 20° C. for 4 h. The mixture was poured into ice-water (100 mL). The aqueous phase was extracted with EtOAc (3×50 mL). The combined organic phase was washed with brine (3×50 mL), dried with anhydrous Na₂SO₄, filtered and concentrated under reduced pressure to give (1S,2R)-2-(3-cyclopropyl-4-nitro-pyrazol-1-yl)cyclopropanecarboxamide as a brown solid. ¹H NMR (400 MHz, DMSO): δ 8.67 (s, 1H), 7.65 (br s, 1H), 6.87 (br s, 1H), 3.81-3.98 (m, 1H), 2.38-2.47 (m, 1H), 2.04 (q, J=7.57 Hz, 1H), 1.93 (q, J=5.73 Hz, 1H), 1.37 (td, J=8.05, 5.95 Hz, 1H), 1.21-1.29 (m, 1H), 0.94-1.01 (m, 2H), 0.78-0.84 (m, 1H).

(1S, 2R)-2-(3-cyclopropyl-4-nitro-pyrazol-1-yl)cyclopropanecarbonitrile

To a mixture of (1S, 2R)-2-(3-cyclopropyl-4-nitro-pyrazol-1-yl) cyclopropanecarboxamide (1.7 g, 7.2 mmol) in EtOAc (80 mL) was added T3P (18.32 g, 28.79 mmol, 17.12 mL, 50% purity) at 20° C. under N₂. The mixture was stirred at 75° C. for 12 h. The mixture was poured into aq. NaHCO₃ (200 mL). The aqueous phase was extracted with EtOAc (3×50 mL). The combined organic phase was washed with brine (150 mL), dried with anhydrous Na₂SO₄, filtered and concentrated under reduced pressure. The residue was purified by silica gel column chromatography (PE:EtOAc=100:1 to 1:1) to give (1S,2R)-2-(3-cyclopropyl-4-nitro-pyrazol-1-yl)cyclopropanecarbonitrile as a white solid. LCMS: RT 1.20 min, m/z=219.2 [M+H]⁺. ¹H NMR (400 MHz, CDCl₃): δ 8.26 (s, 1H), 3.90-4.09 (m, 1H), 2.62 (tt, J=8.05, 5.29 Hz, 1H), 2.10-2.20 (m, 1H), 2.01 (dt, J=9.43, 6.64 Hz, 1H), 1.75 (dt, J=9.26, 7.39 Hz, 1H), 1.00-1.11 (m, 4H).

(1S, 2R)-2-(4-amino-3-cyclopropyl-pyrazol-1-yl)cyclopropanecarbonitrile

To a mixture of (1S,2R)-2-(3-cyclopropyl-4-nitro-pyrazol-1-yl)cyclopropanecarbonitrile (0.8 g, 3.67 mmol) and Fe (1.02 g, 18.33 mmol) in EtOH (20 mL) and water (5 mL) was added NH₄Cl (981 mg, 18.33 mmol) at 20° C. under N₂. The mixture was stirred at 75° C. for 1 h. The mixture was filtered and the filtrate was concentrated. The residue was washed with DCM: MeOH (10:1, 3×10 mL), filtered and the filtrate was concentrated under reduced pressure to give (1S,2R)-2-(4-amino-3-cyclopropyl-pyrazol-1-yl) cyclopropanecarbonitrile (0.75 g, crude) as a brown oil. LCMS: RT 0.81 min, m/z=189.3 [M+H]$^+$. $^1$H NMR (400 MHz, CDCl$_3$): δ 6.97-7.15 (m, 1H), 3.74-3.91 (m, 1H), 2.03 (q, J=6.25 Hz, 1H), 1.80 (dt, J=9.43, 6.42 Hz, 1H), 1.64-1.74 (m, 1H), 1.54-1.63 (m, 1H), 0.78-0.93 (m, 4H).

(1S,2R)-2-[4-[(5-bromo-4-methoxy-pyrimidin-2-yl)amino]-3-cyclopropyl-pyrazol-1-yl]cyclopropanecarbonitrile and (1R,2S)-2-[4-[(5-bromo-4-methoxy-pyrimidin-2-yl)amino]-3-cyclopropyl-pyrazol-1-yl]cyclopropanecarbonitrile To a mixture of (1S,2R)-2-(4-amino-3-cyclopropyl-pyrazol-1-yl)cyclopropanecarbonitrile (0.1 g, 531.27 μmol) and 5-bromo-2-chloro-4-methoxy-pyrimidine (119 mg, 531.27 μmol) in 1,4-dioxane (2 mL) was added p-TsOH.H$_2$O (30 mg, 159.38 μmol) at 20° C. under N$_2$. The mixture was stirred at 85° C. for 4 h. The mixture was poured into aq. NaHCO$_3$ (5 mL) and extracted with EtOAc (3×5 mL). The combined organic phase was washed with brine (10 mL), dried with anhydrous Na$_2$SO$_4$, filtered and concentrated under reduced pressure. The residue was purified by silica gel column chromatography (PE:EtOAc=100:1 to 1:1) and separated by SFC to give (1S,2R)-2-[4-[(5-bromo-4-methoxy-pyrimidin-2-yl)amino]-3-cyclopropyl-pyrazol-1-yl]cyclopropanecarbonitrile and (1R,2S)-2-[4-1(5-bromo-4-methoxy-pyrimidin-2-yl)amino]-3-cyclopropyl-pyrazol-1-yl]cyclopropanecarbonitriles.

SFC, First Eluting Isomer:
$^1$H NMR (400 MHz, CDCl$_3$): δ 8.23 (s, 1H), 8.01 (s, 1H), 6.76 (br s, 1H), 4.05 (s, 3H), 3.85-3.97 (m, 1H), 2.11 (q, J=6.27 Hz, 1H), 1.88 (dt, J=9.29, 6.46 Hz, 1H), 1.60-1.78 (m, 2H), 0.84-0.97 (m, 4H). LCMS: reaction time: 1.475 min. MS: [M+H]$^+$ m/z: 375.2.

SFC, First Eluting Isomer:
$^1$H NMR (400 MHz, CDCl$_3$): δ 8.22 (s, 1H), 8.01 (s, 1H), 6.77 (br s, 1H), 4.05 (s, 3H), 3.86-3.96 (m, 1H), 2.11 (q, J=6.27 Hz, 1H), 1.88 (dt, J=9.29, 6.53 Hz, 1H), 1.61-1.77 (m, 2H), 0.85-0.97 (m, 4H). LCMS: reaction time: 1.465 min. MS: [M+H]$^+$ m/z: 375.2.

The other compounds of Table 1A, 1B, 2A and 2B were, or can be, prepared according to the Examples above and/or general procedures described herein using the appropriate starting materials.

Example 16

Biochemical Assay of the Compounds

Materials:
LRRK2 G2019S enzyme
Substrate (LRRKtide)
ATP
TR-FRET dilution buffer
pLRRKtide antibody
384-well assay plate
DMSO
Enzyme Reaction Conditions
50 mM Tris pH 7.5, 10 mM MgCl$_2$, 1 mM EGTA, 0.01% Brij-35, 2 mM DTT
5 nM LRRK2
134 μM ATP
60 minute reaction time
23° C. reaction temperature
10 μL total reaction volume Detection Reaction Conditions
1× TR-FRET dilution buffer
10 mM EDTA
2 nM antibody
23° C. reaction temperature
10 μL total reaction volume Compounds were prepared by initially diluting to 1 mM with DMSO. 35 μL of reference compound solution, 35 μL of test compound solution, and 35 μL HPE were successively added to the source plate (384-well assay plate, Labcyte). The plates were centrifuged at 2500 rpm for 1 minute and sealed in foil. POD was used to perform a 3.162 fold serial dilution and 100 nL of reference compound solution, test compound solution, HPE and ZPE were transferred to assay plates. The assay plate was centrifuged at 2500 rpm for 1 minute, and sealed with foil.

To perform the enzyme reaction, 5 μL of LRRKtide substrate and kinase mixture in assay buffer was added to all wells of the assay plate. The plate was centrifuged to concentrate the mixture at the bottom of the wells. The assay plate was incubated at 23° C. for 20 minutes. Following incubation, 5 μL of 2×ATP in assay buffer was added to each well, and plates were centrifuged to concentrate the mixture at the bottom of the wells. The plate was incubated at 23° C. for 60 minutes.

To perform the detection of the reaction, EDTA completely mixed in TR-FRET dilution buffer was added to antibody reagent. 10 μL of detection reagent was added to all wells of each well of the assay plate and the plate was centrifuged to concentrate the mixture at the bottom of the wells. The plate was then incubated at 23° C. for 60 minutes. Plates were read on Perkin Elmer Envision 2104 instrument in TR-FRET mode using a 340 nm excitation filter, 520 nm fluorescence emission filter, and 490 or 495 nm terbium emission filter.

Several of the compounds disclosed herein were tested according to the above methods and found to exhibit an LRRK2 G2019S IC$_{50}$ as indicated in Table 3. In the table below, activity is provided as follows: +++=IC$_{50}$ less than 30 nM; ++=IC$_{50}$ between 30 nM and 60 nM; +=IC$_{50}$ greater than 60 nM.

TABLE 3

| No. | LRRK2 TR-FRET IC$_{50}$ (nM) | MS [M + 1]+ |
|---|---|---|
| 1 | +++ | 396.2 |
| 2 | + | 396.3 |
| 3 | +++ | 353.1 |
| 4 | +++ | 353.1 |
| 5 | +++ | 392.1 |
| 6 | + | 378.1 |
| 7 | +++ | 378.1 |
| 8 | +++ | 325.1 |
| 9 | +++ | 409 |
| 10 | + | 409.1 |
| 11 | +++ | 389.1 |
| 12 | +++ | 389.1 |
| 13 | +++ | 389.1 |
| 14 | +++ | 396.2 |
| 15 | +++ | 395.2 |
| 16 | +++ | 341.2 |
| 17 | +++ | 341.1 |
| 18 | +++ | 409.2 |
| 19 | +++ | 350.2 |
| 20 | +++ | 355.2 |
| 21 | +++ | 378.1 |
| 22 | +++ | 404.2 |
| 23 | +++ | 404.3 |
| 24 | +++ | 404.2 |

TABLE 3-continued

| No. | LRRK2 TR-FRET IC$_{50}$ (nM) | MS [M + 1]+ |
|---|---|---|
| 25 | +++ | 387.3 |
| 26 | +++ | 366.2 |
| 27 | +++ | 366.1 |
| 28 | +++ | 468.2 |
| 29 | +++ | 468.2 |
| 30 | ++ | 371.2 |
| 31 | ++ | 371.2 |
| 32 | +++ | 352.1 |
| 33 | +++ | 410.1 |
| 34 | +++ | 399.2 |
| 35A | +++ | 366.2 |
| 35B | +++ | 366.2 |
| 37 | +++ | 349.0 |
| 38 | +++ | 366.1 |
| 39A | +++ | 384.2 |
| 40 | +++ | 352.2 |
| 41 | +++ | 352.1 |
| 42 | +++ | 350.1 |
| 43 | +++ | 364.1 |
| 44 | +++ | 363.3 |
| 45 | +++ | 349.2 |
| 46 | +++ | 399.2 |
| 48 | +++ | 375.2 |
| 50 | +++ | 331.1 |
| 52A | +++ | 338.1 |
| 52B | +++ | 338.2 |
| 54A | +++ | 380.2 |
| 54B | +++ | 380.1 |
| 57 | +++ | 396.2 |
| 58 | +++ | 362.1 |
| 59 | +++ | 390.2 |
| 60 | +++ | 333.1 |
| 61 | +++ | 380.2 |
| 62 | +++ | 343.2 |
| 63 | +++ | 346.1 |
| 64A | +++ | 381.1 |
| 64B | +++ | 381.1 |
| 65 | +++ | 381.1 |
| 66 | +++ | 376.1 |
| 67 | +++ | 343.2 |
| 68 | +++ | 411.3 |
| 69 | +++ | 408.2 |
| 70 | +++ | 398.2 |
| 71 | +++ | 410.2 |
| 72 | +++ | 332.1 |
| 73 | +++ | 400.1 |
| 74 | +++ | 368.3 |
| 75 | +++ | 409.1 |
| 76 | +++ | 404.1 |
| 77 | +++ | 408.2 |
| 78 | +++ | 422.3 |
| 79 | +++ | 421.1 |
| 80 | +++ | 346.2 |
| 81 | +++ | 423.0 |
| 82 | +++ | 399.2 |
| 83 | +++ | 399.2 |
| 84 | +++ | 380.2 |
| 85 | +++ | 413.1 |
| 86 | +++ | 424.3 |
| 87 | +++ | 354.2 |
| 88 | +++ | 415.2 |
| 89 | +++ | 359.2 |
| 90 | +++ | 382.1, 384.0 |
| 91 | +++ | 374.3 |
| 92 | +++ | 434.4 |
| 93 | +++ | 390.1, 392.1 |
| 94 | +++ | 394.2 |
| 95 | +++ | 390.1, 392.1 |
| 96 | +++ | 429.1 |
| 97 | +++ | 434.2 |
| 98 | +++ | 385.1 |
| 99 | +++ | 391.3 |
| 100 | +++ | 385.2 |
| 101 | +++ | 434.2 |
| 102 | +++ | 382.1, 384 |
| 103 | +++ | 382.2 |
| 104 | +++ | 411.2 |
| 105 | +++ | 391.2 |
| 106 | +++ | 489.3 |
| 107 | +++ | 378.3 |
| 108 | +++ | 411.2 |
| 109 | +++ | 273.2 |
| 110 | +++ | 417.25 |
| 111 | +++ | 401.1 |
| 112 | +++ | 391.1 |
| 113 | +++ | 397.2 |
| 114 | +++ | 423.1 |
| 115 | +++ | 423.1 |
| 116 | +++ | 434.4 |
| 117 | +++ | 405.3 |
| 118 | +++ | 380.2 |
| 119 | +++ | 371.2 |
| 120 | +++ | 382.2 |
| 121 | +++ | 489.3 |
| 122 | +++ | 397.2 |
| 123 | +++ | 391.2 |
| 124 | +++ | 371.2 |
| 125 | +++ | 385.2 |
| 126 | +++ | 433.8 |
| 127 | +++ | 436.3 |
| 128 | +++ | 419.2 |
| 129 | +++ | 410.2 |
| 130 | +++ | 384.2 |
| 131 | +++ | 380.2 |
| 132 | +++ | 391.1 |
| 133 | + | 338.1 |
| 134 | +++ | 371.2 |
| 135 | + | 355.2 |
| 136 | ++ | 410.2 |
| 137 | +++ | 408.2 |
| 138 | +++ | 408.2 |
| 139 | +++ | 433.1 |
| 140 | +++ | 443.1, 445.2 |
| 141 | +++ | 392.2 |
| 142 | +++ | 394.2 |
| 143 | +++ | 411.2 |
| 144 | +++ | 411.2 |
| 145 | +++ | 383.3 |
| 146 | +++ | 418.2, 420.2 |
| 147 | +++ | 418.2, 420.2 |
| 148 | +++ | 393.1 |
| 149 | ++ | 410.2 |
| 150 | +++ | 421.1, 423.1 |
| 151 | +++ | 421.1, 423.1 |
| 152 | +++ | 378.2 |
| 153 | +++ | 396.2 |
| 154 | +++ | 432.2 |
| 155 | +++ | 397.2 |
| 156 | +++ | 397.2 |
| 157 | ++ | 419.2, 421.2 |
| 158 | +++ | 408.1 |
| 159 | +++ | 442.1, 444.1 |
| 160 | ++ | 408.2, 410.1 |
| 161 | +++ | 408.1, 410.1 |
| 162 | +++ | 409 |
| 163 | +++ | 395.1 |
| 164 | +++ | 378.3 |
| 165 | +++ | 409.3 |
| 166 | + | 433.2 |
| 167 | +++ | 433.2 |
| 168 | +++ | 395.2 |
| 169 | +++ | 425.3 |
| 170 | +++ | 396.3 |
| 171 | + | 434.3 |
| 172 | +++ | 434.3 |
| 173 | +++ | 388.2 |
| 174 | +++ | 388.3 |
| 175 | +++ | 374.2 |
| 176 | +++ | 374.3 |
| 177 | + | 419.3 |
| 178 | +++ | 419.3 |
| 179 | +++ | 343.3 |
| 180 | ++ | 343.2 |
| 181 | +++ | 352.1 |

TABLE 3-continued

| No. | LRRK2 TR-FRET IC$_{50}$ (nM) | MS [M + 1]+ |
|---|---|---|
| 182 | +++ | 394.3 |
| 183 | +++ | 394.2 |
| 184 | +++ | 386.2 |
| 185 | +++ | 386.2 |
| 186 | +++ | 374.3 |
| 187 | +++ | 390.1, 392.1 |
| 188 | ++ | 394.2 |
| 189 | ++ | 394.2 |
| 190 | +++ | 345.1 |
| 191 | +++ | 385.3 |
| 192 | +++ | 399.3 |
| 193 | ++ | 374.3 |
| 194 | +++ | 383.2 |
| 195 | +++ | 369.2 |
| 196 | +++ | 434.4 |
| 197 | +++ | 434.4 |
| 198 | +++ | 420.4 |
| 199 | ++ | 420.4 |
| 200 | +++ | 406.4 |
| 201 | +++ | 406.4 |
| 202 | +++ | 440.4 |
| 203 | +++ | 440.4 |
| 204 | +++ | 454.4 |
| 205 | +++ | 454.4 |
| 206 | +++ | 372.3 |
| 207 | +++ | 372.3 |
| 208 | +++ | 364.3 |
| 209 | +++ | 364.3 |
| 210 | +++ | 414.3 |
| 211 | +++ | 414.3 |
| 212 | +++ | 376.2 |
| 213 | +++ | 375.2 |
| 214 | +++ | 388.3 |
| 215 | +++ | 388.3 |
| 216 | +++ | 403.3 |
| 217 | +++ | 403.3 |
| 218 | +++ | 396.2 |

Example 17

Metabolic Stability

Metabolic stability of compounds was evaluated in human liver microsomes (from Corning or XenoTech, LLC) using a 96-well plate assay format. Compounds were incubated at 37° C. at 1 µM final concentration in the microsomal matrix (0.5 mg/mL total protein) in the presence or absence of NADPH cofactor. An NADPH regenerating system, comprised of NADP, MgCl$_2$, isocitric acid, and isocitrate dehydrogenase, was used in the assay. Enzymatic reactions were conducted for 0, 5, 10, 20, 30, or 60 min before termination by addition of acetonitrile containing tolbutamide and labetalol internal standards (100 ng/mL). After shaking for 10 min, plates were subjected to centrifugation (4000 rpm at 4° C.) for 20 min and supernatants were mixed 1:3 with HPLC grade water. Samples were analyzed by LC-MS/MS using appropriate MRM transitions for each analyte and internal standard (IS). Analyte/IS peak area ratios were used to determine percent compound remaining at each time point. Intrinsic clearance (Cl$_{int}$; expressed as mL·min$^{-1}$·mg$^{-1}$) was calculated from the first order elimination constant (k, min$^{-1}$) of test article decay and the volume of the incubation. These values were scaled to intrinsic organ clearance (Cl$_{int}$) using human specific scaling factors (48.8 mg microsomal protein per g liver; 25.7 g liver per kg body weight). Organ Cl$_{int}$ was subsequently converted to hepatic clearance (CL$_{hep}$, mL·min-1·kg-1) using the well-stirred model of hepatic elimination, where Q$_h$ is human hepatic blood flow (20.7 mL·min-1·kg-1).

$$CL_{hep} = \frac{Q_h * CL_{int}}{(Q_h + CL_{int})}$$

CL$_{hep}$ is the projected human clearance in the liver based on the above in vitro assay. A lower value is indicative of less compound being removed by the liver. Surprisingly, compounds having a C5-pyrazole attachment to the aminopyrimidine core resulted in a lower clearance (i.e., improved stability) as compared to compounds having a C4-pyrazole attachment to the aminopyrimidine core, without a significant change in potency.

TABLE 4

| Compound No. | Structure | LRRK2 TR-FRET IC$_{50}$ (nM) | Human Liver microsomes CL$_{hep}$ (mL/min/kg) |
|---|---|---|---|
| 122 | (First eluting isomer) | 0.72 | 9.856 |

TABLE 4-continued

| Compound No. | Structure | LRRK2 TR-FRET IC$_{50}$ (nM) | Human Liver microsomes CL$_{hep}$ (mL/min/kg) |
|---|---|---|---|
| 155 | (First eluting isomer) | 1.95 | 5.519 |
| 114 | (First eluting isomer) | 1.05 | 16.508 |
| 150 | (First eluting isomer) | 1.22 | 11.077 |
| 104 | (First eluting isomer) | 0.96 | 11.59 |

TABLE 4-continued

| Compound No. | Structure | LRRK2 TR-FRET IC$_{50}$ (nM) | Human Liver microsomes CL$_{hep}$ (mL/min/kg) |
| --- | --- | --- | --- |
| 143 | (First eluting isomer) | 1.21 | 7.81 |
| 93 | 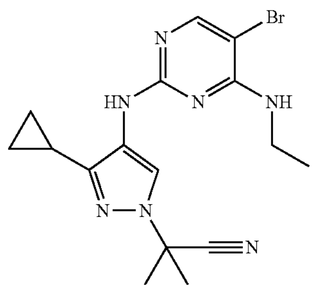 [SMILES: CCNc1nc(Nc2cn(C(C)(C)C#N)nc2C2CC2)ncc1Br] | 1.87 | 17.663 |
| 141 | 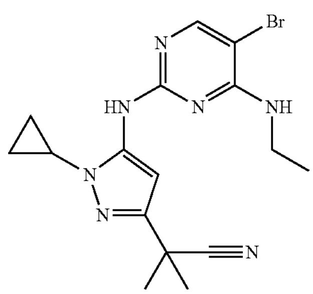 [SMILES: CCNc1nc(Nc2cc(C(C)(C)C#N)nn2C2CC2)ncc1Br] | 3.94 | 13.508 |
| 118 | 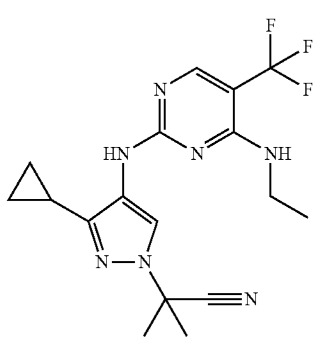 [SMILES: CCNc1nc(Nc2cn(C(C)(C)C#N)nc2C2CC2)ncc1C(F)(F)F] | 1.55 | 7.81 |

TABLE 4-continued

| Compound No. | Structure | LRRK2 TR-FRET IC$_{50}$ (nM) | Human Liver microsomes CL$_{hep}$ (mL/min/kg) |
|---|---|---|---|
| 131 | 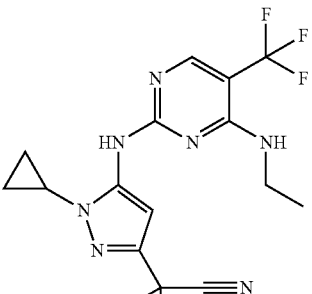 | 4.98 | 2.237 |

Example 18

MDR1-MDCK Permeability

The blood brain barrier (BBB) separates circulating blood from the extracellular fluid of the central nervous system (CNS). The passive membrane permeability (Papp) and MDR1 (P-glycoprotein) substrate efflux potential were determined using the MDR1-MDCK cell line as an in vitro model of the effective permeability of a compound through the BBB. A bidirectional assay was conducted in pre-plated MDR1-MDCK cells using a 12 or 96-well plate in the absence or presence of MDR1 inhibitor (GF120918 or Valspodar). Assays were run in duplicate in transport buffer (HBSS, pH 7.4) for 90 or 120 min (minutes) at 37° C., using a test article concentration of 1 μM. Monolayer integrity was confirmed using Lucifer yellow, and appropriate positive controls for passive permeability and MDR1 transport were included in each experiment. Following incubation, samples from donor and receiver compartments were removed and quenched with acetonitrile containing an appropriate internal standard (IS). Protein was precipitated by centrifugation for 10 min at 3220 g, and supernatants were diluted in ultra-pure water (if necessary) prior to analysis by LC-MS/MS using appropriate MRM transitions for analytes and IS. Papp (apparent permeability expressed in cm/sec [centimeter/second]) values were calculated according to the following equation:

$$P_{app} \text{ (cm/sec)} = \frac{dC_R}{dt} \times \frac{V_R}{(\text{Area} \times C_A)} \text{ or } \frac{V_R}{\text{Area} \times \text{Time}} \times \frac{C_R}{C_o}$$

where $V_R$ is the solution volume in the receiver chamber (apical or basolateral side), Area is the surface area for the insert membrane), Time is incubation time expressed in seconds, $C_R$ is the peak area ratio (analyte/IS) in the receiver chamber, $C_A$ is the average of the initial and final concentrations in the donor chamber, and $C_O$ is the initial peak area ratio in the donor chamber. $P_{app}$ was determined in both the apical to basolateral (A→B) and basolateral to apical (B→A) directions.

Monolayer efflux ratios (ER) were derived using the following equation:

$$ER = \left[ \frac{P_{app} \ (B \to A)}{P_{app} \ (A \to B)} \right]$$

Compounds with an MDR1-MDCK efflux ratio of less than or equal to five are likely to demonstrate ability to cross the blood-brain-barrier.

Compounds having the 1,2,3-triazole substituent were surprisingly brain penetrant as compared to molecules having a 1,2,4-triazole moiety.

TABLE 5

| Compound No. | Structure | LRRK2 TR-FRET IC$_{50}$ (nM) | Human liver microsomes CL$_{hep}$ (mL/min/kg) | MDR1 ER |
|---|---|---|---|---|
| 172 | 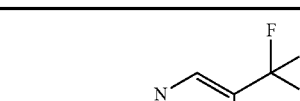 | 1.47 | 19.9 | 42 |

TABLE 5-continued

| Compound No. | Structure | LRRK2 TR-FRET IC$_{50}$ (nM) | Human liver microsomes CL$_{hep}$ (mL/min/kg) | MDR1 ER |
|---|---|---|---|---|
| | (Second eluting isomer) | | | |
| 34 | 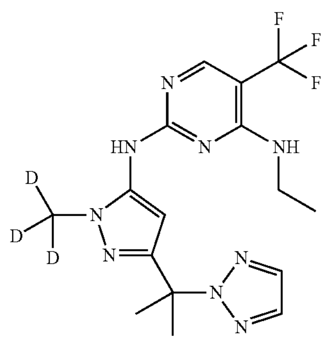 [SMILES: [2H]C([2H])([2H])n1nc(C(C)(C)n2nccn2)cc1Nc1ncc(C(F)(F)F)c(NCC)n1] | 2.31 | 0.75 | 4.8 |
| 68 | 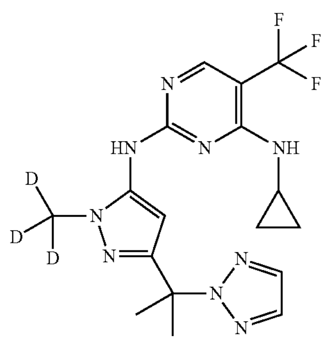 [SMILES: [2H]C([2H])([2H])n1nc(C(C)(C)n2nccn2)cc1Nc1ncc(C(F)(F)F)c(NC2CC2)n1] | 2.23 | 3.18 | 4.01 |
| 78 | 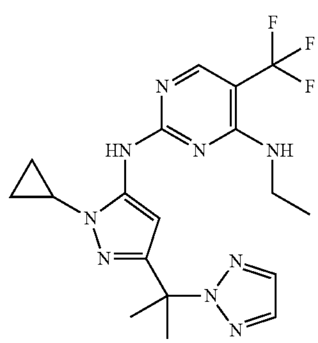 [SMILES: CCNc1nc(Nc2cc(C(C)(C)n3nccn3)nn2C2CC2)ncc1C(F)(F)F] | 3.69 | 4.81 | 2 |
| 27 | 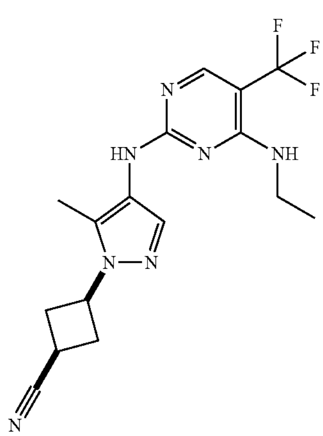 | 3.41 | 7.81 | 0.88 |

TABLE 5-continued

| Compound No. | Structure | LRRK2 TR-FRET IC$_{50}$ (nM) | Human liver microsomes CL$_{hep}$ (mL/min/kg) | MDR1 ER |
|---|---|---|---|---|
| 118 | 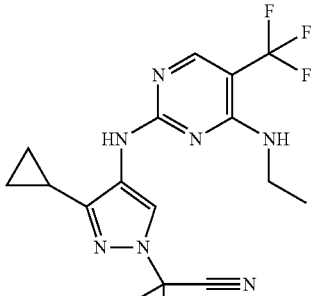 | 1.55 | 7.81 | 0.83 |
| 218 | 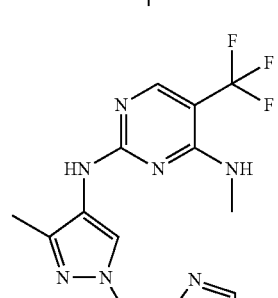 | 5.91 | 0 | 86.02 |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed:

1. A method for treating a disease or condition mediated, at least in part, by LRRK2, wherein the disease or condition is selected from the group consisting of Parkinson's disease, dementia, Alzheimer's disease, L-Dopa induced dyskinesia, and amyotrophic lateral sclerosis, the method comprising administering to a subject in need thereof an effective amount of a compound of formula Ia:

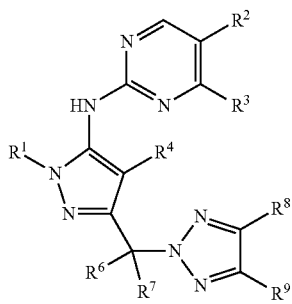

Ia or a pharmaceutically acceptable salt, deuterated analog, prodrug, stereoisomer, or a mixture of stereoisomers thereof, wherein:
$R^1$ is optionally substituted cycloalkyl or $C_{1-6}$ alkyl optionally substituted with halo;
$R^2$ is halo, cyano, optionally substituted $C_{1-6}$ alkyl, optionally substituted $C_{2-6}$ alkenyl, optionally substituted $C_{2-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —C(O)$R^{10}$, or —C(O)N($R^{11}$)($R^{12}$);
$R^3$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{11}$)($R^{12}$);
$R^4$ is hydrogen or halo;
$R^6$ and $R^7$ are each independently hydrogen or $C_{1-6}$ alkyl optionally substituted with halo;
$R^8$ and $R^9$ are each independently hydrogen, cyano, halo, optionally substituted $C_{1-6}$ alkyl, optionally substituted $C_{1-6}$ alkoxy, or optionally substituted heteroaryl;
$R^{10}$ is optionally substituted $C_{1-6}$ alkyl or optionally substituted $C_{1-6}$ alkoxy; and
$R^{11}$ and $R^{12}$ are each independently hydrogen, optionally substituted $C_{1-6}$ alkyl, or optionally substituted cycloalkyl.

2. The method of claim 1, wherein $R^6$ and $R^7$ are methyl.

3. The method of claim 1, wherein at least one of $R^8$ and $R^9$ is hydrogen.

4. The method of claim 3, wherein both $R^8$ and $R^9$ are hydrogen.

5. The method of claim 1, wherein $R^1$ is optionally substituted cyclopropyl or optionally substituted cyclobutyl.

6. The method of claim 5, wherein $R^1$ is cyclopropyl independently substituted with one or more halo, hydroxy, cyano, or heteroaryl.

7. The method of claim 6, wherein $R^1$ is cyclopropyl, cyclobutyl, hydroxycyclobut-3-yl, cyanocyclobut-3-yl, triazol-2yl-cyclobut-3-yl, triazol-1-yl-cyclobut-3-yl, or fluorocyclobut-3-yl.

8. The method of claim 1, wherein $R^1$ is $CD_3$, ethyl, prop-2-yl, or methyl optionally substituted with halo.

9. The method of claim 1, wherein $R^2$ is halo, cyano, or $C_{1-6}$ alkyl optionally substituted with one or more halo.

10. The method of claim 9, wherein $R^2$ is bromo.

11. The method of claim 9, wherein $R^2$ is —$CF_3$.

12. The method of claim 1, wherein $R^3$ is optionally substituted cycloalkyl, optionally substituted $C_{1-6}$ alkoxy, or —N($R^{11}$)($R^{12}$).

13. The method of claim 1, wherein $R^3$ is cyclopropyl, methoxy, 1,1-difluoroeth-2-ylamino, cyclopropylamino, —NH($CH_3$), or —NH($CH_2CH_3$).

14. The method of claim 1, wherein $R^4$ is hydrogen.

15. The method of claim 1, wherein $R^1$ is cycloalkyl independently substituted with one or more hydroxy, cyano, or heteroaryl; $R^2$ is halo or $C_{1-6}$ haloalkyl; $R^3$ is —N($R^{11}$)($R^{12}$) or $C_{1-6}$ alkoxy; and $R^4$ is H.

16. The method of claim 15, wherein $R^{12}$ is optionally substituted $C_{1-6}$ alkyl.

17. The method of claim 15, wherein $R^{11}$ is H and $R^{12}$ is ethyl.

18. The method of claim 1, wherein the compound is selected from:

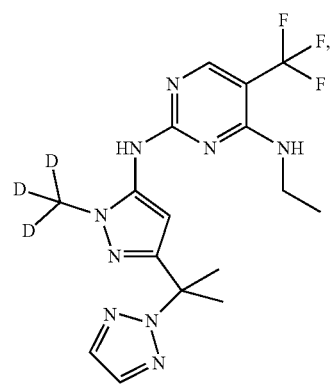

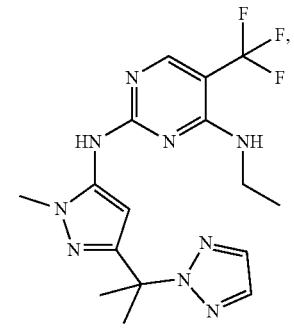

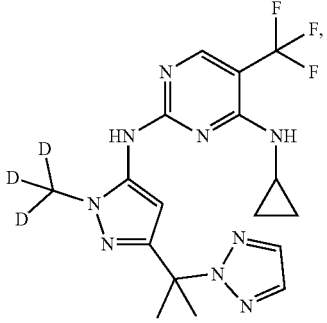

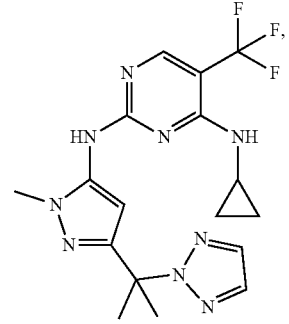

157
-continued
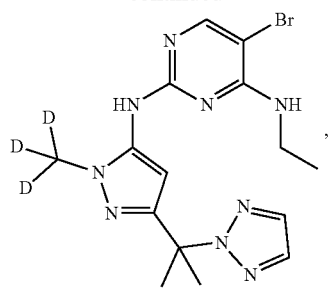
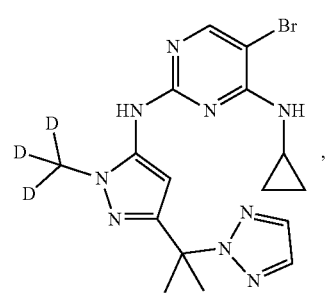
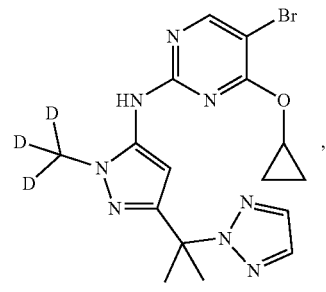
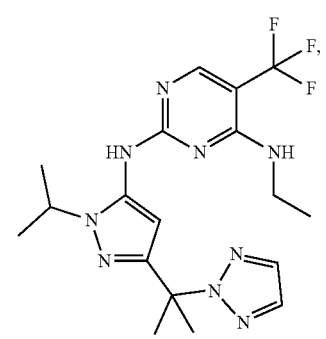
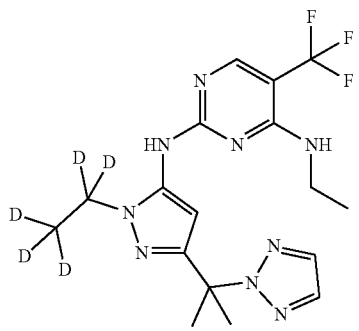
158
-continued
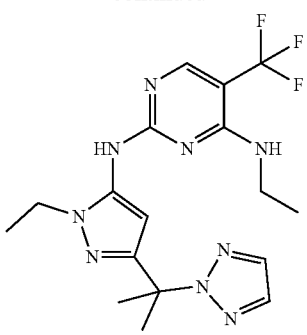
or a pharmaceutically acceptable salt, deuterated analog, prodrug, tautomer, stereoisomer, or a mixture of stereoisomers thereof.
19. The method of claim 1, wherein the compound is selected from:
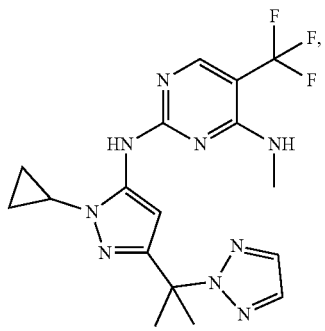
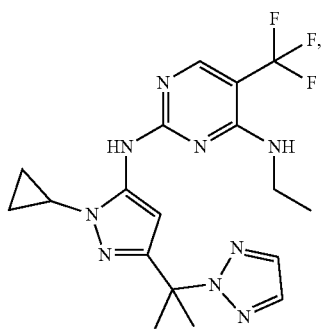
and
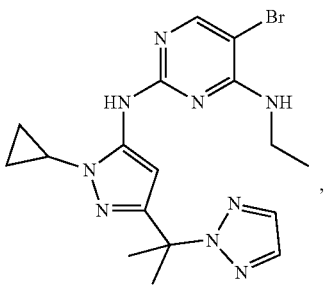

-continued

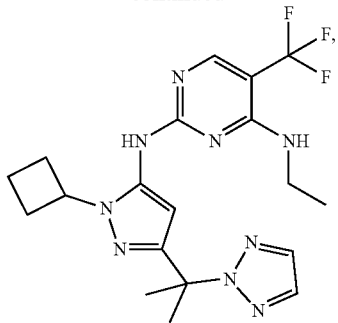

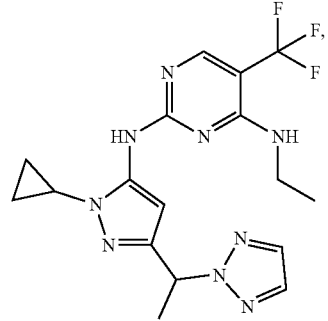

(First eluting isomer)

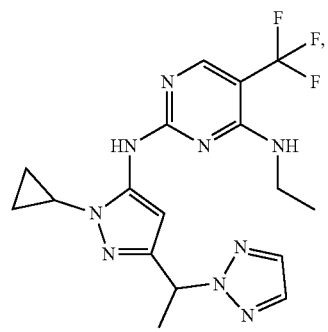

(Second eluting isomer)

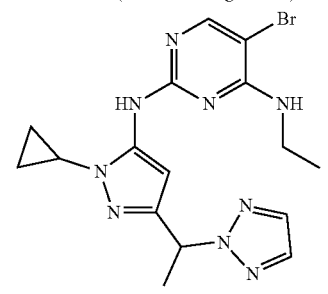

(First eluting isomer)

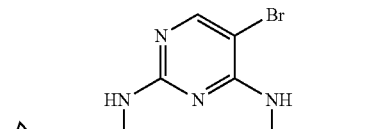

and

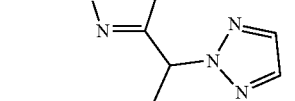

(Second eluting isomer)

-continued

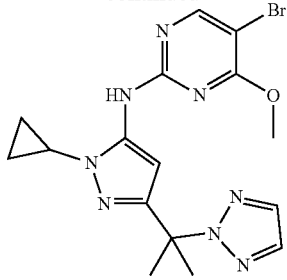

or a pharmaceutically acceptable salt, deuterated analog, prodrug, tautomer, stereoisomer, or a mixture of stereoisomers thereof.

20. A method for treating a disease or condition mediated, at least in part, by LRRK2, wherein the disease or condition is selected from the group consisting of Parkinson's disease, dementia, Alzheimer's disease, L-Dopa induced dyskinesia, and amyotrophic lateral sclerosis, the method comprising administering to a subject in need thereof an effective amount of a compound having the structure:

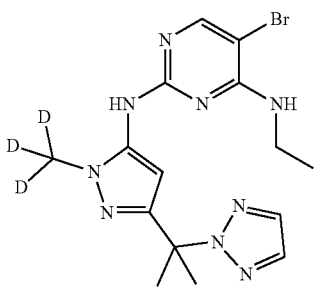 [SMILES: [2H]C([2H])([2H])n1nc(C(C)(C)n2nccn2)cc1Nc1ncc(Br)c(NCC)n1]

or a pharmaceutically acceptable salt thereof.

21. A method for treating a disease or condition mediated, at least in part, by LRRK2, wherein the disease or condition is selected from the group consisting of Parkinson's disease, dementia, Alzheimer's disease, L-Dopa induced dyskinesia, and amyotrophic lateral sclerosis, the method comprising administering to a subject in need thereof an effective amount of a compound having the structure:

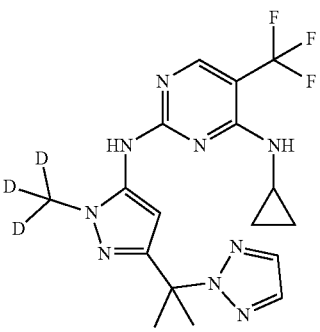 [SMILES: [2H]C([2H])([2H])n1nc(C(C)(C)n2nccn2)cc1Nc1ncc(C(F)(F)F)c(NC2CC2)n1]

or a pharmaceutically acceptable salt thereof.

22. A method for treating a disease or condition mediated, at least in part, by LRRK2, wherein the disease or condition is selected from the group consisting of Parkinson's disease, dementia, Alzheimer's disease, L-Dopa induced dyskinesia, and amyotrophic lateral sclerosis, the method comprising administering to a subject in need thereof an effective amount of a compound having the structure:

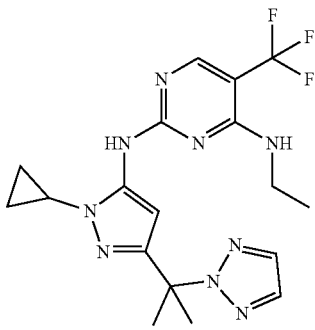 [SMILES: CCNc1nc(Nc2cc(C(C)(C)n3nccn3)nn2C2CC2)ncc1C(F)(F)F]

or a pharmaceutically acceptable salt thereof.

23. A method for treating a disease or condition mediated, at least in part, by LRRK2, wherein the disease or condition is selected from the group consisting of Parkinson's disease, dementia, Alzheimer's disease, L-Dopa induced dyskinesia, and amyotrophic lateral sclerosis, the method comprising administering to a subject in need thereof an effective amount of a compound having the structure:

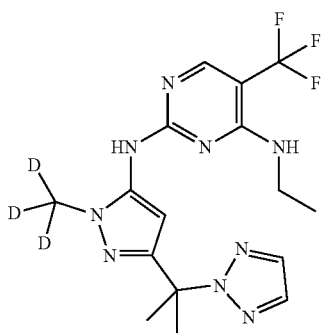 [SMILES: [2H]C([2H])([2H])n1nc(C(C)(C)n2nccn2)cc1Nc1ncc(C(F)(F)F)c(NCC)n1]

or a pharmaceutically acceptable salt thereof.

24. A method for treating a disease or condition mediated, at least in part, by LRRK2, wherein the disease or condition is selected from the group consisting of Parkinson's disease, dementia, Alzheimer's disease, L-Dopa induced dyskinesia, and amyotrophic lateral sclerosis, the method comprising administering to a subject in need thereof an effective amount of a compound having the structure:

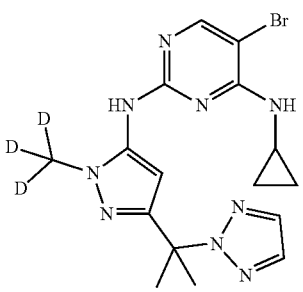 [SMILES: [2H]C([2H])([2H])n1nc(C(C)(C)n2nccn2)cc1Nc1ncc(Br)c(NC2CC2)n1]

or a pharmaceutically acceptable salt thereof.

25. The method of claim 1, wherein the disease or condition is Parkinson's disease.

26. The method of claim 18, wherein the disease or condition is Parkinson's disease.

27. The method of claim 19, wherein the disease or condition is Parkinson's disease.

* * * * *